US008420616B2

(12) United States Patent
Kotb et al.

(10) Patent No.: US 8,420,616 B2
(45) Date of Patent: Apr. 16, 2013

(54) MAT II BETA SUBUNIT RNAI AND THERAPEUTIC METHODS USING SAME

(75) Inventors: Malak Kotb, Ft. Thomas, KY (US); Arthur M. Geller, Ft. Thomas, KY (US)

(73) Assignee: University of Cincinnati, Cincinnati, OH (US)

( * ) Notice: Subject to any disclaimer, the term of this patent is extended or adjusted under 35 U.S.C. 154(b) by 105 days.

(21) Appl. No.: 12/936,780

(22) PCT Filed: Apr. 7, 2009

(86) PCT No.: PCT/US2009/039809

§ 371 (c)(1), (2), (4) Date: Dec. 20, 2010

(87) PCT Pub. No.: WO2009/126651

PCT Pub. Date: Oct. 15, 2009

(65) Prior Publication Data

US 2011/0129461 A1 Jun. 2, 2011

Related U.S. Application Data

(60) Provisional application No. 61/042,969, filed on Apr. 7, 2008.

(51) Int. Cl.
*A61K 31/70* (2006.01)
*C07H 21/04* (2006.01)

(52) U.S. Cl.
USPC .......................................... 514/44; 536/24.5

(58) Field of Classification Search ........................ None
See application file for complete search history.

(56) References Cited

U.S. PATENT DOCUMENTS

| | | | | |
|---|---|---|---|---|
| 6,696,279 | B1 | 2/2004 | Kotb et al. | |
| 2003/0143732 | A1 * | 7/2003 | Fosnaugh et al. ............ | 435/325 |

OTHER PUBLICATIONS

De La Rosa et al. Cancer Research 1992, vol. 52, pp. 3361-3366.*

Bass Nature 2001, vol. 411, pp. 428-429.*

Written Opinion of the International Searching Authority issued for PCT/US2009/039089, mailed Nov. 12, 2009.

LeGros et al, Regulation of the Human MAT2B Gene Encoding the Regulatory β Subunit of Methionine Adenosyltransferase, MAT II, J. Bio. Chem., 276(27):24918-24924 (Jul. 6, 2001).

Attia et al, Selective targeting of leukemic cell growth in vivo and in vitro using a gene silencing approach to diminish S-adenosylmethionine synthesis, J. Biol. Chem., 283(45): 30788-30795 (Aug. 2008).

Wang et al, Lentivirus mediated shRNA interference targeting MAT2B induces growth-inhibition and apoptosis in hepatocellular carcinoma, World J. Gastrocenterol, 14(29): 4633-4642 (Aug. 2008).

* cited by examiner

*Primary Examiner* — Tracy Vivlemore
(74) *Attorney, Agent, or Firm* — Dinsmore & Shohl LLP

(57) ABSTRACT

The presently disclosed subject matter generally relates to methods and compositions for modulating MAT II activity. More particularly, the presently disclosed subject matter relates to methods and compositions for inhibiting the expression of MAT II β subunit in a subject via RNAi by administering siRNA or shRNA molecules directed to MAT II β subunit. In some embodiments, the methods and compositions of the presently disclosed subject matter generally relates to the treatment of cancer. More particularly, the methods and compositions of the presently disclosed subject matter relates to the inhibition of MAT II β subunit for the treatment of leukemia.

36 Claims, 13 Drawing Sheets

SAM SYNTHESIS BY MAT ISOZYMES
METHIONINE S-ADENOSYLMETHIONINE SAM
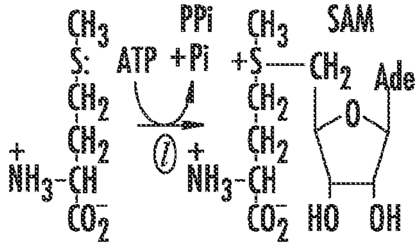
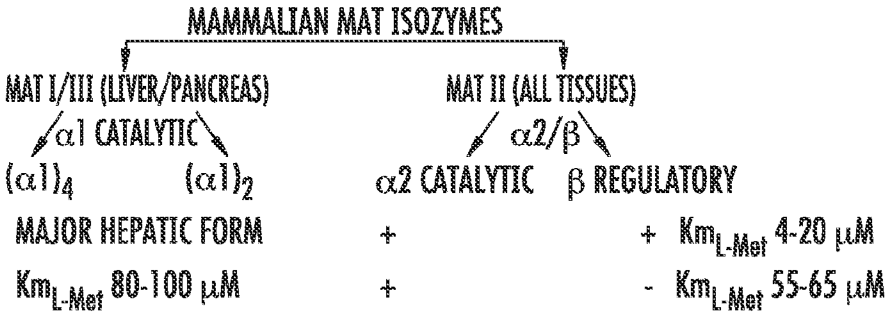
FIG. 1A SEQ ID NO: 1 (shRNA.β1.229)
3′ END OF THE H1 PROMOTER SENSE LOOP ANTISENSE TER XbaI
GGAATCTTATAAGTTCTGTATGAGACCACTCTTTCCCgcagttcatcacatcattcTTCAAGAGAgaatgatgtgatgaactgcTTTTTCTAGAGCA SEQ ID NO: 2 (MUTANT shRNA.β1mu)
3′ END OF THE H1 PROMOTER SENSE LOOP ANTISENSE TER XbaI
GGAATCTTATAAGTTCTGTATGAGACCACTCTTTCCCgcagttcatggatcattcTTCAAGAGAgaatgatccgatgaactgcTTTTTCTAGAGCA SEQ ID NO: 3 (shRNA.β2.830)
3′ END OF THE H1 PROMOTER SENSE LOOP ANTISENSE TER XbaI
GGAATCTTATAAGTTCTGTATGAGACCACTCTTTCCCgacctattactgacagcccTTCAAGAGAgggctgtcagtaataggtcTTTTTCTAGAGCA SEQ ID NO: 4 (MUTANT shRNA.β2mu)
3′ END OF THE H1 PROMOTER SENSE LOOP ANTISENSE TER XbaI
GGAATCTTATAAGTTCTGTATGAGACCACTCTTTCCCgacctattaacgacagcccTTCAAGAGAgggctgtcgttaataggtcTTTTTCTAGAGCA SEQ ID NO: 5 (shRNA.β744)
3′ END OF THE H1 PROMOTER SENSE LOOP ANTISENSE TER XbaI
GGAATCTTATAAGTTCTGTATGAGACCACTCTTTCCCtcactggtctggcaatgaaTTCAAGAGAttcattgccagaccagtgaTTTTTCTAGAGCA SEQ ID NO: 6 (shRNA.β1110)
3′ END OF THE H1 PROMOTER SENSE LOOP ANTISENSE TER XbaI
GGAATCTTATAAGTTCTGTATGAGACCACTCTTTCCCttaggatctttcaggtaaTTCAAGAGAttacctgaaagatcctaaTTTTTCTAGAGCA SEQ ID NO: 7 (shRNA.β1249)
3′ END OF THE H1 PROMOTER SENSE LOOP ANTISENSE TER XbaI
GGAATCTTATAAGTTCTGTATGAGACCACTCTTTCCCaaattatgatccttaaataTTCAAGAGAtatttaaggatcataatttTTTTTCTAGAGCA SEQ ID NO: 8 (MAT II β shRNA.1 USING PRIMER B1)
3′ END OF THE H1 PROMOTER SENSE LOOP ANTISENSE TER XbaI
GGAATCTTATAAGTTCTGTATGAGACCACTCTTTCCCgcagttcatcacatcattcTTCAAGAGAgaatgatgtgatgaactgcTTTTTCTAGA SEQ ID NO: 9 (MUTANT MAT II β shRNA.1m USING PRIMER B1m)
3′ END OF THE H1 PROMOTER SENSE LOOP ANTISENSE TER XbaI
GGAATCTTATAAGTTCTGTATGAGACCACTCTTTCCCgcagttcatcggatcattcTTCAAGAGAgaatgatccgatgaactgcTTTTTCTAGA SEQ ID NO: 10 (MAT II β shRNA.2 USING PRIMER B2)
3′ END OF THE H1 PROMOTER SENSE LOOP ANTISENSE TER XbaI
GGAATCTTATAAGTTCTGTATGAGACCACTCTTTCCCgacctattactgacagcccTTCAAGAGAgggctgtcagtaataggtcTTTTTCTAGA SEQ ID NO: 11 (MUTANT MAT II β shRNA.2m USING PRIMER B2m)
3′ END OF THE H1 PROMOTER SENSE LOOP ANTISENSE TER XbaI
GGAATCTTATAAGTTCTGTATGAGACCACTCTTTCCCgacctattaacgacagcccTTCAAGAGAgggctgtcgttaataggtcTTTTTCTAGA

FIG. 2

SEQ ID NO: 12 (MAT II β siRNA A-017193-13): CGGUCUUUCAUUAGUUUAU

SEQ ID NO: 13 (MAT II β siRNA A-017193-14): UUAGGAUCUUUCAGGUAAA

SEQ ID NO: 14 (MAT II β siRNA A-017193-15): CCUUAAAUAUUUGAGAGUC

SEQ ID NO: 15 (MAT II β siRNA A-017193-16): CUCUCAACUUAAUGUGGAU

20μM L-MET
LEUKEMIC CELL DEATH (% PI+ CELLS)

50μM L-MET
JURKAT
V1302
V1110

[L-MET] μM

NS
LEUKEMIC CELL APOPTOSIS (% ANNEXIN-V+,PI- CELLS)
DAYS IN CULTURE

PROPOSED Phi29 BASED APPROACH TO DEVELOP NANOPARTICLES FOR THE DELIVERY OF MAT-IIβ RNAI TO SPECIFIC LEUKEMIC CELLS IN VIVO

MAT II BETA SUBUNIT RNAI AND THERAPEUTIC METHODS USING SAME

RELATED APPLICATIONS

This application claims priority to U.S. Provisional Patent Application Ser. No. 61/042,969, filed Apr. 7, 2008, which is herein incorporated in its entirety.

GRANT STATEMENT

This work was supported by NIH grant R01CA108792. Thus, the U.S. Government has certain rights in the presently disclosed subject matter.

TECHNICAL FIELD

The presently disclosed subject matter relates generally to the modulation of the biological activity of methionine adenosyltransferase II (MAT II). More particularly, the presently disclosed subject matter relates to the modulation of MAT II β subunit polypeptides and methods of employing this modulation in the treatment of diseases.

ABBREVIATIONS

| | |
|---|---|
| BSA | bovine serum albumin |
| CDR(s) | complementarity determining region(s) |
| EST | expressed sequence tags |
| GC-MS | gas chromatography-Mass spectroscopy |
| HAT | cell culture media comprising hypoxanthine, aminopterin, and thymidine |
| HBSS | Hank's balanced salt solution |
| HPLC | high pressure liquid chromatography |
| KLH | keyhole limpet hemocyanin |
| MAT II | methionine adenosyltransferase II |
| MAT II α2 | methionine adenosyltransferase II α2 subunit |
| MAT II β | methionine adenosyltransferase II β subunit |
| myc | human oncogene used herein as molecular tag |
| ORF | open reading frame |
| PCR | polymerase chain reaction |
| PBMC | peripheral blood mononuclear cells |
| RACE | rapid amplification of cDNA ends |
| RNAi | RNA interference assay |
| SAM | S-adenosylmethionine |
| shRNA | short hairpin RNA |
| siRNA | small interfering RNA |
| UTR | untranslated region |

BACKGROUND

In a typical clinical setting, radiation therapy and/or chemotherapy treatments are administered to the majority (>90%) of cancer patients. Therefore, along with surgery, radiation therapy and chemotherapy represent two of the three main modalities employed for cancer treatment. However, the therapeutic outcomes are still far from ideal for many types of tumors. The main problem associated with radiotherapy is the recurrence of tumors and/or the development of metastases at distant locations. For chemotherapy, the problem is the development of resistance. Often, both radiotherapy and chemotherapy are associated with severe side effects. In both cases, new methods and compositions that can sensitize tumors to current treatments are highly desirable. Ideally, these methods and compositions should decrease local recurrences in patients treated with radiotherapy and/or should increase the efficacy of chemotherapeutic agents systemically. In addition, they should not have severe side effects.

Methionine adenosyltransferase (MAT) is a key enzyme required for every living cell. MAT II, an isozyme of MAT, is found in all human tissues and it is made of two nonidentical subunits that are called alpha (α2) and beta (β). MAT II β is the regulatory subunit, which regulates MAT II activity.

MAT, including MAT II, is responsible for the synthesis of one of the most important molecules in living organisms, called S-adenosylmethionine (SAM, or AdoMet). It has been shown that in certain types of cancerous cells require abnormally high levels of SAM. Therefore, MAT has been studied for years as a possible target for chemotherapy. Many scientists tried to develop inhibitors of this enzyme but most chemical inhibitors are highly toxic or lack specificity. Further, the synthesis of these chemical inhibitors in amounts that would be sufficient for treatment is costly.

What are needed, then, are new strategies and compositions for treating tumors and/or cancers via inhibition of MAT II activity that minimizes toxicity and/or improves specificity. The presently disclosed subject matter addresses this and other needs in the art.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In some embodiments, the presently disclosed subject matter provides a method of modulating MAT II activity in a vertebrate subject, the method comprising administering to the vertebrate subject an effective amount of a substance capable of modulating expression of the MAT II β subunit in the vertebrate subject, wherein the substance comprises an RNA interference (RNAi) molecule directed to MAT II β subunit, whereby modulation of MAT II activity is accomplished. In some embodiments, modulating the expression of MAT II β subunit comprises modulating expression of the MAT2B gene. In some embodiments, modulating MAT II activity comprises decreasing SAM synthesis. In some embodiments, wherein the RNAi molecule comprises a short hairpin RNA (shRNA), whereby the shRNA modulates expression of MAT II β subunit by RNAi. In some embodiments, the shRNA comprises a nucleotide sequence of one of SEQ ID NOs: 1-11. In some embodiments, the substance further comprises a delivery vehicle, such as but not limited to a viral vector, an antibody, an aptamer or a nanoparticle, for delivering the shRNA to a target cell. In some embodiments, the RNAi molecule comprises a small interfering RNA (siRNA), whereby the siRNA modulates expression of MAT II β subunit by RNAi. In some embodiments, the siRNA comprises a nucleotide sequence of one of SEQ ID NOs: 12-15. In some embodiments, the substance further comprises a delivery vehicle, such as but not limited to a viral vector, an antibody, an aptamer, or a nanoparticle for delivering the siRNA to a target cell. In some embodiments, MAT II activity is modulated by interfering with MAT II β subunit interaction with MAT II α2 catalytic subunit. In some embodiments, the vertebrate is a mammal.

In some embodiments, the presently disclosed subject matter provides a method of treating a subject suffering from a disorder associated with MAT II biological activity in the subject, the method comprising: administering to the subject an effective amount of a substance capable of modulating expression of MAT II β subunit in the subject, whereby modulation of the expression of MAT II β subunit is accomplished; and modulating MAT II biological activity in the subject through the modulation of the expression of MAT II β subunit, or through the modulation of MAT II β subunit interaction with MAT II α2 subunit, whereby treatment of the disorder is accomplished. In some embodiments, the modulated expression of MAT II β subunit comprises the modulated expression of the MAT2B gene. In some embodiments, the substance that modulates expression of a MAT II β subunit comprises an RNAi molecule. In some embodiments, the RNAi molecule is an shRNA molecule of SEQ ID NO: 1-11 or an siRNA molecule of SEQ ID NO: 12-15, whereby the shRNA molecule or siRNA molecule modulates expression of MAT II β subunit by RNAi. In some embodiments, the shRNA or siRNA is delivered to a target cell by a delivery vehicle, such as but not limited to a viral vector, an antibody, an aptamer, or a nanoparticle. In some embodiments, the method further comprises the administration of radiation therapy, chemotherapy, gene therapy, immunotherapy, a dietary treatment, or combinations thereof. In some embodiments, the disorder is cancer. In some embodiments, the cancer is leukemia. In some embodiments, the substance that modulates MAT II β subunit interaction with MAT II α2 subunit comprises a small molecule, peptide, antibody or aptamer.

In some embodiments, the presently disclosed subject matter provides a method of treating a subject suffering from a disorder associated with MAT II biological activity in the patient, the method comprising administering to the subject a therapeutic composition comprising a MAT II β subunit siRNA, shRNA, miRNA, hammerhead ribozyme, or other molecule that interferes with the MAT II β biological activity by reducing its expression or a therapeutic composition comprising a small molecule, peptide, antibody or aptamer capable of interfering with the interaction between the MAT II β subunit and the MAT II α2 subunit, whereby the disorder is treated. In some embodiments, the MAT II biological activity comprises MAT II biological activity endogenous to the subject. In some embodiments, the MAT II β subunit shRNA comprises a nucleotide sequence of SEQ ID NOs: 1-11 or the siRNA comprising a nucleotide sequence of one of SEQ ID NOs: 12-15. In some embodiments, the therapeutic composition further comprises a delivery vehicle, such as but not limited to a viral vector, an antibody, an aptamer, or a nanoparticle for delivering the therapeutic compositon to a target cell. In some embodiments, modulating MAT II biological activity comprises modulating MAT II specific activity. In some embodiments, modulating MAT II biological activity comprises modulating MAT II enzyme kinetics. In some embodiments, modulating MAT II biological activity results in decreased production of SAM. In some embodiments, the method further comprises the administration of radiation therapy, chemotherapy, gene therapy, immunotherapy, a dietary treatment, or combinations thereof. In some embodiments, the disorder is cancer. In some embodiments, the disorder is leukemia.

In some embodiments, the presently disclosed subject matter provides a method for modulating MAT II biological activity in a cell comprising: delivering to the cell an effective amount of a vector comprising a polynucleotide that encodes a MAT II β subunit siRNA, shRNA, miRNA, hammerhead ribozyme, or other molecule that interferes with the MAT II β biological activity by reducing its expression, or a therapeutic composition comprising a small molecule, peptide, antibody or aptamer capable of interfering with the interaction between the MAT II β subunit and the MAT II α2 subunit, wherein MAT II biological activity is modulated; and maintaining the cell under conditions sufficient for expression of said siRNA, shRNA, miRNA, hammerhead ribozyme, or a molecule that interferes with the MAT II β biological activity by modulating its expression or interfering with its interaction with MAT II α2 subunit. I n some embodiments, the shRNA comprises a nucleotide sequence of SEQ ID NOs: 1-11 or the siRNA comprising a nucleotide sequence of one of SEQ ID NOs: 12-15. In some embodiments, the method further comprises a delivery vehicle, such as but not limited to a viral vector, an aptamer, an antibody or a nanoparticle, for delivering the siRNA, shRNA, miRNA, or hammerhead ribozyme to the cell. In some embodiments, the cell is a leukemic cell or other cancer cell where modulating MAT II biological activity could have a therapeutic effect. In some embodiments, the cancer cell is a primary cancer cell or a cell line representing a primary cancer cell.

In some embodiments, the presently disclosed subject matter provides a method for suppressing the growth of a cancer cell, the method comprising: contacting the cancer cell with a vector encoding an RNAi molecule selected from the group including but not limited to an siRNA, shRNA, miRNA, or hammerhead ribozyme un der conditions sufficient to allow entry of the vector into the cell, wherein the RNAi molecule comprises a ribonucleotide sequence corresponding to a coding strand of a MAT II β subunit gene; and decreasing the biological activity of MAT II by siRNA, shRNA miRNA, or hammerhead ribozyme mediated down-regulation of MAT II β subunit gene expression through RNAi, wherein the decreased biological activity of MAT II suppresses the growth of the cancer cell. In some embodiments, the siRNA or shRNA down-regulates the expression of MAT II β subunit by inhibiting expression of the MAT2B gene. In some embodiments, the cell is in a subject. In some embodiments, the subject is a mammal. In some embodiments, the vector is a retroviral vector. In some embodiments, the shRNA comprises a nucleotide sequence of SEQ ID NOs: 1-11 or the siRNA comprising a nucleotide sequence of one of SEQ ID NOs: 12-15. In some embodiments, the method further comprises a delivery vehicle, such as but not limited to a viral vector, an antibody, an aptamer, or a nanoparticle for delivering the siRNA, shRNA, miRNA, or hammerhead ribozyme to the cell. In some embodiments, the cancer cell is a leukemic cell, a leukemic T or B cell, or other cancer cell where modulating MAT II biological activity could have a therapeutic effect.

In some embodiments, the presently disclosed subject matter provides an RNAi construct capable of modulating expression of a MAT II β subunit gene, whereby MAT II biological activity is modulated. In some embodiments, the RNAi construct comprises a siRNA, shRNA, miRNA, or hammerhed ribozyme. In some embodiments, the siRNA, shRNA, miRNA, or hammerhed ribozyme is specific for a vertebrate MAT II β subunit gene. In some embodiments, the siRNA, shRNA, miRNA, or hammerhed ribozyme is specific for a human MAT II β subunit gene. In some embodiments, the MAT II β subunit gene is MAT2B. In some embodiments, the expression of MAT II β subunit is down-regulated, whereby the biological activity of MAT II is suppressed. In some embodiments, the siRNA or shRNA comprises a sense region, an antisense region, and a loop region, positioned in relation to each other such that upon transcription, the resulting RNA molecule is capable of forming a hairpin structure via intramolecular hybridization of the sense strand and the antisense strand. In some embodiments, the siRNA or shRNA comprises a nucleotide sequence of one of SEQ ID NOs: 1-15. In some embodiments, modulating MAT II biological activity comprises modulating MAT II specific activity. In some embodiments, modulating MAT II biological activity comprises modulating MAT II enzyme kinetics. In some embodiments, modulating MAT II biological activity results in decreased production of SAM. In some embodiments, modulating MAT II biological activity results in decreased cell growth. In some embodiments, the decreased cell growth comprises decreased cell growth of a leukemic cell, a leukemic T or B cell, or other cancer cell where modulating MAT II biological activity could have a therapeutic effect. In some embodiments, the RNAi construct is in a pharmaceutically acceptable carrier. In some embodiments an expression vector comprising a nucleic acid sequence encoding an RNAi construct is provided. In some embodiments, the vector is a retroviral vector. In some embodiments, a mammalian cell comprising the expression vector is provided. In some embodiments, the cell is a leukemic cell, a leukemic T or B cell, or other cancer cell where modulating MAT II biological activity could have a therapeutic effect.

In some embodiments, the presently disclosed subject matter provides a method of generating MAT II β subunit siRNA, shRNA, miRNA or hammerhead ribozyme comprising: transfecting a cell with a vector expressing MAT II β subunit siRNA, shRNA, miRNA or hammerhead ribozyme under conditions suitable for the expression of said vector. In some embodiments, the vector is a retroviral vector. In some embodiments, the vector comprises a promoter operatively linked to a nucleic acid molecule encoding the siRNA, shRNA, miRNA or hammerhead ribozyme and a transcription termination sequence. In some embodiments, the promoter is a DNA-dependent RNA polymerase III promoter.

In some embodiments, the presently disclosed subject matter provides a pharmaceutical composition comprising a therapeutically effective amount of a MAT II β subunit modulator and a pharmaceutically acceptable diluent or vehicle. In some embodiments, the MAT II β subunit modulator is an siRNA, shRNA, miRNA or hammerhead ribozyme. In some embodiments, the siRNA, shRNA, miRNA or hammerhead ribozyme modulates expression of the MAT2B gene. In some embodiments, the shRNA comprises a nucleotide sequence of SEQ ID NOs: 1-11 or the siRNA comprising a nucleotide sequence of one of SEQ ID NOs: 12-15. In some embodiments, the siRNA, shRNA, miRNA or hammerhead ribozyme is conjugated to a nanoparticle. In some embodiments, the siRNA, shRNA, miRNA or hammerhead ribozyme is conjugated to a nanoparticle, to which an antibody or an aptamer is attached to direct delivery of the siRNA, shRNA, miRNA or hammerhead ribozyme to the target cancer cell.

It is an object of the presently disclosed subject matter to provide methods for modulating MAT II β subunit expression to thereby modulate MAT II activity and treat conditions such as cancer.

An object of the presently disclosed subject matter having been stated above, other objects and advantages will become apparent to those of ordinary skill in the art after a study of the following description of the presently disclosed subject matter and non-limiting Examples.

BRIEF DESCRIPTION OF THE DRAWINGS

FIGS. 1A and 1B are diagrams of S-adenosylmethionine (SAM) synthesis and SAM metabolism, respectively. FIG. 1A shows the conversion of methionine to SAM by way of methionine adenosyltransferase (MAT). FIG. 1A also depicts the MAT isozymes, their regulatory and catalytic roles, and effect on MAT enzyme kinetics and activity. FIG. 1B depicts the central role of SAM in metabolism.

FIG. 2 depicts the design of MAT II β specific shRNA constructs (SEQ ID NOs: 1-11) used in the presently disclosed subject matter.

FIG. 5A is a Western blot digital image of a Western blot depicting MAT II α2 protein expression. FIG. 5B is a digital image of a Western blot depicting MAT II β protein expression. FIG. 5C is a bar graph depicting MAT II α2 mRNA concentrations. FIG. 5D is a bar graph depicting MAT II β mRNA concentrations. MAT II α2 and β protein expression (60 μg protein/well) and mRNA levels were analyzed in untransduced or ≧98% transduced cells as detailed in herein. QRT-PCR was conducted using RNA extracted from cells maintained in 100 μM L-Met RPMI medium and RNA copy number was calculated as detailed in Methods. Results (mean±SEM) are of 2 combined experiments, each done in triplicate. Statistical differences were determined as described herein. MAT II β protein expression and mRNA concentrations were significantly ablated in V1110 cells (***p≦0.001); MAT II α2 was slightly elevated or unaffected (p>0.05).

FIG. 6A depicts MAT II Lineweaver-Burk kinetic plots of 1/V for V1110-transduced cells (left panel) and V1302-transduced and untransduced cells (controls; right panel), where V is Units of enzyme activity per mg protein (U/mg; U=1 nmol SAM/h). MAT assays were performed using extracts from untransduced, V1110- or V1302-transduced cells in the presence of 2.5-80 μM L-Met. The data for each cell extract represents mean±SD of three separate experiments, each assayed in triplicate. FIG. 6B is a bar graph depicting MAT specific activity (U/mg protein) at 20 μM L-Met for untransduced (open bars), V1110- (solid bars) or V1302-transduced (hatched bars) cells. FIG. 6C is a bar graph of SAMe levels (pmole/$10^6$ cells) as determined by HPLC in neutralized PCA extracts from untransduced (open bars), V1110- (solid bars) and V1302-transduced (hatched bars) cells that were maintained at 50 or 20 μM L-Met. *p≦0.05, p≦0.01, *p≦0.001.

FIG. 8A depicts PI-stained necrotic cells (%) at 20 μM L-Met. FIG. 8B depicts PI-stained necrotic cells (%) at 50 μM L-Met. FIG. 8C depicts necrotic cells (%) at 6 days in 5-50 μM L-Met. FIG. 8D depicts Annexin-V stained apoptotic cells (%) at 20 μM L-Met. FIG. 8E depicts Annexin-V stained apoptotic cells (%) at 50 μM L-Met. FIG. 8F depicts apoptotic cells (%) at 6 days in 5-50 μM L-Met. In the line graphs (FIGS. 8A, 8B, 8D and 8E) data are shown for untransduced (open circles), V1110- (solid squares) and V1302-transduced (open squares) cells. In the bar graphs (FIGS. 8C and 8F) data are shown for untransduced (open bars), V1110- (solid bars) and V1302-transduced (hatched bars) cells. *p≦0.05, p≦0.01, *p≦0.001.

FIGS. 10A and 10B are flow cytometry histograms of $CD3^+/GFP^+$ in spleen (FIG. 10A) or bone marrow (FIG. 10B) 5 weeks post-transplant. FIG. 10C depicts images of GFP expression in whole spleens of control mice and mice engrafted with V1302 or V1110 leukemic cells prior to processing their splenocytes. FIG. 10D is a bar graph depicting the number of mice engrafted with V1302 (hatched bars) or V1110 (solid bars) leukemic cells at 4 and 5 weeks post-transplant. FIGS. 10E and 10F show % $CD3^+/GFP^+$ cells in spleens (FIG. 10E) or bone marrow (FIG. 10F) of control mice and mice transplanted with either V1302 or V1110 leukemic cells, 5 weeks post-transplant. Statistical differences were calculated using Mann-Whitney test (*p≦0.05, p≦0.01, *p≦0.001).

BRIEF DESCRIPTION OF THE SEQUENCE LISTING

Figure 1B:
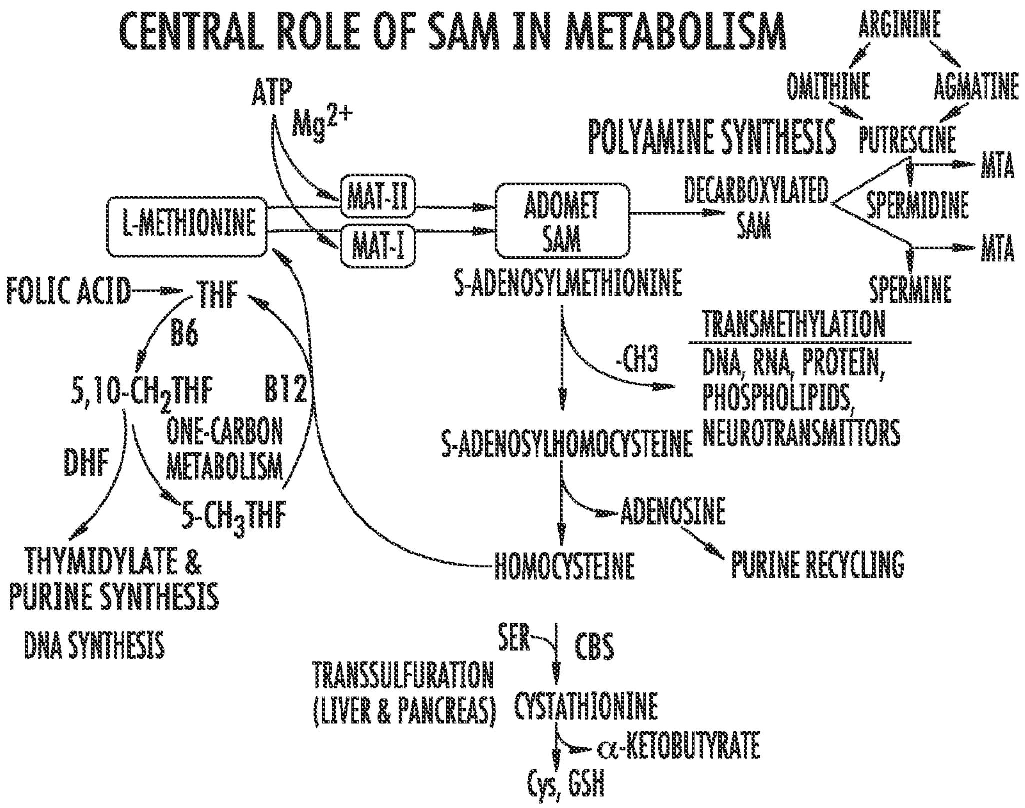

SEQ ID NO: 1 is a polynucleotide sequence for an shRNA construct which corresponds to a short segment of the coding strand of human MAT II β subunit, referred to herein as shRNA.β1.229.

SEQ ID NO: 2 is a polynucleotide sequence for an shRNA construct which corresponds to a short segment of the coding strand of human MAT II β subunit, referred to herein as shRNA.β1mu SEQ ID NO: 3 is a polynucleotide sequence for an shRNA construct which corresponds to a short segment of the coding strand of human MAT II β subunit, referred to herein as shRNA.β2.830.

SEQ ID NO: 4 is a polynucleotide sequence for an shRNA construct which corresponds to a short segment of the coding strand of human MAT II β subunit, referred to herein as shRNA.β2mu.

SEQ ID NO: 5 is a polynucleotide sequence for an shRNA construct which corresponds to a short segment of the coding strand of human MAT II β subunit, referred to herein as shRNA.β7441.

SEQ ID NO: 6 is a polynucleotide sequence for an shRNA construct which corresponds to a short segment of the coding strand of human MAT II β subunit, referred to herein as shRNA.β1110.

SEQ ID NO: 7 is a polynucleotide sequence for an shRNA construct which corresponds to a short segment of the coding strand of human MAT II β subunit, referred to herein as shRNA.β1249.

SEQ ID NO: 8 is a polynucleotide sequence for an shRNA construct which corresponds to a short segment of the coding strand of human MAT II β subunit, referred to herein as shRNA.1.

SEQ ID NO: 9 is a polynucleotide sequence for an shRNA construct which corresponds to a short segment of the coding strand of human MAT II β subunit, referred to herein as shRNA.1m.

SEQ ID NO: 10 is a polynucleotide sequence for an shRNA construct which corresponds to a short segment of the coding strand of human MAT II β subunit, referred to herein as shRNA.2.

SEQ ID NO: 11 is a polynucleotide sequence for an shRNA construct which corresponds to a short segment of the coding strand of human MAT II β subunit, referred to herein as shRNA.2m.

SEQ ID NO: 12 is a polynucleotide sequence for an siRNA construct which corresponds to a short segment of the coding strand of human MAT II β subunit, referred to herein as siRNA A-017193-13.

SEQ ID NO: 13 is a polynucleotide sequence for an siRNA construct which corresponds to a short segment of the coding strand of human MAT II β subunit, referred to herein as siRNA A-017193-14.

SEQ ID NO: 14 is a polynucleotide sequence for an siRNA construct which corresponds to a short segment of the coding strand of human MAT II β subunit, referred to herein as siRNA A-017193-15.

SEQ ID NO: 15 is a polynucleotide sequence for an siRNA construct which corresponds to a short segment of the coding strand of human MAT II β subunit, referred to herein as siRNA A-017193-16.

SEQ ID NO: 16 is a short segment of human MAT II β subunit polynucleotide sequence targeted by siRNA and/or shRNA constructs in some embodiments of the presently disclosed subject matter.

SEQ ID NO: 17 is a forward primer used in some embodiments for the generation of siRNA constructs.

SEQ ID NO: 18 is a reverse primer used in some embodiments for the generation of siRNA constructs.

SEQ ID NO: 19 is a sense primer used in some embodiments for the generation of siRNA constructs.

SEQ ID NO: 20 is a antisense primer used in some embodiments for the generation of siRNA constructs.

SEQ ID NO: 21 is a human MAT II β subunit polynucleotide sequence with deduced amino acid sequences shown for the open reading frame (ORF).

SEQ ID NO: 22 is a human MAT II β subunit amino acid sequence encoded by the polynucleotide sequence of SEQ ID NO: 21.

SEQ ID NO: 23 is a human MAT II β subunit polynucleotide sequence with deduced amino acid sequences shown for the ORF.

SEQ ID NO: 24 is a human MAT II β subunit amino acid sequence encoded by the polynucleotide sequence of SEQ ID NO: 23.

SEQ ID NO: 25 is a human MAT II β subunit polynucleotide sequence with deduced amino acid sequences shown for the ORF.

SEQ ID NO: 26 is a human MAT II β subunit amino acid sequence encoded by the polynucleotide sequence of SEQ ID NO: 25.

SEQ ID NO: 27 is a human MAT II β subunit polynucleotide sequence with deduced amino acid sequences shown for the ORF.

SEQ ID NO: 28 is a human MAT II β subunit amino acid sequence encoded by the polynucleotide sequence of SEQ ID NO: 27.

SEQ ID NO: 29 is a human MAT II β subunit polynucleotide sequence with deduced amino acid sequences shown for the ORF.

SEQ ID NO: 30 is a human MAT II β subunit amino acid sequence encoded by the polynucleotide sequence of SEQ ID NO: 29.

DETAILED DESCRIPTION

I. General Considerations

Methionine adenosyltransferase (MAT; S-adenosyl-L-methionine (SAM) synthetase, EC 2.5.1.6) is an essential enzyme that catalyzes the synthesis of S-adenosylmethionine (SAM) from L-methionine (L-Met) and ATP (FIG. 1A; Cantoni, G. L. (1953) *J. Biol. Chem.* 204: 403-416; Mudd, S. H. (1973) The Adenosyltransferases, Third Edition Ed. The Enzymes, Group Transfer (Part A) (Bayer, P. D., Ed.), III). As shown in FIG. 1B, SAM is the major methyl group donor, participating in the methylation of proteins, DNA, RNA, phospholipids and other small molecules (reviewed in Finkelstein et al. (1975) *Biochem. Biophys. Res. Commun.* 66: 81-7; Tabor, C. W., and Tabor, H. (1984) *Adv. Enzymol. Relat. Areas Mol. Biol.* 56: 251-82; Mudd et al. (1995) Disorders of transsulfuration, 7th Ed. The Molecular and Metabolic Basis of Inherited Diseases (Scriver, C. R., Beaudet, A. L., Sly, W. S., and Valle, D., Eds.), McGraw-Hill Inc., New York).

SAM is the ultimate source of the propylamine moiety used in polyamine biosynthesis, and it serves as co-factor for other key enzymes in the one-carbon metabolism pathway (Finkelstein et al. (1975) Biochem. Biophys. Res. Commun. 66: 81-7; Tabor, C. W., and Tabor, H. (1984) Adv. Enzymol. Relat. Areas Mol. Biol. 56: 251-82; Mudd et al. (1995) Disorders of transsulfuration, 7th Ed. The Molecular and Metabolic Basis of Inherited Diseases (Scriver, C. R., Beaudet, A. L., Sly, W. S., and Valle, D., Eds.), McGraw-Hill Inc., New York). In polyamine synthesis, SAM is decarboxylated by SAM decarboxylase and its propylamino moiety attached to its sulfonium ion is utilized in the synthesis of polyamines including putrescine and spermidine, which play a key role in cell division apoptosis and function. Methylthioadenosine (MTA), generated as a by-product in this pathway is also involved in regulating several cellular functions. In transmethylation reactions, the CH3 group attached to the sulfonium ion of SAM is donated to key molecules such as proteins, DNA, RNA, lipids and a large number small metabolic compounds in reactions catalyzed by specialized methyltransferases (MT). Methylation confers certain functionalities upon these molecules and is thus essential in the regulation of many metabolic pathways, cell differentiation and functions. Upon donating its methyl group, SAM is converted to S-adenosylhomocysteine (Hcy) and adenosine, a reaction catalyzed by Hcy hydrolase. Hcy is a potent inhibitor of methylation reactions, but both Hcy and adenosine also play an important role in cardiovascular diseases. The adenosine moiety of SAM is converted to inosine in a deamination reaction catalyzed by adenosine demaninase, an important enzyme whose deficiency leads to serious immune and cardiac malfunctions and inhibition of biological transmethylation due to SAH accumulation. Hcy can be remethylated to form methionine via methionine synthase (MS), which requires folate and vitamin $B_{12}$ and betaine homocysteine methyltransferase, which requires betaine. Remethylation of homocysteine via MS requires 5-methyltetrahydrofolate (5-MTHF), and the generated THF is converted to 5,10-MTHF, which is important for thymidylate and purine synthesis. Hcy can also become converted to cysteine (liver & pancreas), the rate-limiting precursor for glutathione (GSH), via the transsulfuration pathway via a two-step enzymatic process catalyzed by cystathionine β-synthase (CBS) and cystathionase, both requiring vitamin $B_6$.

MAT is present in all living species, including thermophilic archaebacteria, plants, yeast, and mammals (reviewed in Tabor, C. W., and Tabor, H. (1984) Adv. Enzymol. Relat. Areas Mol. Biol. 56: 251-82; Kotb, M., and Geller, A. M. (1993) Pharmacol. Ther. 59: 125-43; Chiang, et al. (1996) FASEB J. 10: 471-80; Mato et al. (1997) Pharmacol. Ther. 73: 265-80). Interestingly, most species have more than one MAT isozyme (Kotb, M., and Geller, A. M. (1993) Pharmacol. Ther. 59: 125-43).

Mammalian MAT exists in multiple forms that differ in their physical and kinetic properties among distinct species and even among different tissues of the same species. In mammals there are three forms designated MAT I, II, and III that differ in their tissue distribution and kinetic properties (Hoffman, J. L. (1983) Methods Enzymol. 94, 223-8; Mato et al. (1994) Adv. Exp. Med. Biol. 368, 113-7; Okada et al. (1981) Biochemistry 20, 934-40; Kotb et al. (1997) Trends Genet. 13, 51-2). MAT I and III are referred to as the hepatic forms because their expression is confined to the liver. By contrast, MAT II is found in all mammalian tissues that have been examined to date, including erythrocytes, lymphocytes, brain, kidney, testis, and liver (Okada et al. (1981) Biochemistry 20, 934-40; Oden, K., and Clarke, S. (1983) Biochemistry 22, 2978-2986; Kotb, M., and Kredich, N. M. (1985) J. Biol. Chem. 260, 3923-30; Langkamp-Henken et al. (1994) Biochim. Biophys. Acta 1201, 397-404; Liau et al. (1979) Cancer Res. 39, 162-69; Sullivan, D. M., and Hoffman, J. L. (1983) Biochemistry 22, 1636-41; Mitsui et al. (1988) J. Biol. Chem. 263, 11211-16; Horikawa et al. (1990) J. Biol. Chem. 265, 13683-86).

MAT I is a tetramer and MAT III is a dimer of an identical catalytic subunit, $\alpha 1$, encoded by the MATIA gene (referred to herein as MAT2B) (Hoffman, J. L. (1983) Methods Enzymol. 94, 223-8; Horikawa, S., and Tsukada, K. (1991) Biochem. Int. 25, 81-90; Alvarez et al. (1993) Biochem. J. 293, 481-86; Sakata et al. (1993) J. Biol. Chem. 268, 13978-86; Ubagai et al. (1995) J. Clin. Invest. 96, 1943-47). On the other hand, MAT II from leukemic T cells, such as a primary leukemic T cell, or from activated human lymphocytes is a hetero-oligmer consisting of $\alpha 2$ (53 kDa), $\alpha' 2$ (51 kDa) and $\beta$ (38 kDa) subunits (Kotb, M., and Kredich, N. M. (1985) J. Biol. Chem. 260, 3923-30). The $\alpha 2$ and $\alpha' 2$ are the catalytic subunits while $\beta$ has a regulatory function (De La Rosa et al. (1992) J. Biol. Chem. 267, 10699-704; De La Rosa et al. (1995) J. Biol. Chem. 270:21860-68; LeGros et al. (1997) J. Biol. Chem. 272, 16040-47; Halim et al. (1999) J. Biol. Chem. 274, 29720-5; LeGros et al. (2000) J. Biol. Chem. 275, 2359-66). The $\alpha 2$ and $\alpha' 2$ subunits are immunologically crossreactive and essentially identical to each other, but quite different from the $\beta$ subunit. The $\alpha 2$ subunit, which appears to be posttranslationally processed to yield $\alpha' 2$ (Kotb, M., and Kredich, N. M. (1985) J. Biol. Chem. 260, 3923-30), is encoded by the MAT2A gene which is homologous, but different from MAT1A gene (Kotb et al. (1997) Trends Genet. 13, 51-2; Horikawa, S., and Tsukada, K. (1991) Biochem. Int. 25, 81-90; De La Rosa et al. (1995) J. Biol. Chem. 270:21860-68).

The human MAT II from human lymphocytes has been analyzed to apparent homogeneity (Kotb, M., and Kredich, N. M. (1985) J. Biol. Chem. 260: 3923-30; Kotb, M., and Kredich, N. M. (1990) Biochim. Biophys. Acta 1039(2): 253-60; De La Rosa et al. (1992) J. Biol. Chem. 267: 10699-704; De La Rosa et al. (1995) J. Biol. Chem. 270, 21860-8; LeGros et al. (1997) J. Biol. Chem. 272, 16040-7), and it has been shown that the form present in activated lymphocytes includes distinct subunits (Kotb, M., and Kredich, N. M. (1985) J. Biol. Chem. 260, 3923-30; De La Rosa et al. (1992) J. Biol. Chem. 267, 10699-704; De La Rosa et al. (1992) Cancer Res 52, 3361-6; Halim et al. (1999) J. Biol. Chem. 274, 29720-5; LeGros et al. (2000) J. Biol. Chem. 275, 2359-66). The catalytic MAT II $\alpha 2$ subunit, which is encoded by the MAT2A gene, was cloned and characterized and found to be homologous, but different from the catalytic al subunit of the liver MAT I/III isozyme (Horikawa, S., and Tsukada, K. (1991) Biochem. Int. 25, 81-90; Alvarez et al. (1993) Biochem. J. 293, 481-6; Sakata et al. (1993) J. Biol. Chem. 268, 13978-86; Horikawa et al. (1990) J. Biol. Chem. 265, 13683-6; De La Rosa et al. (1995) J. Biol. Chem. 270, 21860-8; Halim et al. (1999) J. Biol. Chem. 274, 29720-5). The MAT II $\alpha 2$ subunit, which has a calculated molecular weight of 43,600, migrates on SDS-PAGE gels as a 53 kDa protein, and is postranslationally modified to generate MAT II $\alpha 2'$ subunit (Kotb, M., and Kredich, N. M. (1985) J. Biol. Chem. 260, 3923-30). The catalytic $\alpha 2/\alpha 2'$ subunits are found in native MAT II associated with a catalytically inactive subunit designated MAT II $\beta$, which migrates on SDS-PAGE as a 38-kDa protein (Kotb, M., and Kredich, N. M. (1985) J. Biol. Chem. 260, 3923-30; De La Rosa et al. (1992) J. Biol. Chem. 267, 10699-704; LeGros et al. (1997) J. Biol. Chem. 272, 16040-7). Physiological activation of human lymphocytes induces downregulation of the $\beta$ subunit with co-incidental alterations in MAT II kinetic properties (LeGros et al. (1997) J. Biol. Chem. 272, 16040-47). Expression of recombinant MAT II $\alpha 2$ in the absence of MAT II $\beta$ exhibits altered MAT II kinetic properties (Halim et al. (1999) J. Biol. Chem. 274, 29720-5).

In accordance with the presently disclosed subject matter, silencing of the $\beta$ subunit of MAT II also alters MAT II kinetic properties. MAT II $\alpha 2$ in the absence of MAT II $\beta$ has a substantially higher Km (lower affinity) for L-Met than when MAT II $\beta$ is present. When MAT II $\beta$ is absent MAT II $\alpha 2$ Km for L-Met is considerably increased by 5-10 fold, rendering the enzyme inactive or considerably less active in physiologic levels of L-Met found outside the liver. As a consequence, MAT II $\alpha 2$, in the absence of MAT II $\beta$, synthesizes much less SAM outside the liver under physiologic conditions. Stated another way, the absence of MAT II $\beta$ in extrahepatic tissues reduces intracellular SAM levels.

Also in accordance with the presently disclosed subject matter, blocking or interfering with the interaction between the MAT II $\beta$ subunit and the MAT II $\alpha 2$ subunit alters MAT II kinetic properties and activity. Blocking the binding of the MAT II $\beta$ subunit and the MAT II $\alpha 2$ subunit renders the MAT II enzyme inactive or considerably less active in physiologic levels of L-Met found outside the liver. As a consequence, MAT II synthesizes substantially less SAM outside the liver under physiologic conditions. Stated another way, the blocking of MAT II $\beta$ subunit binding to MAT II $\alpha 2$ in extrahepatic tissues reduces intracellular SAM levels.

The importance of regulating SAM levels and methylation reactions can be seen in certain types of cancer where an abnormal amount of methylation can result in the suppression or over-expression of critical genes. Cells have a finely controlled cycle of division followed by cell death. A disruption of this cycle can result in abnormal amount of cell growth resulting in the development of tumors. See, Belinsky et al., *Proc. Natl. Acad. Sci. USA* (1998) 20:11891-6; Ahuja et al., *Cancer Res.* (1998) 23:5489-94; Klump et al., *Gastroenterology* (1998) 6:1381-6. For the above reasons, MAT has been studied for years as a possible target for chemotherapy. Many scientists tried to develop inhibitors of this enzyme but most chemical inhibitors are highly toxic or lack specificity. Further, the synthesis of these chemical inhibitors is costly.

The present inventors have found that the activity of MAT II can be regulated by its $\beta$ subunit. When $\beta$ expression is absent, the MAT II $\alpha 2$ subunits make at least 5-10 fold more SAM in the cell as compared to when $\beta$ is expressed.

As mentioned above, the present inventors have found that the activity of MAT II can be regulated by its $\beta$ subunit. When $\beta$ expression is absent, the MAT II $\alpha 2$ subunits require at least 5-10 fold more L-Met in the cell to synthesize SAM as compared to when the $\beta$ subunit is expressed. Additionally, MAT II activity, SAM utilization rate and SAM pool size are respectively, 20, 60 and 60-100 fold higher in lymphocytic leukemias, than in normal lymphocytes. Further, in established and primary human lymphocytic leukemic cells, MAT II $\beta$ expression is significantly higher than in quiescent or activated primary lymphocytes.

In addition, several studies have reported that the expression of MAT II $\beta$ subunit is considerably elevated in hepatocellular carcinoma and other organ cancers. Thus, modulation of the expression of the MAT II $\beta$ subunit via molecular methods provides for changes in the activity of MAT II and this provides a tool for cancer therapy, as well as the treatment of any other diseases or conditions associated with MAT II activity and/or MAT II $\beta$ subunit expression.

Because of the stark difference in SAM metabolism and in the expression and need for MAT II $\beta$ between several normal cells and their cancerous counterparts, the presently disclosed subject matter exploits these differences to provide approaches that preferentially diminish the growth of cancerous cells in physiologic environments, while having little or no effect on normal cells. Inhibition of MAT II activity can be effected by modulating the expression of MAT II $\beta$, which is overexpressed in several types of cancers.

Summarily, the presently disclosed subject matter provides compositions and methods for modulating MAT II biological activity in cells, such as cancerous cells, for example leukemic cells or cancerous liver cells. In some embodiments, the methods comprise providing one or more cancerous cells, such as leukemic cells or cancerous liver cells, the cancerous cells being in a subject such as a human; and contacting the cancerous cells with a composition comprising an RNA molecule comprising an siRNA or shRNA, the siRNA or shRNA, or any RNAi construct modulating MAT II biological activity through RNAi induced down-regulation of MAT II $\beta$ subunit expression, wherein the RNAi induced down-regulation of MAT II $\beta$ subunit expression is mediated by suppressing the expression of a polynucleotide sequence encoding a MAT II $\beta$ subunit as set forth in SEQ ID NOs: 21, 23, 25, 27 and 29, whereby decreased MAT II biological activity suppresses cell growth and/or viability of the cancerous cells. In some embodiments, the compositions comprise an RNA molecule, such as an siRNA or shRNA molecule, or any RNAi construct capable of modulating MAT II $\beta$ subunit expression, including all splice variants of MAT II $\beta$ RNA or protein (Yang et al. (2008) *Gastroenterology* 134, 281-91), in the cancerous cells.

Also provided in the presently disclosed subject matter are compositions and methods for modulating MAT II biological activity in cells, such as cancerous cells, for example leukemic cells or cancerous liver cells. MAT II biological activity can be modulated by blocking or interfering with the interaction between the MAT II $\beta$ subunit and the MAT II $\alpha 2$ subunit. In some embodiments, the methods comprise providing one or more cancerous cells, such as leukemic cells or cancerous liver cells, the cancerous cells being in a subject such as a human; and contacting the cancerous cells with a composition comprising a small molecule, an aptamer, a peptide, an antibody or any other compound or molecule capable of blocking or interfering with the interaction between the MAT II $\beta$ subunit and the MAT II $\alpha 2$ subunit.

The disclosure of U.S. Pat. No. 6,696,279 is incorporated herein by reference in its entirety. Additionally, all other patent documents and other references cited herein are incorporated by reference in their entireties.

II. SAM Metabolism and Cancer

Despite advancements in novel individual and combination drug treatment modalities, mortality rates among patients with cancers, particularly leukemic patients, remain high and some medications have serious adverse effects (Pui, C. H., and Jeha, S. (2007) Nat Rev Drug Discov 6(2), 149-165; Cunningham, L., and Aplenc, R. (2007) Expert Opin Pharmacother 8(15), 2519-2531). Leukemia are among the deadliest and most common cancers. There remains a need to develop novel approaches that exploit physiological differences in metabolic needs between normal and cancerous cells, e.g., leukemic, cells to generate tools that would selectively diminish tumor cell growth in vivo, with minimal harm to normal host cells. Significant differences in metabolism between normal and cancerous cells, particularly lymphocytic leukemias, have been identified (De La Rosa, J., Geller, A. M., LeGros, H. L., Jr., and Kotb, M. (1992) Cancer Res 52, 3361-3366; De La Rosa, J., LeGros, H. L., Jr., Geller, A. M., and Kotb, M. (1992) J Biol Chem 267(15), 10699-10704). In accordance with the presently disclosed subject matter, methods and compositions are provided to exploit these significant differences in metabolism between normal and cancerous cells and to develop therapeutics that would selectively compromise the survival of the malignant cells with little or no harm to normal cells.

Several studies have suggested that abnormal elevation in the MAT II enzyme with a subsequent elevation in SAM levels plays a role in facilitating cancer growth. In some cases, MAT II is induced in the liver during periods of rapid growth and dedifferentiation and in human hepatocellular carcinoma (HCC) MAT I is replaced by MAT II (Cai J, et al. (1966). Hepatology. 24, 1090-7). Elevations in the MAT II enzyme have been reported in colon cancers (Ito K et al. (2000) and in Surg. Today 30, 706-710) and in human hepatoma (Liu et al. (2007) Hepatol. Res. 375, 366-88).

Abnormal SAM metabolism has been documented in a variety of human cancers. For example, serum SAM levels were fund to be elevated in patients with lung cancer as compared to smokers with benign lung disorders and healthy nonsmokers (Greenberg et al. (2007) Chest 132, 1247-1252) and methylation of several tumor-suppressor genes promoters have been documented early in the development of lung cancer (Belinsky S A et al. (2004) Cancer 4, 1-11; Herman J G, et al. (2003) N Engl J Med. 349, 2042-2054; Belinsky S A et al. (2005) Clin Cancer Res. 11, 6505-6511). Elevated levels of homocysteine, an important metabolite of SAM have been found to be a predictive and sensitive biomarker of invasive cervical cancer (Weinstein S J et al. (2001) Cancer Causes and Control 12, 317-324). Elevations in the levels of the polyamines, another important metabolite of SAM, are also elevated in colon cancer to the extent that inhibitors of polyamine synthesis are used to treat colon cancers (Zhang et al. (2006) Gene Medicine 8.

SAM is an essential molecule in the metabolism of every living species (Cantoni, G. L. (1953) J Biol Chem 204(1), 403-416; Tabor, C. W., and Tabor, H. (1984) Adv Enzymol Relat Areas Mol Biol 56, 251-282; Kotb, M., and Geller, A. M. (1993) Pharmacol Ther 59(2), 125-143; Chiang et al., (1996) FASEB J 10(4), 471-480; Mato et al., (1997) Pharmacol Ther 73(3), 265-280). As the main methyl group donor, it methylates DNA, RNA, fatty acids, proteins and small molecules, and regulates several transcription and translation processes, protein function, and membrane integrity. SAM is also involved in DNA mismatch repair, chromatin modeling, epigenetic modifications and imprinting, cell replication, neurotransmission, and signaling (Loenen, W. A. (2006) Biochem Soc Trans 34(Pt 2), 330-333). Additionally, SAM is an important precursor of the polyamines and a major player in biological transsulfuration as well as folic acid and one-carbon metabolism (Kotb, M., and Geller, A. M. (1993) Pharmacol Ther 59(2), 125-143; Chiang et al., (1996) FASEB J 10(4), 471-480; Loenen, W. A. (2006) Biochem Soc Trans 34(Pt 2), 330-333; Tabor, C. W., and Tabor, H. (1984) Annu Rev Biochem 53, 749-790).

The importance of SAM, together with the fact that its metabolism is constitutively elevated in malignant versus normal cells, has for years, made it an attractive target for cancer chemotherapy (Coulter et al., (1974) Mol Pharmacol. 10(2), 319-334; Sufrin, J., Coulter, A., and Talalay, P. (1979) Mol Pharmacol 15(3), 661-677; Federici, M. M., and Lotspeich, F. J. (1979) Biochem Pharmacol 28(10), 1689-1693; Kappler et al., (1988) J Med Chem 31(2), 384-389; Lavrador et al., (1998) J Enzyme Inhib 13(5), 361-367; Lombardini, J. B., and Sufrin, J. R. (1983) Biochem Pharmacol 32(3), 489-495; Vrudhula et al., (1989) J Med Chem. 32(4), 885-890; Sufrin et al., (1993) Biochim Biophys Acta 1202(1), 87-91). Unfortunately, chemical inhibitors of SAM synthesis have been difficult to generate in quantities needed for clinical use, and most were unstable, reversible, nonspecific and/or highly toxic because no cell can survive total inhibition of SAM synthesis. To this end, the presently disclosed subject matter provides methods and compositions designed to take advantage of the dependency on higher SAM levels in cancerous cells, such as but not limited to leukemic cells, to diminish rather than totally block their ability to synthesize needed amount of SAM and thereby selectively halt their growth while sparing normal cells.

Novel biotools that can selectively silence protein expression are disclosed herein to target the regulatory subunit of methionine adenosyltransferase (MAT), which catalyzes the synthesis of SAM from L-Methionine (L-Met) and ATP. All living organisms have at least one MAT enzyme (De La Rosa, J., LeGros, H. L, Jr., Geller, A. M., and Kotb, M. (1992) J Biol Chem 267(15), 10699-10704; Coulter et al., (1974) Mol Pharmacol. 10(2), 319-334). Mammals have a liver specific MAT-I/III and another isozyme, MAT-II that is expressed in all tissues (Kotb et al., (1985) J Biol Chem 260(7), 3923-3930; Kotb et al., (1997) Trends Genet 13(2), 51-52). MAT-I/III are tetramer/dimer forms of a catalytic α1 subunit, and they differ considerably in their kinetic and physical properties. It is believed that this differential oligomerization of MAT-α1 is an important adaptation to cope with special metabolic requirements in the liver, where SAM levels need to be maintained at a certain range inasmuch as a deficiency or excess of SAMe has been associated with serious pathology (Hoffman, J. L. (1983) Methods Enzymol 94, 223-228; Mato et al., (2002) Faseb J 16(1), 15-26; Suma, Y., Shimizu, K., and Tsukada, K. (1986) J Biochem 100(1), 67-75). In livers of healthy subjects, MAT-III which has a high $Km_{L\text{-}Met}$ (80-100 μM) is the major isoform. By contrast, MAT II is a hetero-oligomer that has a catalytic α2 subunit and a regulatory β subunit with a $Km_{L\text{-}Met}$ 4-20 μM (Kotb, M., and Kredich, N. M. (1985) J Biol Chem 260(7), 3923-3930; Halim, A. B., LeGros, L., Geller, A., and Kotb, M. (1999) J Biol Chem 274(42), 29720-29725). The α2 subunit, which has 84% sequence identity to α1, undergoes posttranslational modifications resulting in expression of α2 (53kDA) and α2' (51 kDa) forms (Kotb, M., and Kredich, N. M. (1985) J Biol Chem 260(7), 3923-3930). In fetal liver and certain adult liver diseases, including hepatocellular carcinoma, al subunit expression is diminished and replaced by α2, along with the induction of MAT II β expression (Garcia-Trevijano et al., (2000) FASEB J 14(15), 2511-2518; Yang et al., (2008) Gastroenterology 134(1), 281-291).

MAT α subunits are highly conserved across many species (Kotb et al., (1997) Trends Genet 13(2), 51-52); by contrast MAT II β is mainly found in mammals, associated with MAT II α2. MAT II β plays a physiological role by lowering the Km of MAT II for L-Met from 55-65 μM down to 3.5-20 μM (Halim et al., (1999) J Biol Chem 274(42), 29720-29725; LeGros et al., (2000) J Biol Chem 275(4), 2359-2366). Inasmuch as the physiologic extrahepatic concentration of L-Met are 5-10-fold lower than that in the liver (Finkelstein, J. D. (1990) J Nutr Biochem 1(5), 228-237), it is believed that the introduction of MAT II β to lower the Km of the extrahepatic enzyme could have been an evolutionary event that allowed MAT II to function in blood and other extrahepatic mammalian tissues, where L-Met levels are ~10-25 μM (Finkelstein, J. D. (2006) J Nutr 136(6 Suppl), 1750S-1754S; Loehrer et al., (1997) J Pharmacol Exp. Ther 282(2), 845-850; Baric, I., et al. (2004) Proc Natl Acad Sci USA 101(12), 4234-4239).

MAT II expression and SAM metabolism are considerably different in normal and malignant cells including lymphocytes (De La Rosa et al., (1992) Cancer Res 52, 3361-3366; De La Rosa et al., (1992) J Biol Chem 267(15), 10699-10704; Kotb, M., and Geller, A. M. (1993) Pharmacol Ther 59(2), 125-143). MAT II β expression in established and primary human lymphocytic leukemia cells is significantly higher than in quiescent or activated lymphocytes (De La Rosa et al., (1992) Cancer Res 52, 3361-3366). MAT II activity, SAM utilization rate, and SAM pool size are respectively, 20, 60 and 60-100 fold higher in lymphocytic leukemia, than in normal lymphocytes (De La Rosa et al., (1992) Cancer Res 52, 3361-3366).

Provided herein for the first time, however, is the disclosure that if MAT II β expression was specifically ablated, MAT II $Km_{L\text{-}Met}$ could be shifted by at least 10-fold above physiologic L-Met levels, and that this would consequently reduce SAM pool size and selectively diminish the growth of leukemic cells in physiological fluids and extrahepatic tissues. Thus, the presently disclosed methods and compositions are designed to selectively inhibit the expression of the MAT II β regulatory subunit in cancerous cells in vivo to thereby induce excessive apoptosis and diminish the growth of cancerous cells such as leukemic cells.

III. Definitions

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a" and "an" mean "one or more" when used in this application, including the claims.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, "significance" or "significant" relates to a statistical analysis of the probability that there is a non-random association between two or more entities. To determine whether or not a relationship is "significant" or has "significance", statistical manipulations of the data can be performed to calculate a probability, expressed as a "p value". Those p values that fall below a user-defined cutoff point are regarded as significant. In some embodiments, a p value less than or equal to 0.05, in some embodiments less than 0.01, in some embodiments less than 0.005, and in some embodiments less than 0.001, are regarded as significant. Accordingly, a p value greater than or equal to 0.05 is considered not significant.

As used herein, the term "subject" refers to any organism for which application of the presently disclosed subject matter would be desirable. The subject treated in the presently disclosed subject matter in its many embodiments is desirably a human subject, although it is to be understood that the principles of the presently disclosed subject matter indicate that the presently disclosed subject matter is effective with respect to all vertebrate species, including mammals, which are intended to be included in the term "subject". Moreover, a mammal is understood to include any mammalian species in which treatment of a tumor and/or a cancer is desirable, particularly agricultural and domestic mammalian species.

The term "isolated", as used in the context of a nucleic acid molecule or polypeptide, indicates that the nucleic acid molecule or polypeptide exists apart from its native environment and is not a product of nature. An isolated nucleic acid molecule or polypeptide can exist in a purified form or can exist in a non-native environment such as a host cell.

The term "complementary" refers to two nucleotide sequences that comprise antiparallel nucleotide sequences capable of pairing with one another upon formation of hydrogen bonds between the complementary base residues in the antiparallel nucleotide sequences. As is known in the art, the nucleic acid sequences of two complementary strands are the reverse complement of each other when each is viewed in the 5' to 3' direction.

As used herein, the phrase "percent complementarity" refers to the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). The terms "100% complementary", "fully complementary", and "perfectly complementary" indicate that all of the contiguous residues of a nucleic acid sequence can hydrogen bond with the same number of contiguous residues in a second nucleic acid sequence.

The term "subsequence" refers to a sequence of a nucleic acid or polypeptide that comprises a part of a longer nucleic acid or polypeptide sequence.

The term "elongated sequence" refers to an addition of nucleotides (or other analogous molecules) or amino acid residues incorporated into the nucleic acid or polypeptide. For example, a polymerase (e.g., a DNA polymerase) can add sequences at the 3' terminus of the nucleic acid molecule. In addition, the nucleotide sequence can be combined with other DNA sequences, such as promoters, promoter regions, enhancers, polyadenylation signals, intronic sequences, additional restriction enzyme sites, multiple cloning sites, and other coding segments.

The terms "operatively linked" and "operably linked", as used herein, refer to a nucleic acid molecule in which a promoter region is connected to a nucleotide sequence in such a way that the transcription of that nucleotide sequence is controlled and regulated by the promoter region. Similarly, a nucleotide sequence is said to be under the "transcriptional control" of a promoter to which it is operably linked. Techniques for operatively linking a promoter region to a nucleotide sequence are known in the art.

The terms "heterologous gene", "heterologous DNA sequence", "heterologous nucleotide sequence", "exogenous nucleic acid molecule", or "exogenous DNA segment", as used herein, each refer to a sequence that originates from a source foreign to an intended host cell and/or, if from the same source, is modified from its original form. Thus, a heterologous gene in a host cell includes a gene that is endogenous to the particular host cell but has been modified, for example by mutagenesis and/or by isolation from native transcriptional regulatory sequences. The terms also include non-naturally occurring multiple copies of a naturally occurring nucleotide sequence. Thus, the terms refer in some embodiments to a DNA segment that is foreign or heterologous to the cell, or is homologous to the cell but in a position within the host cell nucleic acid wherein the element is not ordinarily found.

The term "expression vector" as used herein refers to a nucleotide sequence capable of directing expression of a particular nucleotide sequence in an appropriate host cell, comprising a promoter operatively linked to the nucleotide sequence of interest which is operatively linked to termination signals. It also typically comprises sequences required for proper translation of the nucleotide sequence. The construct comprising the nucleotide sequence of interest can be chimeric. The construct can also be one that is naturally occurring but has been obtained in a recombinant form useful for heterologous expression.

The term "promoter" or "promoter region" each refers to a nucleotide sequence within a gene that is positioned 5' to a coding sequence and functions to direct transcription of the coding sequence. The promoter region comprises a transcriptional start site, and can additionally include one or more transcriptional regulatory elements.

A "minimal promoter" is a nucleotide sequence that has the minimal elements required to enable basal level transcription to occur. As such, minimal promoters are not complete promoters but rather are subsequences of promoters that are capable of directing a basal level of transcription of a reporter construct in an experimental system. Minimal promoters include but are not limited to the CMV minimal promoter, the HSV-tk minimal promoter, the simian virus 40 (SV40) minimal promoter, the human β-actin minimal promoter, the human EF2 minimal promoter, the adenovirus E1B minimal promoter, and the heat shock protein (hsp) 70 minimal promoter. Minimal promoters are often augmented with one or more transcriptional regulatory elements to influence the transcription of an operably linked gene. For example, cell-type-specific or tissue-specific transcriptional regulatory elements can be added to minimal promoters to create recombinant promoters that direct transcription of an operably linked nucleotide sequence in a cell-type-specific or tissue-specific manner Different promoters have different combinations of transcriptional regulatory elements. Whether or not a gene is expressed in a cell is dependent on a combination of the particular transcriptional regulatory elements that make up the gene's promoter and the different transcription factors that are present within the nucleus of the cell. As such, promoters are often classified as "constitutive", "tissue-specific", "cell-type-specific", or "inducible", depending on their functional activities in vivo or in vitro. For example, a constitutive promoter is one that is capable of directing transcription of a gene in a variety of cell types. Exemplary constitutive promoters include the promoters for the following genes which encode certain constitutive or "housekeeping" functions: hypoxanthine phosphoribosyl transferase (HPRT), dihydrofolate reductase (DHFR; (Scharfmann et al., 1991), adenosine deaminase, phosphoglycerate kinase (PGK), pyruvate kinase, phosphoglycerate mutase, the β-actin promoter (see e.g., Williams et al., 1993), and other constitutive promoters known to those of skill in the art. "Tissue-specific" or "cell-type-specific" promoters, on the other hand, direct transcription in some tissues and cell types but are inactive in others. Exemplary tissue-specific promoters include the PSA promoter (Yu et al., 1999; Lee et al., 2000), the probasin promoter (Greenberg et al., 1994; Yu et al., 1999), and the MUC1 promoter (Kurihara et al., 2000) as discussed above, as well as other tissue-specific and cell-type specific promoters known to those of skill in the art.

The term "transcriptional regulatory sequence" or "transcriptional regulatory element", as used herein, each refers to a nucleotide sequence within the promoter region that enables responsiveness to a regulatory transcription factor. Responsiveness can encompass a decrease or an increase in transcriptional output and is mediated by binding of the transcription factor to the DNA molecule comprising the transcriptional regulatory element.

The term "transcription factor" generally refers to a protein that modulates gene expression by interaction with the transcriptional regulatory element and cellular components for transcription, including RNA polymerase, Transcription Associated Factors (TAFs), chromatin-remodeling proteins, and any other relevant protein that impacts gene transcription.

The terms "reporter gene" or "marker gene" or "selectable marker" each refer to a heterologous gene encoding a product that is readily observed and/or quantitated. A reporter gene is heterologous in that it originates from a source foreign to an intended host cell or, if from the same source, is modified from its original form. Non-limiting examples of detectable reporter genes that can be operatively linked to a transcriptional regulatory region can be found in Alam & Cook, 1990 and PCT International Publication No. WO 97/47763. Exemplary reporter genes for transcriptional analyses include the lacZ gene (see e.g., Rose & Botstein, 1983), Green Fluorescent Protein (GFP; Cubitt et al., 1995), luciferase, and chloramphenicol acetyl transferase (CAT). Reporter genes for methods to produce transgenic animals include but are not limited to antibiotic resistance genes, for example the antibiotic resistance gene confers neomycin resistance. Any suitable reporter and detection method can be used, and it will be appreciated by one of skill in the art that no particular choice is essential to or a limitation of the presently disclosed subject matter.

An amount of reporter gene can be assayed by any method for qualitatively or quantitatively determining presence or activity of the reporter gene product. The amount of reporter gene expression directed by each test promoter region fragment is compared to an amount of reporter gene expression to a control construct comprising the reporter gene in the absence of a promoter region fragment. A promoter region fragment is identified as having promoter activity when there is significant increase in an amount of reporter gene expression in a test construct as compared to a control construct. The term "significant increase", as used herein, refers to an quantified change in a measurable quality that is larger than the margin of error inherent in the measurement technique, in one example an increase by about 2-fold or greater relative to a control measurement, in another example an increase by about 5-fold or greater, and in yet another example an increase by about 10-fold or greater.

Nucleic acids of the presently disclosed subject matter can be cloned, synthesized, recombinantly altered, mutagenized, or combinations thereof. Standard recombinant DNA and molecular cloning techniques used to isolate nucleic acids are known in the art. Exemplary, non-limiting methods are described by Silhavy et al., 1984; Ausubel et al., 1992; Glover & Hames, 1995; and Sambrook & Russell, 2001). Site-specific mutagenesis to create base pair changes, deletions, or small insertions is also known in the art as exemplified by publications (see e.g., Adelman et al., 1983; Sambrook & Russell, 2001).

As used herein, the term "cell" is used in its usual biological sense. In some embodiments, the cell is present in an organism, for example, mammals such as humans, cows, sheep, apes, monkeys, swine, dogs, cats, and rodents. In some embodiments, the cell is a eukaryotic cell (e.g., a mammalian cell, such as a human cell). The cell can be of somatic or germ line origin, totipotent or pluripotent, dividing or non-dividing. The cell can also be derived from or can comprise a gamete or embryo, a stem cell, or a fully differentiated cell.

As used herein, the term "RNA" refers to a molecule comprising at least one ribonucleotide residue. By "ribonucleotide" is meant a nucleotide with a hydroxyl group at the 2' position of a β-D-ribofuranose moiety. The terms encompass double stranded RNA, single stranded RNA, RNAs with both double stranded and single stranded regions, isolated RNA such as partially purified RNA, essentially pure RNA, synthetic RNA, recombinantly produced RNA, as well as altered RNA, or analog RNA, that differs from naturally occurring RNA by the addition, deletion, substitution, and/or alteration of one or more nucleotides. Such alterations can include addition of non-nucleotide material. Nucleotides in the RNA molecules of the presently disclosed subject matter can also comprise non-standard nucleotides, such as non-naturally occurring nucleotides or chemically synthesized nucleotides or deoxynucleotides. These altered RNAs can be referred to as analogs or analogs of a naturally occurring RNA.

RNA interference (RNAi) is a natural process by which living cells can control which genes are expressed or suppressed. As used herein, the term "RNAi" refers to a mechanism that silences specific genes by inhibiting an RNA molecule and stopping or at least substantially reducing the expression of the protein encoded by this RNA molecule. If the target protein has a function in the cell, RNAi approaches can result in loss of that function. As such, RNAi technology is an attractive therapeutic tool to modulate the expression of genes in a way to suppress disease. RNAi can be mediated by several natural and synthetic constructs, including double stranded RNA (dsRNA), or smaller dsRNA known as small interfering RNAs (siRNA), short hairpin RNA (shRNA), microRNA (miRNA), or synthetic hammerhead ribozymes. These can be referred to as examples of RNAi molecules.

As used herein, the phrase "double stranded RNA" refers to an RNA molecule at least a part of which is in Watson-Crick base pairing forming a duplex. As such, the term is to be understood to encompass an RNA molecule that is either fully or only partially double stranded. Exemplary double stranded RNAs include, but are not limited to molecules comprising at least two distinct RNA strands that are either partially or fully duplexed by intermolecular hybridization. Additionally, the term is intended to include a single RNA molecule that by intramolecular hybridization can form a double stranded region (for example, a hairpin). Thus, as used herein the phrases "intermolecular hybridization" and "intramolecular hybridization" refer to double stranded molecules for which the nucleotides involved in the duplex formation are present on different molecules or the same molecule, respectively.

As used herein, the phrase "double stranded region" refers to any region of a nucleic acid molecule that is in a double stranded conformation via hydrogen bonding between the nucleotides including, but not limited to hydrogen bonding between cytosine and guanosine, adenosine and thymidine, adenosine and uracil, and any other nucleic acid duplex as would be understood by one of ordinary skill in the art. The length of the double stranded region can vary from about 15 consecutive basepairs to several thousand basepairs.

As used herein, the terms "corresponds to", "corresponding to", and grammatical variants thereof refer to a nucleotide sequence that is 100% identical to at least 19 contiguous nucleotides of a nucleic acid sequence encoding a MAT II β subunit, i.e. MAT2B gene. Thus, a first nucleic acid sequence that "corresponds to" a coding strand of a MAT II β subunit gene is a nucleic acid sequence that is 100% identical to at least 19 contiguous nucleotides of a MAT II β subunit gene, including, but not limited to 5' untranslated sequences, exon sequences, intron sequences, and 3' untranslated sequences.

The term "tumor" as used herein encompasses both primary and metastasized solid tumors and carcinomas of any tissue in a subject, including, but not limited to breast; colon; rectum; lung; oropharynx; hypopharynx; esophagus; stomach; pancreas; liver; gallbladder; bile ducts; small intestine; urinary tract including kidney, bladder and urothelium; female genital tract including cervix, uterus, ovaries (e.g., choriocarcinoma and gestational trophoblastic disease); male genital tract including prostate, seminal vesicles, testes and germ cell tumors; endocrine glands including thyroid, adrenal, and pituitary; skin (e.g., hemangiomas and melanomas), bone or soft tissues; blood vessels (e.g., Kaposi's sarcoma); brain, nerves, eyes, and meninges (e.g., astrocytomas, gliomas, glioblastomas, retinoblastomas, neuromas, neuroblastomas, Schwannomas and meningiomas). The term "tumor" also encompasses solid tumors arising from hematopoietic malignancies such as leukemias, including chloromas, plasmacytomas, plaques and tumors of mycosis fungoides and cutaneous T-cell lymphoma/leukemia, and lymphomas including both Hodgkin's and non-Hodgkin's lymphomas. The term "tumor" also encompasses radioresistant and/or chemoresistant tumors, including, but not limited to radioresistant and/or chemoresistant variants of the any of the tumor listed above.

As used herein, the terms "effective amount" and "therapeutically effective amount" are used interchangeably and mean a dosage sufficient to provide treatment for the disease state being treated. This can vary depending on the patient, the disease and the treatment being effected.

The term "gene" is used broadly to refer to any segment of DNA associated with a biological function. Thus, genes include, but are not limited to, coding sequences and/or the regulatory sequences required for their expression. Genes can also include non-expressed DNA segments that, for example, form recognition sequences for a polypeptide. Genes can be obtained from a variety of sources, including cloning from a source of interest or synthesizing from known or predicted sequence information, and can include sequences designed to have desired parameters.

The term "MAT II β subunit" includes MAT II β subunit nucleic acids and polypeptides that modulate the biological activity of the MAT II enzyme. MAT II β subunit nucleic acids and polypeptides can be isolated from eukaryotic sources. MAT II β polypeptide can be chemically synthesized. Thus, the term "MAT II β subunit" includes all naturally occurring or synthetic MT II β RNA splice forms and also includes invertebrate homologs. The term "MAT II β subunit" further includes vertebrate homologs of MAT II β subunit members, including, but not limited to, mammalian and avian homologs. Preferred mammalian homologs of MAT II β subunit members include, but are not limited to, murine, zebrafish, flies, bovine and human homologs.

The terms "MAT II β subunit gene product", "MAT II β subunit protein" and "MAT II β subunit polypeptide" refer to proteins having amino acid sequences which are substantially identical to the native amino acid sequences in the MAT II β subunit and which are biologically active in that they are capable of modulating MAT II biological activity, or cross-reacting with anti-MAT II β subunit antibodies raised against a MAT II β subunit polypeptide. By way of example and not limitation, a MAT II β subunit protein of the presently disclosed subject matter can be any of even numbered SEQ ID NOs: 22-30.

The terms "MAT II β subunit gene product", "MAT II β subunit protein" and "MAT II β subunit polypeptide" also include analogs of MAT II β subunit molecules which exhibit at least some biological activity in common with native MAT II β subunit gene products. Furthermore, those skilled in the art of mutagenesis will appreciate that other analogs, as yet undisclosed or undiscovered, can be used to construct MAT II β subunit analogs. There is no need for an "MAT II β subunit gene product", "MAT II β subunit protein" or "MAT II β subunit polypeptide" to comprise all, or substantially all of the amino acid sequence of a native MAT II β subunit gene product. Shorter or longer sequences can be of use in the presently disclosed subject matter. Thus, the term "MAT II β subunit gene product" also includes fusion or recombinant MAT II β subunit polypeptides and proteins.

The terms "MAT II β subunit gene", "MAT II β subunit gene sequence" and "MAT II β subunit gene segment" refer to any DNA sequence that is substantially identical to a polynucleotide sequence encoding a MAT II β subunit gene product, MAT II β subunit protein or MAT II β polypeptide as defined above. A "MAT II β subunit gene", "MAT II β subunit gene sequence", "MAT II β subunit gene segment" and "MAT II β subunit gene splice variant" can also comprise any combination of associated control sequences. By way of example and not limitation, a MAT II β subunit gene sequence of the presently disclosed subject matter can be any of odd numbered SEQ ID NOs: 21-30.

The terms "MAT II β subunit activity" and "MAT II β subunit biological activity" are meant to be synonymous and are meant to refer to any biological activity of a MAT II β subunit polypeptide. Exemplary biological activities of MAT II β subunit comprise activity in the modulation of MAT II biological activity, modulation of levels of SAM, and modulation of cell growth, proliferation and/or differentiation, apoptosis or other biological activity in accordance with the presently disclosed subject matter.

The term "substantially identical", when used to define either a MAT II β subunit gene product or MAT II β subunit amino acid sequence, or a MAT II β subunit gene or MAT II β subunit nucleic acid sequence, means that a particular sequence, for example, a mutant sequence, varies from the sequence of a natural MAT II β subunit by one or more deletions, substitutions, or additions, the net effect of which is to retain at least some of biological activity of the MAT II β subunit. Alternatively, DNA analog sequences are "substantially identical" to specific DNA sequences disclosed herein if: (a) the DNA analog sequence is derived from coding regions of the natural MAT II β subunit gene; or (b) the DNA analog sequence is capable of hybridization of DNA sequences of (a) under moderately stringent conditions and which encode biologically active MAT II β subunit gene product; or (c) the DNA sequences are degenerative as a result of the genetic code to the DNA analog sequences defined in (a) and/or (b). Substantially identical analog proteins will be greater than about 60% identical to the corresponding sequence of the native protein. Sequences having lesser degrees of similarity but comparable biological activity are considered to be equivalents. In determining nucleic acid sequences, all subject nucleic acid sequences capable of encoding substantially similar amino acid sequences are considered to be substantially similar to a reference nucleic acid sequence, regardless of differences in codon sequences.

Nucleotide sequences are "substantially identical" where they have between about 70% and about 80% or more preferably, between about 81% and about 90%, or even more preferably, between about 91% and about 99%, sequence identity for nucleic acid residues which are identical to the nucleotide sequence of a MAT II β subunit gene.

The term "gene expression" generally refers to the cellular processes by which a biologically active polypeptide is produced from a DNA sequence and exhibits a biological activity in a cell. As such, gene expression involves the processes of transcription and translation, but also involves post-transcriptional and post-translational processes that can influence a biological activity of a gene or gene product. These processes include, but are not limited to RNA syntheses, processing, and transport, as well as polypeptide synthesis, transport, and post-translational modification of polypeptides. Additionally, processes that affect protein-protein interactions within the cell can also affect gene expression as defined herein.

The term "modulate" refers to a change in the expression level of a gene, or a level of RNA molecule or equivalent RNA molecules encoding one or more proteins or protein subunits, or activity of one or more proteins or protein subunits is up regulated or down regulated, such that expression, level, or activity is greater than or less than that observed in the absence of the modulator. For example, the term "modulate" can mean "inhibit" or "suppress", but the use of the word "modulate" is not limited to this definition.

As used herein, the terms "silence", "ablate", "inhibit", "suppress", "downregulate", "loss of function", "block of function", and grammatical variants thereof are used interchangeably and refer to an activity whereby gene expression (e.g., a level of an RNA encoding one or more gene products) is reduced below that observed in the absence of a composition of the presently disclosed subject matter. In some embodiments, inhibition results in a decrease in the steady state level of a target RNA. In some embodiments, inhibition results in an expression level of a gene product that is below that level observed in the absence of the modulator.

In some embodiments, the terms "inhibit", "suppress", "downregulate", "block of function" and grammatical variants thereof refer to a biological activity of a polypeptide or polypeptide complex that is lower in the presence of a modulator than that which occurs in the absence of the modulator. For example, a modulator can inhibit expression or function of the MAT II β subunit, thereby inhibiting the activity of MAT II in physiological extrahepatic L-Met concentration. This can be accomplished by any mechanism, including but not limited to enhancing its existence in an inactive form and/or by enhancing the rate of degradation of MAT II β subunit. In accordance with the presently disclosed subject matter, suppression of MAT II activity can be effected if expression of MAT II β is reduced to level where the ratio of MAT II β to MAT II α2 is below 0.75 (75%), preferably below 0.3 (30%), more preferably below 0.1 (10%), or even more preferably below 0.01 (1%).

As used herein, the terms "gene" and "target gene" refer to a nucleic acid that encodes an RNA, for example, nucleic acid sequences including, but not limited to, structural genes encoding a polypeptide. The target gene can be a gene derived from a cell, an endogenous gene, a transgene, etc. The cell containing the target gene can be derived from or contained in any organism, for example an animal. The term "gene" also refers broadly to any segment of DNA associated with a biological function. As such, the term "gene" encompasses sequences including but not limited to a coding sequence, a promoter region, a transcriptional regulatory sequence, a non-expressed DNA segment that is a specific recognition sequence for regulatory proteins, a non-expressed DNA segment that contributes to gene expression, a DNA segment designed to have desired parameters, or combinations thereof. A gene can be obtained by a variety of methods, including cloning from a biological sample, synthesis based on known or predicted sequence information, and recombinant derivation of an existing sequence.

As is understood in the art, a gene comprises a coding strand and a non-coding strand. As used herein, the terms "coding strand" and "sense strand" are used interchangeably, and refer to a nucleic acid sequence that has the same sequence of nucleotides as an mRNA from which the gene product is translated. As is also understood in the art, when the coding strand and/or sense strand is used to refer to a DNA molecule, the coding/sense strand includes thymidine residues instead of the uridine residues found in the corresponding mRNA. Additionally, when used to refer to a DNA molecule, the coding/sense strand can also include additional elements not found in the mRNA including, but not limited to promoters, enhancers, and introns. Similarly, the terms "template strand" and "antisense strand" are used interchangeably and refer to a nucleic acid sequence that is complementary to the coding/sense strand.

The term "nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer at al. (1991) *Nucleic Acid Res* 19:5081; Ohtsuka at al. (1985) *J Biol Chem* 260: 2605-2608; Rossolini et al. (1994) *Mol Cell Probes* 8:91-98). The terms "nucleic acid" or "nucleic acid sequence" can also be used interchangeably with gene, open reading frame (ORF), cDNA, and mRNA encoded by a gene.

The term "RNA" refers to a molecule comprising at least one ribonucleotide residue. By "ribonucleotide" is meant a nucleotide with a hydroxyl group at the 2' position of a β-D-ribofuranose moiety. The terms encompass double stranded RNA, single stranded RNA, RNAs with both double stranded and single stranded regions, isolated RNA such as partially purified RNA, essentially pure RNA, synthetic RNA, recombinantly produced RNA, as well as altered RNA, or analog RNA, that differs from naturally occurring RNA by the addition, deletion, substitution, and/or alteration of one or more nucleotides. Such alterations can include addition of non-nucleotide material, such as to the end(s) of an siRNA or internally, for example at one or more nucleotides of the RNA. Nucleotides in the RNA molecules of the presently disclosed subject matter can also comprise non-standard nucleotides, such as non-naturally occurring nucleotides or chemically synthesized nucleotides or deoxynucleotides. These altered RNAs can be referred to as analogs or analogs of a naturally occurring RNA.

The terms "short hairpin RNA" and "shRNA" are used interchangeably and refer to any nucleic acid molecule capable of generating siRNA. A non-limiting example of the presently disclosed subject matter is shown in each of SEQ ID NOS: 1-11. In one embodiment, the shRNA comprises a polynucleotide having one or more loop structures and a stem comprising self complementary sense and antisense regions, wherein the antisense region comprises a sequence complementary to a region of a target nucleic acid molecule, and wherein the polynucleotide can be processed either in vivo or in vitro to generate an active siRNA capable of mediating RNAi. In another embodiment, retroviral vectors encode shRNA, which are processed intracellularly, to generate siRNA that silence the expression of a target gene, such as a gene encoding MAT II β subunit.

The terms "small interfering RNA", "short interfering RNA" and "siRNA" are used interchangeably and refer to any nucleic acid molecule capable of mediating RNA interference (RNAi) or gene silencing. See e.g., Bass, *Nature* 411:428-429, 2001; Elbashir et al., *Nature* 411:494-498, 2001a; and PCT International Publication Nos. WO 00/44895, WO 01/36646, WO 99/32619, WO 00/01846, WO 01/29058, WO 99/07409, and WO 00/44914. A non-limiting example of an siRNA molecule of the presently disclosed subject matter is shown in each of SEQ ID NOs: 12-15, wherein the siRNA comprises the sense and antisense regions (19 nucleotide sequences in lower case). In one embodiment, the siRNA comprises a double stranded polynucleotide molecule comprising complementary sense and antisense regions, wherein the antisense region comprises a sequence complementary to a region of a target nucleic acid molecule (for example, an mRNA encoding MAT II β subunit). In another embodiment, the siRNA comprises a single stranded polynucleotide having self-complementary sense and antisense regions, wherein the antisense region comprises a sequence complementary to a region of a target nucleic acid molecule. As used herein, siRNA molecules need not be limited to those molecules containing only RNA, but further encompass chemically modified nucleotides and non-nucleotides.

The terms "microRNA" and "miRNA" refer are used interchangeably and refer to synthetic or single-stranded RNA molecules of 21-23 nucleotides in length, which regulate gene expression. The terms "miRNA" and "non-coding RNA" can be used interchangeably. Primary transcript (pri-miRNA) is processed to give rise to short-stem-loop pre-miRNA, which are further processed to produce miRNA, which are single-stranded RNA molecules of 21-23 nucleotides. The miRNA are partially complementary to one or several mRNA transcripts, and they downregulate expression of genes encoded by the transcripts with which they interact. Thus, synthetic miRNA that interact with MAT II β mRNA can be generated and used to effect the downregulation of MAT II β expression thereby inhibiting MAT II β protein expression and consequently MAT II activity and SAM synthesis under physiologic L-Met concentrations.

The term "Ribozyme", also known as "RNA enzyme" or "catalytic RNA" refers to ribonucleotides or RNA molecules that can act as enzymes that catalyze covalent changes in the structure of RNA molecules and that can cleave the target RNA molecule. Synthetic hammerhead ribozymes can be generated that recognize and cleave MAT Il β RNA, thereby inhibiting MAT II β protein expression and consequently MAT II activity and SAM synthesis under physiologic L-Met concentrations.

Synthetic ribozymes can be generated by placing the sequence of a hammerhead or hairpin ribozyme in the middle to an MAT II β antisense sequence, to target the consensus cleavage site, e.g. GUC or CUC, provided that the flanking sequences allow the creation of antisense sequences on both sides. These synthetic ribozymes can be screened to identify those that can function in vivo to affect the downregulation of MAT II β expression, thereby inhibiting MAT II β protein expression and consequently MAT II activity and SAM synthesis under physiologic L-Met concentrations.

IV. Sequence Similarity and Identity

The terms "identical" or percent "identity" in the context of two or more nucleotide or polypeptide sequences refer to two or more sequences or subsequences that are the same or have a specified percentage of amino acid residues or nucleotides that are the same, when compared and aligned for maximum correspondence, as measured using one of the sequence comparison algorithms disclosed herein or by visual inspection.

The term "substantially identical", in the context of two nucleotide sequences, refers to two or more sequences or subsequences that have in some embodiments at least 60%, in some embodiments about 70%, in some embodiments about 80%, in some embodiments about 90%, in some embodiments about 95%, in some embodiments, about 97%, and in some embodiments about 99% nucleotide identity, when compared and aligned for maximum correspondence, as measured using one of the following sequence comparison algorithms (described herein below) or by visual inspection. In some embodiments, the substantial identity exists in nucleotide sequences of at least 50 residues, in some embodiments in nucleotide sequence of at least about 100 residues, in some embodiments in nucleotide sequences of at least about 150 residues, and in some embodiments in nucleotide sequences comprising complete coding sequences.

In one aspect, polymorphic sequences can be substantially identical sequences. The terms "polymorphic", "polymorphism", and "polymorphic variants" refer to the occurrence of two or more genetically determined alternative sequences or alleles in a population. An allelic difference can be as small as one base pair. As used herein in regards to a nucleotide or polypeptide sequence, the term "substantially identical" also refers to a particular sequence that varies from another sequence by one or more deletions, substitutions, or additions, the net effect of which is to retain biological activity of a gene, gene product, or sequence of interest.

For sequence comparison, typically one sequence acts as a reference sequence to which test sequences are compared. When using a sequence comparison algorithm, test and reference sequences are entered into a computer program, subsequence coordinates are designated if necessary, and sequence algorithm program parameters are selected. The sequence comparison algorithm then calculates the percent sequence identity for the designated test sequence(s) relative to the reference sequence, based on the selected program parameters.

Optimal alignment of sequences for comparison can be conducted, e.g., by the local homology algorithm of Smith & Waterman, 1981, by the homology alignment algorithm of Needleman & Wunsch, 1970, by the search for similarity method for Pearson & Lipman, 1988, by computerized implementations of these algorithms (GAP, BESTFIT, FASTA, and TFASTA, in the Wisconsin Genetics Software Package, available from Accelrys Inc., San Diego, Calif., United States of America), or by visual inspection. See generally, Ausubel, 1995.

In some embodiments, an algorithm for determining percent sequence identity and sequence similarity is the BLAST algorithm, which is described by Altschul et al., 1990. Software for performing BLAST analyses is publicly available through the website of the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength W=11, an expectation E=10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See Henikoff & Henikoff, 1992.

In addition to calculating percent sequence identity, the BLAST algorithm also performs a statistical analysis of the similarity between two sequences. See e.g., Karlin & Altschul, 1993. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is in some embodiments less than about 0.1, in some embodiments less than about 0.01, and in some embodiments less than about 0.001.

Another indication that two nucleotide sequences are substantially identical is that the two molecules specifically or substantially hybridize to each other under stringent conditions. In the context of nucleic acid hybridization, two nucleic acid sequences being compared can be designated a "probe" and a "target". A "probe" is a reference nucleic acid molecule, and a "target" is a test nucleic acid molecule, often found within a heterogeneous population of nucleic acid molecules. A "target sequence" is synonymous with a "test sequence".

The phrase "hybridizing substantially to" refers to complementary hybridization between a probe nucleic acid molecule and a target nucleic acid molecule and embraces minor mismatches that can be accommodated by reducing the stringency of the hybridization media to achieve the desired hybridization.

"Stringent hybridization conditions" and "stringent hybridization wash conditions" in the context of nucleic acid hybridization experiments such as Southern and Northern blot analysis are both sequence- and environment-dependent. Longer sequences hybridize specifically at higher temperatures. An extensive guide to the hybridization of nucleic acids is found in Tijssen, 1993. Generally, highly stringent hybridization and wash conditions are selected to be about 5° C. lower than the thermal melting point (Tm) for the specific sequence at a defined ionic strength and pH. Typically, under "stringent conditions" a probe will hybridize specifically to its target subsequence, but to no other sequences.

The Tm is the temperature (under defined ionic strength and pH) at which 50% of the target sequence hybridizes to a perfectly matched probe. Very stringent conditions are selected to be equal to the Tm for a particular probe. An example of highly stringent hybridization conditions for Southern or Northern Blot analysis of complementary nucleic acids having more than about 100 complementary residues is overnight hybridization in 50% formamide with 1 mg of heparin at 42° C. An example of highly stringent wash conditions is 15 minutes in 0.1× standard saline citrate (SSC), 0.1% (w/v) SDS at 65° C. Another example of highly stringent wash conditions is 15 minutes in 0.2×SSC buffer at 65° C. (see Sambrook & Russell, 2001 for a description of SSC buffer and other stringency conditions). Often, a high stringency wash is preceded by a lower stringency wash to remove background probe signal. An example of medium stringency wash conditions for a duplex of more than about 100 nucleotides is 15 minutes in 1×SSC at 45° C. Another example of medium stringency wash for a duplex of more than about 100 nucleotides is 15 minutes in 4-6×SSC at 40° C. For short probes (e.g., about 10 to 50 nucleotides), stringent conditions typically involve salt concentrations of less than about 1M Na+ ion, typically about 0.01 to 1M Na+ ion concentration (or other salts) at pH 7.0-8.3, and the temperature is typically at least about 30° C. Stringent conditions can also be achieved with the addition of destabilizing agents such as formamide. In general, a signal to noise ratio of 2-fold or higher than that observed for an unrelated probe in the particular hybridization assay indicates detection of a specific hybridization.

The following are examples of hybridization and wash conditions that can be used to clone homologous nucleotide sequences that are substantially identical to reference nucleotide sequences of the presently disclosed subject matter: a probe nucleotide sequence hybridizes in one example to a target nucleotide sequence in 7% sodium dodecyl sulfate (SDS), 0.5M $NaPO_4$, 1 mm EDTA at 50° C. followed by washing in 2×SSC, 0.1% SDS at 50° C.; in another example, a probe and target sequence hybridize in 7% sodium dodecyl sulfate (SDS), 0.5M $NaPO_4$, 1 mm EDTA at 50° C. followed by washing in 1×SSC, 0.1% SDS at 50° C.; in another example, a probe and target sequence hybridize in 7% sodium dodecyl sulfate (SDS), 0.5M $NaPO_4$, 1 mm EDTA at 50° C. followed by washing in 0.5×SSC, 0.1% SDS at 50° C.; in another example, a probe and target sequence hybridize in 7% sodium dodecyl sulfate (SDS), 0.5M $NaPO_4$, 1 mm EDTA at 50° C. followed by washing in 0.1×SSC, 0.1% SDS at 50° C.; in yet another example, a probe and target sequence hybridize in 7% sodium dodecyl sulfate (SDS), 0.5M $NaPO_4$, 1 mm EDTA at 50° C. followed by washing in 0.1×SSC, 0.1% SDS at 65° C.

The term "similarity" is contrasted with the term "identity". Similarity is defined as above; "identity", however, means a nucleic acid or amino acid sequence having the same amino acid at the same relative position in a given family member of a gene family. Homology and similarity are generally viewed as broader terms than the term identity. Biochemically similar amino acids, for example leucine and isoleucine or glutamate/aspartate, can be present at the same position—these are not identical per se, but are biochemically "similar." As disclosed herein, these are referred to as conservative differences or conservative substitutions. This differs from a conservative mutation at the DNA level, which changes the nucleotide sequence without making a change in the encoded amino acid, e.g. TCC to TCA, both of which encode serine.

As used herein, DNA analog sequences are "substantially identical" to specific DNA sequences disclosed herein if: (a) the DNA analog sequence is derived from coding regions of the nucleic acid sequence shown in any of SEQ ID NOs:1-20 and odd numbered SEQ ID NOs: 21-30; or (b) the DNA analog sequence is capable of hybridization of DNA sequences of (a) under stringent conditions and which encode a biologically active gene product of the nucleic acid sequence shown in any of SEQ ID NOs:1-20 and odd numbered SEQ ID NOs: 21-30; or (c) the DNA sequences are degenerate as a result of alternative genetic code to the DNA analog sequences defined in (a) and/or (b). Substantially identical analog proteins will be greater than about 60% identical to the corresponding sequence of the native protein. Sequences having lesser degrees of identity but comparable biological activity are considered to be equivalents.

Nucleotide sequences are "substantially identical" where they have between about 70% and about 80% or more preferably, between about 81% and about 90%, or even more preferably, between about 91% and about 99%, sequence identity for nucleic acid residues which are identical to the nucleotide sequence of a MAT II, MAT II α2 or MAT II β subunit gene.

Peptide sequences which have about 35%, or 45%, or preferably from 45-55%, or more preferably 55-65%, or most preferably 65% or greater, or more preferably about 70%, or more preferably about 80%; or more preferably, between about 81% and about 90%; or even more preferably, between about 91% and about 99% (e.g., 91%, 92%, 93%, 94%, and 95%) amino acids which are identical or functionally equivalent or biologically functionally equivalent to the amino acids of a MAT II, MAT II α2 or MAT II β subunit polypeptide will be sequences which are "substantially similar".

The term "homology" describes a mathematically based comparison of sequence similarities which is used to identify genes or proteins with similar functions or motifs. Accordingly, the term "homology" is synonymous with the term "similarity" and "percent similarity" as defined above. Thus, the phrases "substantial homology" or "substantial similarity" have similar meanings.

In certain embodiments, the presently disclosed subject matter concerns the use of MAT II, MAT II α2 or MAT II β subunit genes and gene products that include within their respective sequences a sequence which is essentially that of a MAT II, MAT II α2 or MAT II β subunit gene, or the corresponding protein. The presently disclosed subject matter also includes the use of shRNA, siRNA and miRNA molecules, as well as synthetic hammerhead ribozymes, capable of suppressing and/or inhibiting expression of MAT II β subunit genes and gene products that include within their respective sequences a sequence which is essentially that of a MAT II β subunit gene, or the corresponding protein. The term "a sequence essentially as that of a MAT II β subunit gene", means that the sequence substantially corresponds to a portion of a MAT II β subunit or MAT II β subunit gene and has relatively few bases or amino acids (whether DNA or protein) which are not identical to those of a MAT II β subunit protein or MAT II β subunit gene, (or a biologically functional equivalent of, when referring to proteins). The term "biologically functional equivalent" is well understood in the art and is further defined in detail herein. Accordingly, sequences which have between about 70% and about 80%; or more preferably, between about 81% and about 90%; or even more preferably, between about 91% and about 99% (e.g., 91%, 92%, 93%, 94%, and 95%); of amino acids which are identical or functionally equivalent to the amino acids of a MAT II β subunit polypeptide (even numbered SEQ ID NOs: 22-30) or of nucleotides of MAT II β subunit gene (odd numbered SEQ ID NOs: 21-30), or of nucleotides of an shRNA (SEQ ID NOs: 1-11) or siRNA (SEQ ID NOs: 12-15) molecule directed to MAT II β subunit gene, will be sequences which are "essentially the same".

MAT II, MAT II α2 or MAT II β subunit (even numbered SEQ ID NOs: 22-30) gene products and MAT II, MAT II α2 or MAT II β subunit-encoding (odd numbered SEQ ID NOs: 21-30) nucleic acid sequences which have functionally equivalent codons are also covered by the presently disclosed subject matter. The term "functionally equivalent codon" is used herein to refer to codons that encode the same amino acid, such as the six codons for arginine or serine. Thus, when referring to the sequence examples presented in SEQ ID NOs: 21-30, applicants provide substitution of functionally equivalent codons of Table 1 into the sequences. Thus, applicants are in possession of amino acid and nucleic acids sequences which include such substitutions but which are not set forth herein in their entirety for convenience.

Alternatively, functionally equivalent proteins or peptides can be created via the application of recombinant DNA technology, in which changes in the protein structure can be engineered, based on considerations of the properties of the amino acids being exchanged. Changes designed by man can be introduced through the application of site-directed mutagenesis techniques, e.g., to introduce improvements to the antigenicity of the protein or to test MAT II β subunit mutants in order to examine MAT II β subunit activity, or other activity at the molecular level.

The term "functionally equivalent codon" is also used herein to refer to codons that encode biologically equivalent amino acids (see Table 1). Thus, when referring to the sequence examples presented in FIGS. 2 and 3 and SEQ ID NOs: 1-30 applicants provide substitution from Table 1 of codons that encode biologically equivalent amino acids as described herein into the sequence examples. Thus, applicants are in possession of amino acid and nucleic acids sequences which include such substitutions but which are not set forth herein in their entirety for convenience.

TABLE 1

Functionally Equivalent Codons.

| Amino Acids | | | Codons |
|---|---|---|---|
| Alanine | Ala | A | GCA GCC GCG GCU |
| Cysteine | Cys | C | UGC UGU |

TABLE 1-continued

Functionally Equivalent Codons.

| Amino Acids | | | Codons |
|---|---|---|---|
| Aspartic Acid | Asp | D | GAC GAU |
| Glumatic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | ACG AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It will also be understood that amino acid and nucleic acid sequences can include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences which may, for example, include various non-coding sequences flanking either of the 5' or 3' portions of the coding region or can include various internal sequences, i.e., introns, which are known to occur within genes.

The presently disclosed subject matter also encompasses the use of DNA segments which are complementary, or essentially complementary, to the sequences set forth in the specification. Nucleic acid sequences which are "complementary" are those which are base-pairing according to the standard Watson-Crick complementarity rules. As used herein, the term "complementary sequences" means nucleic acid sequences which are substantially complementary, as can be assessed by the same nucleotide comparison set forth above, or as defined as being capable of hybridizing to the nucleic acid segment in question under relatively stringent conditions such as those described herein. A particular example of a provided complementary nucleic acid segment is an antisense oligonucleotide.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1,000 mM, typically less than 500 mM, and preferably less than 200 mM. However, the combination of parameters is much more important than the measure of any single parameter. (See, e.g., Wetmur & Davidson, 1968).

Probe sequences can also hybridize specifically to duplex DNA under certain conditions to form triplex or other higher order DNA complexes. The preparation of such probes and suitable hybridization conditions are well known in the art.

As used herein, the term "DNA segment" refers to a DNA molecule which has been isolated free of total genomic DNA of a particular species. Furthermore, a DNA segment encoding a MAT II β subunit polypeptide refers to a DNA segment which contains MAT II β subunit coding sequences, yet is isolated away from, or purified free from, total genomic DNA of a source species, such as *Homo sapiens*. Included within the term "DNA segment" are DNA segments and smaller fragments of such segments, and also recombinant vectors, including, for example, plasmids, cosmids, phages, viruses, and the like.

Similarly, a DNA segment comprising an isolated or purified MAT II β subunit gene refers to a DNA segment including MAT II β subunit coding sequences isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences and cDNA sequences. "Isolated substantially away from other coding sequences" means that the gene of interest, in this case, the MAT II β subunit gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

Figures 3, 4:
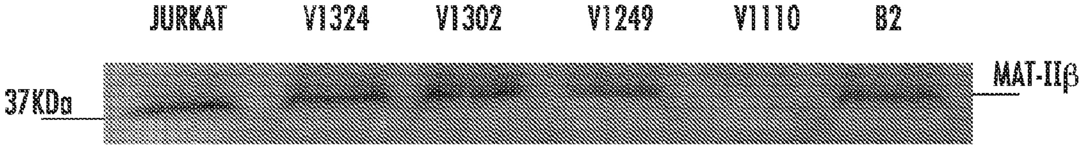
FIG. 3 depicts the design of MAT II β specific siRNA constructs (SEQ ID NOs: 12-15) used in the presently disclosed subject matter.
FIG. 4 is a digital image of a Western blot depicting the expression of MAT II β in Jurkat cells that were untransduced or transduced with HSPG empty virus (V1324), HSPG-mouse Plexin A1 (V1302), HSPG-MAT II β 1249 (V1249), HSPG-MAT II β 1110 (V1110) or HSPG-MAT II β β2 (β2). V1110 was most efficient in silencing MAT II β.
Figure 5A:
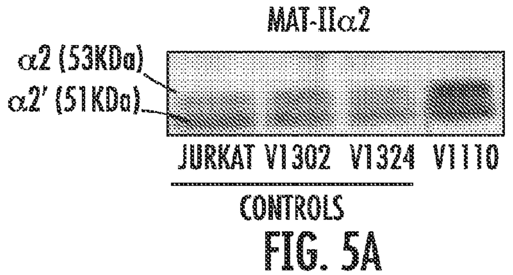
FIGS. 5A-5D depict the effects of shRNA on MAT II α2 and MAT II β protein expression and mRNA concentrations.
Figure 5B:
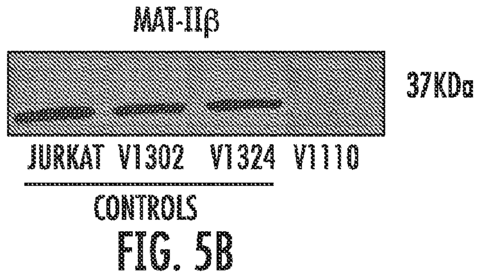
Figure 5C:
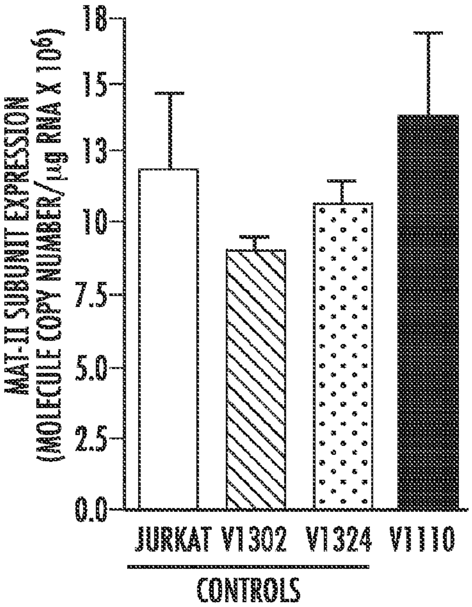
Figure 5D:
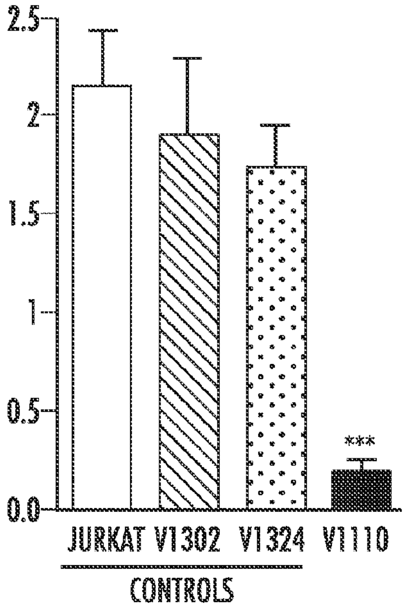

It will also be understood that the presently disclosed subject matter is not limited to the particular nucleic acid and amino acid sequences of FIGS. 2 and 3 and SEQ ID NOs: 1-30. Recombinant vectors and isolated DNA segments can therefore variously include the MAT II β subunit polypeptide-encoding region itself, or nucleic acids of shRNA, siRNA or miRNA molecules, or synthetic hammerhead ribozymes, as disclosed herein, include coding regions bearing selected alterations or modifications in the basic coding region, or include encoded larger polypeptides which nevertheless include MAT II β subunit, shRNA or siRNA shRNA, siRNA or miRNA molecules, or synthetic hammerhead ribozymes, that inhibit MAT II β expression or polypeptide-encoding regions or can encode biologically functional equivalent proteins or peptides which have variant amino acid sequences that interfere with the ability of MAT II β to interact with MAT II α protein.

The nucleic acid segments of the presently disclosed subject matter, regardless of the length of the coding sequence itself, can be combined with other RNA or DNA sequences, such as promoters, enhancers, polyadenylation signals, additional restriction enzyme sites, multiple cloning sites, other coding segments, and the like, such that their overall length can vary considerably. It is therefore provided that a nucleic acid fragment of almost any length can be employed, with the total length preferably being limited by the ease of preparation and use in the intended recombinant DNA protocol. For example, nucleic acid fragments can be prepared which include a short stretch complementary to a nucleic acid sequence set forth in any of FIGS. 2 and 3, such as about 10 nucleotides, and which are up to 10,000 or 5,000 base pairs in length, with segments of 3,000 being preferred in certain cases. DNA segments with total lengths of about 1,000, 500, 200, 100 and about 50 base pairs in length are also contemplated to be useful. Also, RNA sequences (siRNA, shRNA, miRNA) or ribozymes can be prepared which include antisense sequences that modulate MAT II β protein expression.

V. Modulation of MAT II

The presently disclosed subject matter takes advantage of RNAi technology (for example shRNA, siRNA and miRNA molecules and ribozymes) to cause the down regulation of cellular genes, a process referred to as RNA interference (RNAi). As used herein, "RNA interference" (RNAi) refers to a process of sequence-specific post-transcriptional gene silencing mediated by a small interfering RNA (siRNA) or short hairpin RNA (shRNA) molecules, miRNA molecules or synthetic hammerhead ribozymes. See generally Fire et al., *Nature* 391:806-811, 1998, and U.S. Pat. No. 6,506,559. The process of RNA interference (RNAi) mediated post-transcriptional gene silencing is thought to be an evolutionarily conserved cellular defense mechanism that has evolved to prevent the expression of foreign genes (Fire, *Trends Genet* 15:358-363, 1999).

RNAi might have evolved to protect cells and organisms against the production of double stranded RNA (dsRNA) molecules resulting from infection by certain viruses (particularly the double stranded RNA viruses or those viruses for which the life cycle includes a double stranded RNA intermediate) or the random integration of transposon elements into the host genome via a mechanism that specifically degrades single stranded RNA or viral genomic RNA homologous to the double stranded RNA species.

The presence of long dsRNAs in cells stimulates the activity of the enzyme Dicer, a ribonuclease III. Dicer catalyzes the degradation of dsRNA into short stretches of dsRNA referred to as small interfering RNAs (siRNA) (Bernstein et al., *Nature* 409:363-366, 2001). The small interfering RNAs that result from Dicer-mediated degradation are typically about 21-23 nucleotides in length and contain about 19 base pair duplexes. After degradation, the siRNA is incorporated into an endonuclease complex referred to as an RNA-induced silencing complex (RISC). The RISC is capable of mediating cleavage of single stranded RNA present within the cell that is complementary to the antisense strand of the siRNA duplex. According to Elbashir et al., cleavage of the target RNA occurs near the middle of the region of the single stranded RNA that is complementary to the antisense strand of the siRNA duplex (Elbashir et al., *Genes Dev* 15:188-200, 2001b).

RNAi has been described in several cell type and organisms. Fire et al., 1998 described RNAi in *C. elegans*. Wianny & Zernicka-Goetz, *Nature Cell Biol* 2:70-75, 1999 disclose RNAi mediated by dsRNA in mouse embryos. Hammond at al., *Nature* 404:293-296, 2000 were able to induce RNAi in *Drosophila* cells by transfecting dsRNA into these cells. Elbashir at al. *Nature* 411:494-498, 2001 a demonstrated the presence of RNAi in cultured mammalian cells including human embryonic kidney and HeLa cells by the introduction of duplexes of synthetic 21 nucleotide RNAs.

Other studies have indicated that a 5'-phosphate on the target-complementary strand of a siRNA duplex facilitate siRNA activity and that ATP is utilized to maintain the 5'-phosphate moiety on the siRNA (Nykanen et al., *Cell* 107: 309-321, 2001). Other modifications that might be tolerated when introduced into an siRNA molecule include modifications of the sugar-phosphate backbone or the substitution of the nucleoside with at least one of a nitrogen or sulfur heteroatom (PCT International Publication Nos. WO 00/44914 and WO 01/68836) and certain nucleotide modifications that might inhibit the activation of double stranded RNA-dependent protein kinase (PKR), specifically 2'-amino or 2'-O-methyl nucleotides, and nucleotides containing a 2'-O or 4'-C methylene bridge (Canadian Patent Application No. 2,359, 180).

Other references disclosing the use of dsRNA and RNAi include PCT International Publication Nos. WO 01/75164 (in vitro RNAi system using cells from *Drosophila* and the use of specific siRNA molecules for certain functional genomic and certain therapeutic applications); WO 01/36646 (methods for inhibiting the expression of particular genes in mammalian cells using dsRNA molecules); WO 99/32619 (methods for introducing dsRNA molecules into cells for use in inhibiting gene expression); WO 01/92513 (methods for mediating gene suppression by using factors that enhance RNAi); WO 02/44321 (synthetic siRNA constructs); WO 00/63364 and WO 01/04313 (methods and compositions for inhibiting the function of polynucleotide sequences); and WO 02/055692 and WO 02/055693 (methods for inhibiting gene expression using RNAi).

In some embodiments, the presently disclosed subject matter utilizes RNAi to at least partially inhibit expression of one or more enzyme subunits of interest. Inhibition is preferably at least about 10% of normal expression amounts, or at least about 20% of normal expression amounts, or at least about 30% of normal expression amounts, or at least about 40% of normal expression amounts, or at least about 50% or more of normal expression amounts, or at least about 60% or more of normal expression amounts, or at least about 70% or more of normal expression amounts, or at least about 80% or more of normal expression amounts, or at least about 90% or more of normal expression amounts. In some embodiments, the method comprises introducing an RNA into at least one of a plurality of T or B cells or other relevant cancerours cells in an amount sufficient to inhibit expression of the MAT II β enzyme subunit, wherein the RNA comprises a ribonucleotide sequence which corresponds to a coding strand of a gene encoding the enzyme subunit. In some embodiments, the T or B cells or other relevant cancerours cells are present in an organism, preferably a mammal, and the RNA is introduced into the organism. As a non-limiting example, the gene can encode a human MAT II β subunit (a representative embodiment is disclosed in U.S. Pat. No. 6,696,279, incorporated herein in its entirety).

The RNA can have a double-stranded region comprising a first strand comprising a ribonucleotide sequence that corresponds to the coding strand of the gene encoding the MAT II β subunit and a second strand comprising a ribonucleotide sequence that is complementary to the first strand. The first strand and the second strand hybridize to each other to form the double-stranded molecule. The double stranded region can be at least 15 basepairs in length, and in some embodiments, between 15 and 50 basepairs in length, and in some embodiments the double stranded region is between 15 and 30 basepairs in length.

In some embodiments, the RNA comprises one strand that forms a double-stranded region by intramolecular self-hybridization, which is preferably complementary over at least 19 bases. In some embodiments, the RNA comprises two separate strands that form a double-stranded region by intermolecular hybridization that is complementary over at least 19 bases. By way of example and not limitation, RNAi (shRNA and siRNA) molecules of the presently disclosed subject matter include those having a nucleotide sequence of one of SEQ ID NOs: 1-15 (FIGS. 2 and 3).

One skilled in the art will recognize that any number of suitable common techniques can be used to introduce the RNAs into a T or B cells or other relevant cancerous cells. In some embodiments, a vector encoding the RNA is introduced into the one or more T or B cells or other relevant cancerous cells. For example, the vector encoding the RNA can be transfected into a T or B cells or other relevant cancerous cells and the RNA is then transcribed by cellular polymerases.

In some embodiments, a recombinant virus comprising nucleic acid encoding the RNA can be produced. Introducing the RNA into a T or B cells or other relevant cancerous cells then comprises infecting the T or B cells or other relevant cancerous cells with the recombinant virus such as a retrovirus. T or B cells or other relevant cancerous cells polymerases transcribe the RNA resulting in expression of the RNA within these cells. Engineering retroviral vectors is known to those having ordinary skill in the art. Such a skilled artisan would readily appreciate the multiple factors involved in selecting the appropriate virus and vector components needed to optimize recombinant virus production for use with the presently disclosed subject matter without the necessity of further detailed discussion herein. As one non-limiting example, a retrovirus can be engineered comprising DNA encoding an shRNA comprising an siRNA. The retrovirus can be engineered to be replication deficient such that T or B cells or other relevant cancerous cells can be infected by the recombinant retrovirus, the shRNA transcribed, and transiently expressed in the infected T or B cells or other relevant cancerous cells. Details of recombinant virus production and use can be found in U.S. Patent Application Publication No. 2006/0009402 and PCT International Patent Application Publication No. WO 03/006,477, herein incorporated by reference in their entireties.

In some embodiments, an shRNA molecule can comprise a sense region and an antisense region, wherein the antisense region comprises a nucleic acid sequence complementary to an RNA sequence encoding a MAT II β subunit and the sense region comprises a nucleic acid sequence complementary to the antisense region. The shRNA molecule can be assembled from the sense region and the antisense region of the shRNA molecule. In a representative embodiment, the sense region of an shRNA can comprises a contiguous 19-30 nucleotide subsequence of one of SEQ ID NOs. 1-11 and the antisense region comprises the reverse-complement of the sense region. The sense region and the antisense region can further comprise a 3'-terminal overhang, which is preferably 2 to 8 nucleotides in length. The 3'-terminal nucleotide overhang can further contain one or more chemically modified nucleotides.

In some embodiments, the sense region and the antisense region are covalently connected via a linker molecule. In some embodiments, the linker molecule is a polynucleotide linker, for example, a polynucleotide linker of from 5 to 9 nucleotides. In some embodiments, the linker molecule is a non-nucleotide linker.

In some embodiments, an siRNA of the presently disclosed subject matter can comprise a contiguous 19-30 nucleotide of one of SEQ ID NOs. 12-15. In some embodiments, siRNA directed to MAT II β subunit suppression can be generated by PCR using primers to amplify the region corresponding to +151 to +879 bp of the MAT II β subunit open reading frame (ORF) and then using the Dicer enzyme to generate siRNA. In some embodiments, the target sequence of MAT II β can be: CCUUAAAUAUUUGAGAGUC (SEQ ID NO: 16). In some embodiments, the forward primer can be (5'-CAGATCTAATAATTGGCATGCAGTTG; SEQ ID NO: 17), containing a 5' Bgl II site, and the reverse primer (5'-CAGGCCTAGCATTTCTCGGACGTTGT; SEQ ID NO: 18), containing a Stu I site, were used. The PCR product can be purified from the agarose gel with a gel extraction kit (Qiagen, Inc., Valencia, Calif., United States of America), ligated into pGEM T-easy vector (Promega Corp., Madison, Wis., United States of America), then transformed into competent *E. coli* strain DH5α. The white colonies can be selected from the transformation and grown overnight in LB broth. Plasmid preps can then be done on the cultures (Qiagen, Inc.). The eluted plasmid DNA can then be digested with EcoR I, and run on a agarose gel to determine the presence or absence of the insert.

After sequencing the positive plasmid preps the correct sequence can be removed from pGEM T-easy using Bgl II and Stu I. The vector pLITMUS 28i (Novagen, Inc., Gibbstown, N.J., United States of America) can then be prepared for ligation by digesting with Bgl II and Stu I, then treated with calf alkaline phosphatase. Linearized pLITMUS 28i and the MAT II β insert from pGEM T-easy can then be ligated overnight at 4° C., then transformed into *E. coli* strain DH5α. Once cloned, the plasmid can be linearized with either Bgl II or Stu I (Promega Corp.). Following linearization of the plasmid, an equal amount (5 μg) of each can be used in a T7 polymerase transcription reaction (RiboMax-Promega Corp.) at 37° C. for 4 hours to generate dsRNA. The dsRNA can be purified using RNA STAT-60 (Tel-Test, Inc., Friendswood, Tex., United States of America). To generate siRNA (21-22 nt), the dsRNA can be incubated at 37° C. with recombinant human Dicer enzyme (Genlantis, Inc., San Diego, Calif., United States of America) for 16 hours. The siRNA generated by the reaction can then be passed over 2 columns (Genlantis, Inc.) to remove salts and any remaining dsRNA greater than 25 bp.

In some embodiments control siRNA can be generated using two primers each contain a recognition sequence for the T7 polymerase. The sense primer (5'-GCGTAATACGACTCACTATAGGGAGAACCTCTTACCTCAGTTACAA; SEQ ID NO: 19) and the antisense primer (5'-GCGTAATACGACTCACTATAGGGCGTTGTAACTGAGGTAAGAGGTT; SEQ ID NO: 20) can be placed in a 5 cycle PCR reaction (95° C., 52° C., 72° C.) to fill in the T7 overhangs and generate a linear template for synthesis of dsRNA. The resulting PCR product can be precipitated, and 5-10 μg can be placed in a T7 polymerase transcription reaction (RiboMax-Promega Corp.) at 37° C. for 4 hours to produce dsRNA. RNase One (Promega Corp.) can then be used to remove the single stranded RNA overhangs. The resulting 23-25nt control siRNA can be cleaned up using RNA STAT-60 (Tel-Test, Inc.).

In some embodiments, a miRNA or a hammerhead ribozyme of the presently disclosed subject matter is generated to target specific sequences of the MAT II β mRNA to inhibit or cleave the mRNA and thus inhibit MAT IIβ expression.

As used herein, the terms "inhibit", "suppress", "down regulate", "knock down", and grammatical variants thereof are used interchangeably and refer to an activity whereby gene expression or a level of an RNA encoding one or more gene products is reduced below that observed in the absence of a composition of the presently disclosed subject matter. In one embodiment, inhibition with an siRNA, shRNA, miRNA molecule or a hammerhead ribozyme results in a decrease in the steady state level or cleavage of a target RNA. In another embodiment, inhibition with siRNA, shRNA, miRNA molecule or a hammerhead ribozyme results in an expression level of a target gene that is below that level observed in the presence of an inactive or attenuated molecule that is unable to mediate an RNAi response. In another embodiment, inhibition of gene expression with an siRNA, shRNA, miRNA molecule or a hammerhead ribozyme of the presently disclosed subject matter is greater in the presence of other siRNA molecule than in its absence. In still another embodiment, inhibition of gene expression is associated with an enhanced rate of degradation of the mRNA encoded by the gene (for example, by RNAi mediated by siRNA, shRNA, miRNA molecule or a hammerhead ribozyme).

In some embodiments, compositions and methods for modulating MAT II biological activity in cells, such as cancerous cells, for example leukemic cells or cancerous liver cells, is provided. In some embodiments, MAT II biological activity can be modulated by blocking or interfering with the interaction between the MAT II β subunit and the MAT II α2 subunit by providing a composition comprising a small molecule, an aptamer, a peptide, an antibody or any other compound or molecule capable of blocking or interfering with the interaction between the MAT II β subunit and the MAT II α2 subunit. Blocking or interfering with the interaction between the MAT II β subunit and the MAT II α2 subunit can substantially reduce the enzymatic activity of MAT II. Reduction of the enzymatic activity of MAT II is preferably at least about 10% of normal enzymatic activity, or at least about 20% of normal enzymatic activity, or at least about 30% of normal enzymatic activity, or at least about 40% of normal enzymatic activity, or at least about 50% or more of normal enzymatic activity, or at least about 60% or more of normal enzymatic activity, or at least about 70% or more of normal enzymatic activity, or at least about 80% or more of normal enzymatic activity, or at least about 90% or more of normal enzymatic activity. In some embodiments, the method comprises introducing a small molecule, an aptamer, a peptide, an antibody or any other compound or molecule capable of blocking or interfering with the interaction between the MAT II β subunit and the MAT II α2 subunit into at least one of a plurality of T or B cells or other relevant cancerours cells in an amount sufficient to reduce the enzymatic activity of MAT II. In some embodiments, the T or B cells or other relevant cancerours cells are present in an organism, preferably a mammal, and the small molecule, an aptamer, a peptide, an antibody or any other compound or molecule capable of blocking or interfering with the interaction between the MAT II β subunit and the MAT II α2 subunit is introduced into the organism. As a non-limiting example, the gene can encode a human MAT II β subunit (a representative embodiment is disclosed in U.S. Pat. No. 6,696,279, incorporated herein in its entirety).

VI. Introduction of Sequences

Where a gene or nucleotide sequence is employed to introduce a gene product or RNA, such as an siRNA, shRNA, miRNA molecule or a hammerhead ribozyme, a convenient method of introduction will be through the use of a recombinant vector which incorporates the desired nucleotide sequence, together with its associated control sequences. The preparation of recombinant vectors is well known to those of skill in the art and described in many references, such as, for example, Sambrook et al. (1989), specifically incorporated herein by reference.

In vectors, it is understood that the DNA coding sequences to be expressed, in this case those encoding siRNA, shRNA, miRNA molecules directed to the MAT II β subunit, or those encoding the MAT II β subunit gene products, are positioned adjacent to and under the control of a promoter. In accordance with the presently disclosed subject matter, it is understood in the art that to bring a coding sequence under the control of such a promoter, one generally positions the 5' end of the transcription initiation site of the transcriptional reading frame of the gene product to be expressed between about 1 and about 50 nucleotides "downstream" of (i.e., 3' of) the chosen promoter. One can also desire to incorporate into the transcriptional unit of the vector an appropriate polyadenylation site (e.g., 5'-AATAAA-3'), if one was not contained within the original inserted DNA. Typically, these poly A addition sites are placed about 30 to 2000 nucleotides "downstream" of the coding sequence at a position prior to transcription termination.

While use of the control sequences of the specific gene (i.e., a MAT II β shRNA or siRNA promoter as set forth in FIGS. 2 and 3) will be preferred, there is no reason why other control sequences could not be employed, so long as they are compatible with the genotype of the cell being treated. Thus, one can mention other useful promoters by way of example, including, e.g., an H1 promoter, an SV40 early promoter, a long terminal repeat promoter from retrovirus, an actin promoter, a heat shock promoter, a metallothionein promoter, and the like.

As is known in the art, a promoter is a region of a DNA molecule typically within about 100 nucleotide pairs in front of (upstream of) the point at which transcription begins (i.e., a transcription start site). That region typically contains several types of DNA sequence elements that are located in similar relative positions in different genes. As used herein, the term "promoter" includes what is referred to in the art as an upstream promoter region, a promoter region or a promoter of a generalized eukaryotic RNA Polymerase II transcription unit.

Another type of discrete transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from transcription start sites so long as a promoter is present.

As used herein, the phrase "enhancer-promoter" means a composite unit that contains both enhancer and promoter elements. An enhancer-promoter is operatively linked to a coding sequence that encodes at least one gene product. As used herein, the phrase "operatively linked" means that an enhancer-promoter is connected to a coding sequence in such a way that the transcription of that coding sequence is controlled and regulated by that enhancer-promoter. Approaches for operatively linking an enhancer-promoter to a coding sequence are well known in the art. As is also well known in the art, the precise orientation and location relative to a coding sequence whose transcription is controlled, is dependent inter alia upon the specific nature of the enhancer-promoter. Thus, a TATA box minimal promoter is typically located from about 25 to about 30 base pairs upstream of a transcription initiation site and an upstream promoter element is typically located from about 100 to about 200 base pairs upstream of a transcription initiation site. In contrast, an enhancer can be located downstream from the initiation site and can be at a considerable distance from that site.

An enhancer-promoter used in a vector construct of the presently disclosed subject matter can be any enhancer-promoter that drives expression in a cell to be transfected. By employing an enhancer-promoter with well-known properties, the level and pattern of gene product expression can be optimized.

Introduction of the desired gene through the use of a viral vector to carry the MAT II β subunit siRNA or shRNA sequence to efficiently infect the cells. These vectors will preferably be an adenoviral, a retroviral, a vaccinia viral vector, adeno-associated virus or Lenti virus. These vectors are preferred because they have been successfully used to deliver desired sequences to cells and tend to have a high infection efficiency. Suitable vector-MAT II β subunit siRNA or shRNA constructs are adapted for administration as pharmaceutical compositions, as described herein below.

Commonly used viral promoters for expression vectors are derived from polyoma, cytomegalovirus, Adenovirus 2, and Simian Virus 40 (SV40). The early and late promoters of SV40 virus are particularly useful because both are obtained easily from the virus as a fragment which also contains the SV40 viral origin of replication. Smaller or larger SV40 fragments can also be used, provided there is included the approximately 250 by sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

The origin of replication can be provided either by construction of the vector to include an exogenous origin, such as can be derived from SV40 or other viral (e.g., Polyoma, Adeno, VSV, BPV) source, or can be provided by the host cell chromosomal replication mechanism. If the vector is integrated into the host cell chromosome, the latter is often sufficient.

In some embodiments, a retroviral vector with an shRNA or siRNA disclosed herein can be generated using a pHTP vector as a template in a PCR reaction to add a H1 RNA pol III site to the MAT II β shRNA or siRNA. The forward primer (5'-GCGATATCCCGCGGAATTCGAACGCTGAC; SEQ ID NO: 17) can be the same in all reactions, and can contain a EcoR V site for cloning. In some embodiments the reverse primers can contain 19 by sense and antisense regions corresponding to separate, but specific regions of the MAT II β ORF, and a Xba I site to be used for cloning (FIG. 2).

Following the PCR reaction, the 299 by product can be purified from the gel (Qiagen, Inc.), ligated into the pGEM T-easy vector (Promega Corp.), and transformed into *E. coli* strain DH5α. Positive, white, colonies can be selected and grown overnight in LB broth. Plasmid preps can be performed on the cultures (Qiagen, Inc.). A digestion of the preps can be carried out using EcoR I, and preps containing the insert can be sequenced. The retroviral vector pHSPG can then be prepared by restriction digest with EcoR V and Xba I, followed by calf alkaline phosphatase treatment of the digested vector. The insert can removed from pGEM T-easy, ligated into pHSPG, and transformed into *E. coli* strain DH5α.

For introduction of, for example, a MAT II β siRNA, shRNA, miRNA molecule or a hammerhead ribozyme, it is proposed that one will desire to preferably employ a vector construct that will deliver the desired gene to the affected cells. This will, of course, generally require that the construct be delivered to the targeted cells, for example, T cells, B cells, lymphocytes, leukemic lymphocytes or cancer cells. It is proposed that this can be achieved most preferably by conjugating the RNAi construct to a carrier such as an antibody or encapsulating it into a nanoparticle that directs the RNAi construct to the target cancer cells in vitro or in vivo. It is also proposed that this can be achieved most preferably by introduction of the desired gene through the use of a viral vector to carry the MAT II β subunit siRNA or shRNA sequence to efficiently infect the cells. These vectors can optionally be an adenoviral, a retroviral, a vaccinia viral vector, adeno-associated virus or Lenti virus. These vectors can be desirable because they have been successfully used to deliver desired sequences to cells and tend to have a high infection efficiency. Suitable vector-MAT II β subunit siRNA or shRNA constructs can be adapted for administration as pharmaceutical compositions, as described herein below.

Commonly used viral promoters for expression vectors are derived from polyoma, cytomegalovirus, Adenovirus 2, and Simian Virus 40 (SV40). The early and late promoters of SV40 virus are particularly useful because both are obtained easily from the virus as a fragment which also contains the SV40 viral origin of replication. Smaller or larger SV40 fragments can also be used, provided there is included the approximately 250 by sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

The origin of replication can be provided either by construction of the vector to include an exogenous origin, such as can be derived from SV40 or other viral (e.g., Polyoma, Adeno, VSV, BPV) source, or can be provided by the host cell chromosomal replication mechanism. If the vector is integrated into the host cell chromosome, the latter is often sufficient.

In some embodiments, a retroviral vector with an shRNA or siRNA disclosed herein can be generated using a pHTP vector as a template in a PCR reaction to add a H1 RNA pol III site to the MAT II β shRNA or siRNA. The forward primer (5'-GCGATATCCCGCGGAATTCGAACGCTGAC; SEQ ID NO: 17) can be the same in all reactions, and can contain a EcoR V site for cloning. In some embodiments the reverse primers can contain 19 by sense and antisense regions corresponding to separate, but specific regions of the MAT II β ORF, and a Xba I site to be used for cloning (FIGS. 2 and 3).

VII. Pharmaceutical Compositions

A "therapeutic composition" or a "pharmaceutical composition" as described herein preferably comprises a composition that includes a pharmaceutically acceptable carrier. In a preferred embodiment, the presently disclosed subject matter provides pharmaceutical compositions comprising a polypeptide or polynucleotide of the present presently disclosed subject matter and a physiologically acceptable carrier. More preferably, a pharmaceutical composition comprises siRNA, shRNA, miRNA molecule or a hammerhead ribozyme directed to MAT II β. subunit. In some embodiments, RNAi constructs will be conjugated to a carrier, for example a nanoparticle or an antibody to direct its delivery to the target cancer cells. The carrier (e.g. nanoparticle) conjugated to the RNAi can be injected in an acceptable pharmaceutical diluent. In some embodiments, an shRNA or siRNA is delivered to a target cell by a delivery vehicle, such as but not limited to a viral vector, an antibody, an aptamer, or a nanoparticle.

A composition of the presently disclosed subject matter is typically administered parenterally in dosage unit formulations containing standard, well-known nontoxic physiologically acceptable carriers, adjuvants, and vehicles as desired. The term "parenteral" as used herein includes intravenous, intra-muscular, intra-arterial injection, or infusion techniques.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Preferred carriers include neutral saline solutions buffered with phosphate, lactate, Tris, and the like. Of course, one purifies the vector sufficiently to render it essentially free of undesirable contaminants, such as defective interfering adenovirus particles or endotoxins and other pyrogens such that it does not cause any untoward reactions in the individual receiving the vector construct. A preferred means of purifying the vector involves the use of buoyant density gradients, such as cesium chloride gradient centrifugation.

A transfected cell can also serve as a carrier. By way of example, a liver cell can be removed from an organism, transfected with a polynucleotide of the presently disclosed subject matter using methods set forth above and then the transfected cell returned to the organism (e.g. injected intravascularly).

VIII. Therapeutic Methods

As used herein, the terms "MAT II β subunit activity" and "MAT II β subunit biological activity" are meant to be synonymous and are meant to refer to any biological activity of a MAT II β subunit polypeptide. Exemplary biological activities of MAT II β subunit comprise activity in the modulation of MAT II biological activity, modulation of levels of SAM, and modulation of cell growth, proliferation and/or differentiation, or other biological activity in accordance with the presently disclosed subject matter.

In accordance with the presently disclosed subject matter, administration of an siRNA or shRNA directed to MAT II β subunit to a subject can modulate MAT II β subunit activity. Modulation of MAT II β subunit activity can consequently modulate MAT II activity given that the MAT II β subunit is believed regulate MAT II. In some embodiments, expression of MAT II β subunit is inhibited or suppressed upon administration of a siRNA or shRNA in accordance with the present disclosure. Indeed, inhibition or suppression of the MAT II β subunit gene can result in substantially reduced concentrations of MAT II β subunit polypeptide, which consequently depresses MAT II activity. Upon suppression of MAT II activity, synthesis of SAM can be reduced.

In some embodiments, the siRNA or shRNA molecules of SEQ ID NOs: 1-15 can be administered to a subject to suppress MAT II β subunit expression. Of course, other siRNA and/or shRNA molecules can be generated by one of ordinary skill in the art to suppress MAT II β subunit gene expression and are within the scope of the present disclosure.

In some embodiments, in vitro optimization steps can be designed to (i) select the most efficient, specific and least toxic RNAi constructs; (ii) optimize the ability of the carrier-RNAi constructs to penetrate cell membranes; (iii) protect the construct from degradation by exonucleases within cells; (iv) direct intracellular trafficking of constructs to the appropriate cell compartment for efficient gene silencing; and (v) ensure correct folding of RNAi constructs in the cell, particularly if fused to a carrier (e.g. nanoparticle, see, e.g., FIG. 13).

In some embodiments, in vitro parameters can be extensively tested and optimized before embarking on in vivo testing, first in animal models, prior to clinical use. A main focus of a preclinical phase can be to ensure constructs are (i) protected when administered systemically; (ii) safely and specifically delivered in high quantities to their target cells for efficient MAT II β ablation; (iii) able to efficiently ablate MAT II β expression specifically in the target cancer cells; (iv) causing no or minimal systemic toxicity; (v) effectively induce apoptosis and diminish the growth of cancers cells; and (vi) cause no to minimal toxicity to the noncancerous cells.

When administered to a subject diagnosed with cancer, siRNA, shRNA, miRNA molecule or a hammerhead ribozyme directed to MAT II β subunit of the present disclosure can suppress SAM concentrations to a level where cancerous cells or tumor are no longer capable of surviving. Indeed, cancerous cells and tumors can require abnormally high SAM concentrations for cellular growth and survival. As disclosed in the Examples, the administration of siRNA or shRNA molecules directed to the MAT II β subunit to leukemic cells and/or subjects with leukemic cells resulted in a substantial reduction in SAM concentrations and consequently increased apoptosis and cell death in the leukemic cells.

Accordingly, in some embodiments, a substance, compound or therapeutic composition is administered to a subject to treat a cancer or other condition associated with MAT II activity or SAM metabolism. In some embodiments, the substance, compound or therapeutic composition comprises an siRNA or shRNA molecule of SEQ ID NOs: 1-15. In some embodiments, the subject has cancer, such as but not limited to leukemia. In some embodiments, administration of the substance, compound or therapeutic composition comprising an siRNA or shRNA molecule of SEQ ID NOs: 1-15 results in silencing of the MAT II β subunit gene in the subject, thereby decreasing MAT II activity and SAM synthesis, which results in treatment of the cancer, e.g. leukemia, or other condition. In some embodiments, the administration of the substance, compound or therapeutic composition has minimal or substantially no effect on non-cancerous cells or tissues.

In some embodiments, the presently disclosed subject matter provides compositions and methods for modulating MAT II biological activity in cells, such as cancerous cells, for example leukemic cells. In some embodiments, the methods comprise providing one or more cancerous cells, such as leukemic cells, the cancerous cells being in a subject such as a human; and contacting the cancerous cells with a composition comprising an RNA molecule comprising an siRNA or shRNA, the siRNA or shRNA modulating MAT II biological activity through RNAi induced down-regulation of MAT II β subunit expression, wherein the RNAi induced down-regulation of MAT II β subunit expression is mediated by suppressing the expression of a polynucleotide encoding a MAT II β subunit as set forth in SEQ ID NOs: 21, 23, 25, 27 and 29, whereby decreased MAT II biological activity suppresses cell growth and/or viability of the cancerous cells. In some embodiments, the compositions comprise an RNA molecule, such as an siRNA or shRNA molecule, capable of modulating MAT II β subunit expression in the cancerous cells. In some embodiments, the substance, compound or therapeutic composition comprises an siRNA or shRNA molecule of SEQ ID NOs: 1-15.

In some embodiments, a subject diagnosed with cancer is treated by administering: (i) a therapeutic composition comprising an siRNA or shRNA molecule of SEQ ID NOs: 1-15; and (ii) radiation therapy, chemotherapy, gene therapy, immunotherapy, a dietary treatment, or combinations thereof. In some embodiments, the dietary treatment comprises a dietary regimen designed to modulate plasma methionine levels. In some embodiments, a subject diagnosed with cancer is treated by administering: (i) a therapeutic composition comprising a combination of a plurality of the siRNA or shRNA molecules of SEQ ID NOs: 1-15, alone, or in combination with (ii) radiation therapy, chemotherapy, gene therapy, immunotherapy, a dietary treatment, or combinations thereof. In some embodiments, the subject has leukemia.

In some embodiments, preclinical testing can be used to combine the ablation of MAT II β with means to modulate systemic L-Met levels in a way that will protect the normal cells while further disadvantaging the survival of the cancerous cells. It is well documented that most tumors require much higher levels of L-Met than their normal counterparts. Restriction of dietary L-Met intake or the use or recombinant methioninase has been used in cancer therapy. Combining these treatments with methods to ablate MAT II β expression may improve therapeutic efficacy. Alternatively, L-Met levels can be modulated in a way to protect noncancerous cells that may have inadvertedaly taken up the therapeutic constructs.

In some embodiments, pre-clinical studies can also determine if the in vivo ablation of MAT II β expression can be combined with already approved chemotherapies in way that allow dose reduction and reduced toxicity commonly associated with anti-cancer chemical drug therapeutics.

IX. Subjects

With respect to the therapeutic methods of the presently disclosed subject matter, a preferred subject is a vertebrate subject. A preferred example of a vertebrate is a warm-blooded vertebrate. A preferred example of a warm-blooded vertebrate is a mammal. A preferred example of a mammal is a human. Additionally, as used herein and in the claims, the term "patient" can include both human and animal patients, and thus, veterinary therapeutic uses are contemplated in accordance with the presently disclosed subject matter.

Provided is the treatment of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also contemplated is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economical importance to humans. Thus, provided is the treatment of livestock, including, but not limited to, domesticated swine (pigs and hogs), ruminants, horses, poultry, and the like.

X. Dosage and Administration

In one embodiment, a therapeutic method according to the presently disclosed subject matter comprises administering to a subject a substance that inhibits or suppresses via RNAi MAT II β subunit gene expression and/or MAT II biological activity. Exemplary RNAi constructs of shRNA, siRNA miRNA molecules or hammerhead ribozymes capable of mediating inhibition of MAT II β subunit expression are disclosed herein as SEQ ID NOs: 1-15 (FIGS. 2 and 3). The method comprises treating a vertebrate subject suffering from a disorder associated with or mediated by MAT II β subunit biological activity, e.g., a tumor or cancer, such as leukemia, by administering to the patient an effective MAT II biological activity-modulating or MAT II β subunit gene expression-inhibiting amount of an RNAi construct molecule, delivered specifically to the cancer cells.

In some embodiments, delivery to a target cell, e.g., a cancer cell, can be achieved by employing a delivery vehicle, such as but not limited to a viral vector, an antibody, an aptamer or a nanoparticle. In some embodiments, the delivery vehicle comprises a modified nanoparticles. In accordance with the presently disclosed subject matter, coupling an RNAi construct to a nanoparticle, referred to herein as pRNA nanoparticles, provides for the successfully deliver siRNA in vivo to target cells, including cancer cells. In some embodiments, phi29 pRNA nanoparticles are used to successfully deliver siRNA in vivo to target cells, including cancer cells. I some embodiments, the pRNA nanoparticles, in addition to escorting the therapeutic moiety, also carries an antibody or a small portion of an antibody or an apatamer directed to surface receptors expressed specifically on the target cells and that allow efficient internalization of the RNAi-carrier construct.

It is to be appreciated that the potency, and therefore an expression of a "therapeutically effective" amount of a MAT II β subunit siRNA or shRNA molecule, and/or composition comprising the same, can vary. However, as shown by the present Examples, one skilled in the art can readily assess the potency of a candidate MAT II β subunit siRNA or shRNA molecule to inhibit MAT II β subunit gene expression and/or MAT II biological activity.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are provided.

EXAMPLES

The following Examples provide exemplary, non-limiting embodiments of the presently disclosed subject matter. In light of the present disclosure and the general level of skill in the art, those of skill will appreciate that the following Examples are intended to be exemplary only and that numerous changes, modifications, and alterations can be employed without departing from the scope of the presently claimed subject matter.

Example 1

Leukemic Cells

Jurkat T cells (E6-1; American Type Culture Collection, Rockville, Md., United States of America) were maintained in RPMI-1640 medium, supplemented with either 10% FBS or 1% HL-1 supplement (±L-Met), 2 mM L-glutamine, 50 ug/ml streptomycin, and 50 U/ml of penicillin.

Example 2

Generation of pHSPG-shRNA-Retrovirus

Several shRNA sequences were designed to target MAT II β expression and BLAST-searched these sequences against the human genome database to ensure their specificity for our target gene. The pHSPG plasmid (provided by Dr. Su at the University of North Carolina, Chapel Hill, N.C., United States of America) has a constitutively active pol III promoter in front of the multiple cloning site (MCS). pHSPG was modified by including a Histone 1 (H1) promoter needed for shRNA formation (Coffield et al., (2004) J Exp Med 200(10), 1315-1324), followed by shRNA constructs of interest between the EcoRV and XbaI sites, in the MCS. Downstream of this construct is a PGK-GFP cassette whose expression is driven by the MMTV promoter. The HSPG virus was chosen for its high transduction efficiency in hematopoetic cells (Taxman et al., (2006) BMC Biotechnol 6, 7; Wong et al., (2003) Nat Immunol 4(9), 891-898). The design of different MAT II β specific pHSPG-shRNA driven by the H1 promoter is shown in FIG. 2.

The effect of several control and MAT II β specific pHSGP-shRNA constructs on MAT II β expression were initially tested in transiently transfected Cos-1 cells. These studies showed that plasmid pHSGP-shRNA-1110 (SEQ ID NO: 6) had the highest gene silencing activity and was not toxic to the Cos-1 cells, and thus was packaged into HSPG-V1110 viral particles using HEK-293T cells and the $CaCl_2$ transfection method (Pear et al., (1993) Proc Natl Acad Sci USA 90(18), 8392-8396). An empty virus without shRNA (V1302) and V1324 that encodes an shRNA for an irrelevant, mouse Alexin Al, gene (Wong et al., (2003) Nat Immunol 4(9), 891-898) were also generated as controls.

Example 3

Transduction with HSPG-shRNA Retrovirus

Jurkat cells ($10^6$ cells) were transduced by adding 8 mg/ml polybrene plus 700 ml viral supernatants and incubating for 20 minutes at room temperature. The cells were spun at 2000 rpm for 3hours then re-suspended in fresh 1.5 ml RMPI-1640 complete medium. The cells were then cultured in 12-well tissue culture plates followed by a repeat transduction after 24 hours an d/or 48 hours. Transduction efficiency was subsequently assessed by flow cytometry (BD FACSCalibur™ System; BD Biosciences, San Jose, Calif., United States of America) to determine the percentage of GFP-positive cells. This procedure typically yielded >90% $GFP^+$ cells, which were then sorted using FACSAria (BD FACSAria™ Cell-Sorting System, BD Biosciences) to obtain a ≧98% transduced cell population.

Example 4

MAT II Subunits Expression Analysis $GFP^+$ sorted cells were lysed by 3 cycles of freeze-thawing in extraction buffer (50 mM Tris, pH 7.4, 50 mM NaCl, 5 mM $MgCl_2$, 4 mM dithiothreitol), containing a mixture of proteolytic inhibitors (Hoffmann-La Roche Inc., Nutley, N.J., United States of America) as described (De La Rosa et al., (1992) J Biol Chem 267(15), 10699-10704). Protein concentration was determined in the cleared lysates by the bicinchoninic acid method (Butron, K. (1956) Biochem. J. 62, 315-319). Equal amounts of protein extracts were separated on 10% SDS-PAGE then transblotted onto nitrocellulose papers. Expression of α2 and β subunits was determined by Western blots, probed with antibodies to MAT II α and MAT II β proteins (De La Rosa et al., (1992) Cancer Res 52, 3361-3366; Kotb et al., (1990) Biochim Biophys Acta 1040(2), 137-144).

Quantitative real-time PCR (Q-RT-PCR) was also used to assess MAT II α and MAT II β mRNA expression. cRNA standards were constructed for each subunit and standard curves were generated for each run to quantify mRNA copy number/2 μg total RNA. Briefly, *E. coli* strain JM109 was transformed with pTargeT/MAT II α subunit or pTargeT/MAT II β subunit (Halim et al., (1999) J Biol Chem 274(42), 29720-29725). The plasmids were purified using the WIZARD® PureFection DNA Purification System (Promega Corp., Madison, Wis., United States of America). Correct pTargeT/MAT II α and pTargeT/MAT II β plasmids were verified by sequencing, using a T7 promoter primer. T7 Ribomax™ large scale RNA production system (Promega Corp.) was used to generate MAT II α or MAT II β cRNA. The number of cRNA molecules were calculated as follows: $N(\text{molecules}/\mu l)=[C*182.5\times10^{13}]/K$, where C=cRNA μg/μl and K=bp (Fronhoffs et al., (2002) Mol Cell Probes 16(2), 99-110). For MAT II α cRNA: K=1188 by and C=0.658 μg/μl; for MAT II β cRNA: K=1050 by and C=0.632.

To test the efficiency of MAT II β silencing, RNA was extracted from $10^6$ untransduced or transduced cells using RNA-STAT 60™ (Tel-Test, Inc., Friendswood, Tex., United States of America), residual contaminating genomic DNA was removed by DNase I treatment (Qiagen, Inc., Valencia, Calif., United States of America), purified the RNA using Qiagen RNeasy kit (Qiagen, Inc.), then converted 2 μg of the purified RNA to cDNA using AMV reverse transcriptase, 10× random hexamers and 10 mM dNTP in the presence of RNase inhibitor (Promega Corp.). QRT-PCR reactions were run using the fluorogenic SYBR® Green RT-PCR system (Applied Biosystems, Inc., Foster City, Calif., United States of America) and the ABI PRISM® 7900 Sequence BioDetector (AME Bioscience A/S, Toroed, Norway). In each run, serial dilutions of MAT II α or MAT II β cRNA (104-1010 cRNA molecules/μl) were also converted to cDNA and used to generate the standard curve for each MAT II subunit. The PCR reaction mixture contained 25 μl of SYBR® Green PCR Master Mix (Applied Biosystems, Inc.), 2.5 μl containing 1.5-12 pmol of each primer, and 5 μl of the template cDNA in a final volume of 50 μl. The sequence of the MAT II β specific primers were (forward: 5'CACCTTACAGAGAGGAAGA3' (SEQ ID NO: 17) and reverse: 5'CAGTCACAGCACTTTCTTC3' (SEQ ID NO: 18). An 18S RNA primer mix (Qiagen, Inc.) was used for normalization. To calculate "N" for each test sample, the CT to the internal normalizer (18S) was first normalized, then the "N" from the standard curve was determined using the equation Y=[MX+C].

Example 5

Assay for MAT Activity

MAT activity was assayed in cell extracts as described previously (Kotb, M., and Kredich, N. M. (1985) J Biol Chem 260(7), 3923-3930). For kinetic analyses, different L-Met concentrations (1.25-80 μM) were used, using $^{14}C$-L-Met (57.9 mCi/mmol) and supplementing with cold L-Met. Reaction velocity is expressed as units (U)/mg protein; U=1 nmol of SAM/hr (Kotb, M., and Kredich, N. M. (1985) J Biol Chem 260(7), 3923-3930). Km and Vmax were calculated using the GraphPad PRISM® software (GraphPad Software, Inc., La Jolla, Calif., United States of America).

Example 6

Cell Growth at Different L-Met Concentrations

The cells were weaned to grow in serum-free RPMI-1640 media containing 1% HL-1 supplement (Cambrex Corp., East Rutheford, N.J., United States of America) plus 2 mM L-glutamine, 50 μg/ml streptomycin, and 50 U/ml of penicillin (RPMI-HL1s medium). Weaned cells ($10^6$/ml) were seeded in RPMI-HL1s medium at L-Met 5-100 μM, the media was replaced every 2 days, and the numbers of viable cells was recorded and then re-plated at $10^6$/ml for further analyses. Cell necrosis and apoptosis were determined by a flow cytometric quantification of propidium iodide and annexin-V (BD Bioscience) stained cells, respectively. In some studies, the cells were cultured at 10 μM L-Met for 3 days, harvested, counted and replated at $10^6$ cells/ml in fresh RPMI-HL1s medium with 10 μM L-Met. On day 6, cells were harvested, washed and replated in fresh media containing 20 μM or 50 μM L-Met. Cell growth/death were determined every 3 days thereafter, replating $10^6$ viable cells/ml each time.

Example 7

Measurement of SAMe Levels

SAMe levels were quantified in a neutralized 2N PCA acid-soluble extract by HPLC as previously detailed (De La Rosa et al., (1992) Cancer Res 52, 3361-3366). SAMe concentration (pmole/$10^6$ cells) was calculated from a standard curve using different concentrations of SAMe standard (USB), then converted the values to μM based on cell volume for Jurkat cells 0.76 ml/$10^9$ cells (De La Rosa et al., (1992) Cancer Res 52, 3361-3366).

Example 8

In Vivo Animal Studies

All animals were treated according to the Institutional Animal Care and Use Committee regulations, protocol #1587. Highly immune deficient NOD/ScidIL-2Rγnull mice were irradiated with 3.5GY, 24 hours prior to transplanting them via intraperitoneal (i.p.) injection of $15\times10^6$ V1110 (SEQ ID NO: 6) or V1302 Jurkat cells. Sera from mice was obtained 12 days post-injection then once a week thereafter to quantify levels of the surrogate tumor marker, soluble β2 microglobulin, using an ELISA β2 microglobulin kit (R&D Systems, Inc., Minneapolis, Minn., United States of America). At 4 and 5-weeks post-transplant, the transplanted mice were sacrificed (Table 2). FRI was used to image GFP fluorescence in spleen prior to extracting splenocytes and bone marrow cells to assess tumor growth and engraftment by counting % human CD3/GFP positive cells in each compartment by flow cytometry as detailed above.

TABLE 2

Engraftment of human $CD3^+/GFP^+$ cells in spleens and bone marrow of NOD/Scid IL-2R$\gamma^{null}$ mice

| | Week 4 | | | Week 5 | | |
|---|---|---|---|---|---|---|
| | V1302 | V1110 | P value | V1302 | V1110 | P value |
| Number of mice | 7 | 7 | | 8 | 8 | |
| Engraftment % | 57% | 0% | | 75% | 25% | |
| **Spleen** | | | | | | |
| $CD3^+/GFP^+$ % Mean ± SEM | 16 ± 7.6% | 1 ± 0.3% | 0.004 | 30 ± 9.8% | 1.1 ± 0.4% | 0.02 |
| $CD3^+/GFP^+$ % Median | 15% | 1% | | 29% | 1% | |
| **Bone Marrow** | | | | | | |
| $CD3^+/GFP^+$ % Mean ± SEM | 4 ± 1.6% | 0.8 ± 0.6% | 0.01 | 11 ± 3.6% | 2.4 ± 1% | 0.04 |
| $CD3^+/GFP^+$ % Median | 3% | 0.2% | | 11% | 0.95% | |

Example 9

Statistical Methods

Statistical significance was calculated with one way ANOVA and Newman-Keuls Multiple Comparison test for all the experiments except for the in vivo experiment where a Mann-Whitney test using the GraphPad PRISM® software (GraphPad Software, Inc.).

Example 10

Successful Ablation of MAT II β Expression

Several shRNA were designed to ablate MAT II β expression and were cloned into the retroviral plasmid pHSPG that expresses Green Fluorescent Protein (GFP). The HSPG-GFP plasmids were screened for their gene silencing efficiency and nonspecific toxicity. All MAT II β specific shRNA constructs were designed to target the two splice variants of MAT II β (Yang et al., (2008) Gastroenterology 134(1), 281-291). Initial screening was done in COS-1 cells and constructs with efficient gene silencing activity were then screened in Jurkat cells (FIG. 4). Construct V1110 (SEQ ID NO: 6) had the highest MAT II β silencing activity (FIG. 4) and least toxicity, and was thus packaged into infectious HSPG-GFP virus (Taxman et al., (2006) BMC Biotechnol 6, 7).

Jurkat cells were transduced with the various recombinant HSPG-shRNA viruses and were assessed for MAT II β ablation at the RNA and protein levels (FIGS. 4 and 5A-5D). Controls included cells infected with an empty virus (V1302) or with a virus encoding shRNA construct (V1324) directed to the mouse plexin A1 gene (Taxman et al., (2006) BMC Biotechnol 6, 7). Although transduction efficiencies for all cells tested were ≧90%, significant reduction or complete ablation of MAT II β RNA (FIG. 5D) and protein (FIG. 5B) expression was only seen in V1110-transduced cells. By contrast, expression of MAT II α2 was essentially unaffected (FIGS. 5A and 5C), thus verifying the MAT II β specificity of V1110. In some instances the expression of MAT II α2 was insignificantly elevated, perhaps reflecting an attempt to increase enzyme synthesis in order to compensate for the lack of MAT II β expression and increase SAMe synthesis.

Example 11

Figure 6A:
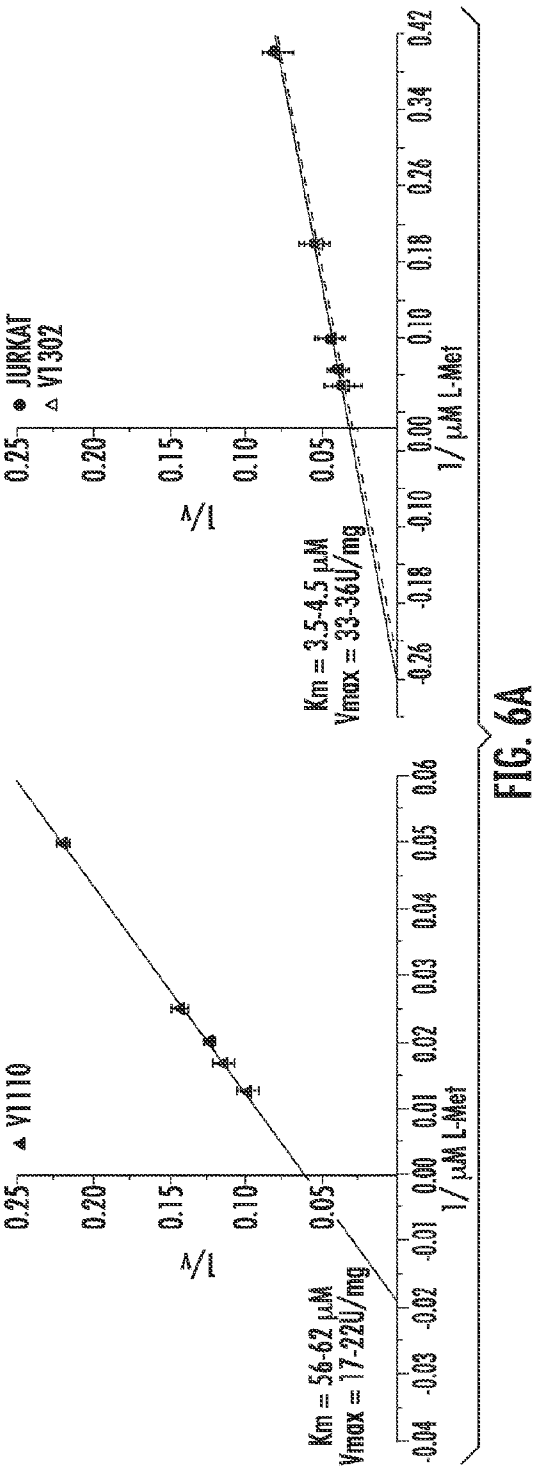
FIGS. 6A-6C are Lineweaver-Burk kinetic plots and bar graphs depicting the effects of MAT II β ablation on MAT II kinetics, specific activity and intracellular SAMe levels.
Figure 6B:
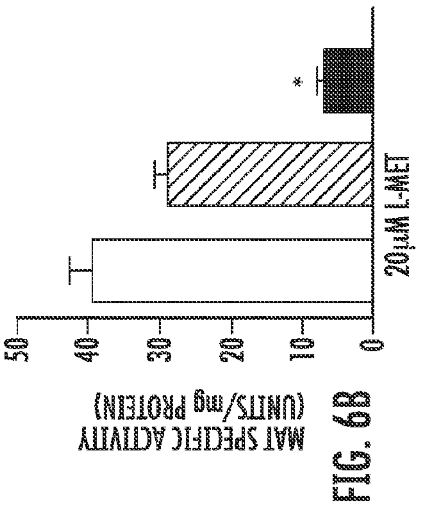

Effect of MAT II β Silencing on MAT II Activity, Kinetics, SAMe Pool Size and Cellular Growth Ablation of MAT II β expression altered MAT II $Km_{L\text{-}Met}$ and reduced SAMe pools in Jurkat cells. As predicted, the $Km_{L\text{-}Met}$ increased from 3.5-6 μM in untransduced and control virus-transduced Jurkat cells, up to 56-62 μM in V1110 cells (FIG. 6A). Further, at the high end of physiological L-Met levels (20 μM), MAT II specific activity was 4-5 fold lower in V1110 cells than in untransduced or control virus-transduced Jurkat cells, expressing MAT II β (FIG. 6B).

Figure 6C:
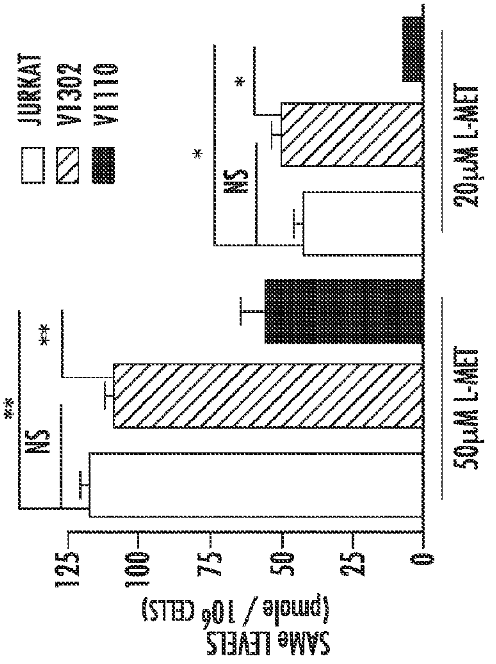

Importantly, in the absence of MAT II β, SAMe was undetectable in V1110 cells cultured at 10 μM L-Met (not shown), and even at 20 μM L-Met SAMe pool size was ~85% less than in untransduced or control-transduced V1302 cells (9.5±0.5 μM vs. 62±4 μM; p≦50.05), FIG. 6C. Significant 45-50% reductions in SAMe pool size (p≦0.01) were also found even when V1110 cells were maintained at 50 μM L-Met, which is ~2.5 fold higher than the upper range of physiological L-Met levels.

Figures 7A, 7B, 7C, 7D:
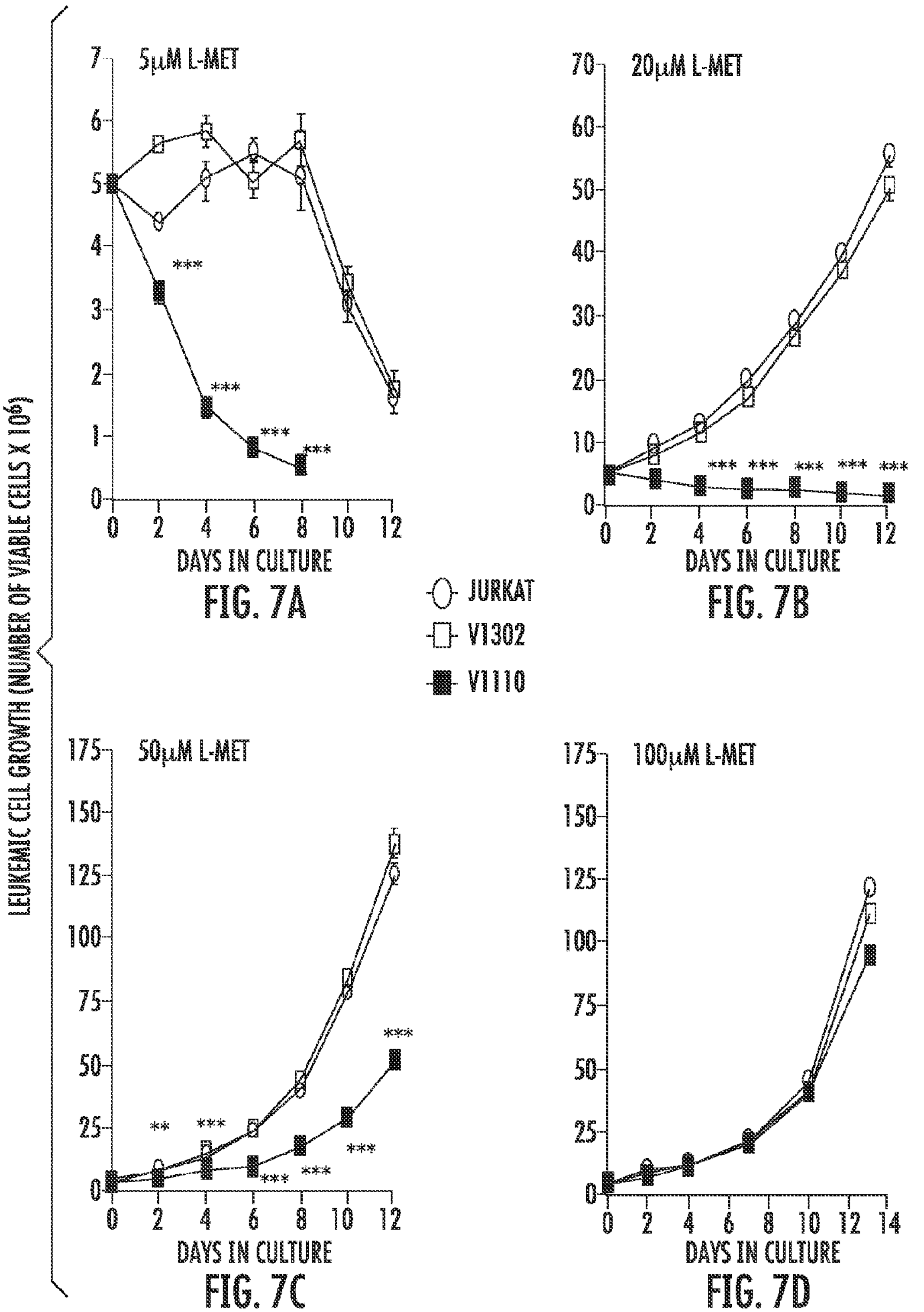
FIGS. 7A-7D are line graphs depicting the effects on MAT II β ablation on leukemic cell growth in plasma physiologic L-Met levels (5-20 μM) as well as unphysiologic levels (50-100 μM). Cells were seeded at $5\times10^6$ and exposed to 5 μM L-Met (FIG. 6A), 20 μM L-Met (FIG. 6B), 50 μM L-Met (FIG. 6C) and 100 μM L-Met (FIG. 6D) and monitored for growth every 2 days using the Trypan Blue exclusion method, adding fresh medium each time. Data are shown for untransduced (open circles), V1110- (solid squares) and V1302-transduced (open squares) cells. The growth of leukemic cells lacking MAT IIβ expression was significantly diminished under physiologic L-Met levels but was restored at unphysiologic 100 μM L-Met levels (*p≦0.05, p≦0.01, *p≦0.001).

The sharp reduction in SAMe pool size, as a consequence of MAT II β ablation, diminished the growth and viability of V1110 cells. At ≦20 μM L-Met, V1110 cells ceased to grow, and at 50 μM L-Met their growth was reduced by 33-36% compared to control-transduced V1302 cells (p<0.01), FIGS. 7B and 7C. By contrast, at 100 μM L-Met, V1110 cells grew at essentially the same rates and for the same duration in culture as the untransduced or control-transduced Jurkat cells (p>0.05, FIG. 7D). Thus, at unphysiologically high L-Met levels approaching MAT II α2 Km without MAT II β (i.e. Km=50-60 μM), V1110 leukemic cells appear to have satisfied their SAMe needs and grew normally. These results indicate that V1110 cells diminished growth at physiologic L-Met levels was a direct consequence of specific MAT II β silencing, which caused an upper shift in $Km_{L\text{-}Met}$ of MAT II and a significant reduction of SAMe synthesis and pools.

Example 12

Cell Death and Apoptosis of Leukemic Cells Lacking MAT II β

Significant reduction in growth rates of V1110 cells at physiological L-Met levels was associated with a significant increase in both cell necrosis and apoptosis (FIGS. 8A-8F). At physiologic L-Met levels (5, 10, and 20 μM) the extent of necrosis in the V1110 cells was significantly higher (20-55%) than in untransduced or control V1302 cells (p<0.001). Minimal cell death was seen at 50 μM L-Met; however, V1110 cells exhibited ~70-80% higher levels of apoptosis than the control leukemic cells even at this unphysiological L-Met concentration (p<0.01), FIGS. 8A-8F. This is likely attributed to the 50% reduction in SAMe pool size even at 50 μM L-Met (FIG. 6C). Taken together, these findings indicate that the growth and viability of V1110 cells, lacking MAT II β expression remained at a selective disadvantage, even at more than twice the higher end of physiological L-Met levels.

Example 13

Attempts to Rescue Cells by Incrementally Elevating L-Met Levels

Figures 8A, 8B, 8C, 8D, 8E, 8F:
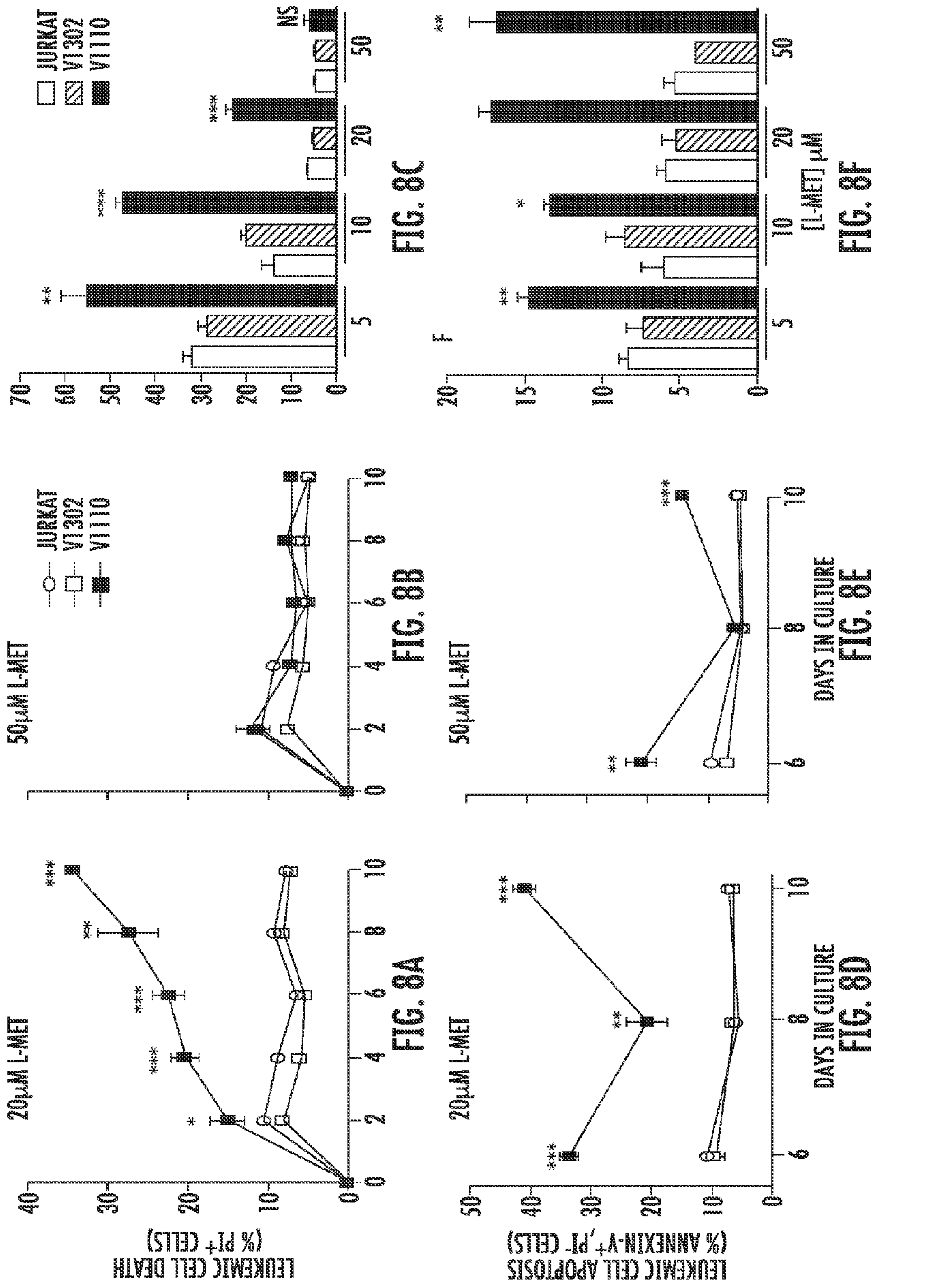
FIGS. 8A-8F are line graphs and bar graphs depicting the effects of MAT II β ablation on leukemic cell death and apoptosis in plasma physiologic L-Met levels (5-20 μM) as well as unphysiologic levels (50-100 μM). The figures show that MAT II β ablation induces high levels of apoptosis and necrosis of leukemic cells at physiologic L-Met levels (5-20 μM) and even at unphysiologically high, 50 μM L-Met.
Figure 9A:
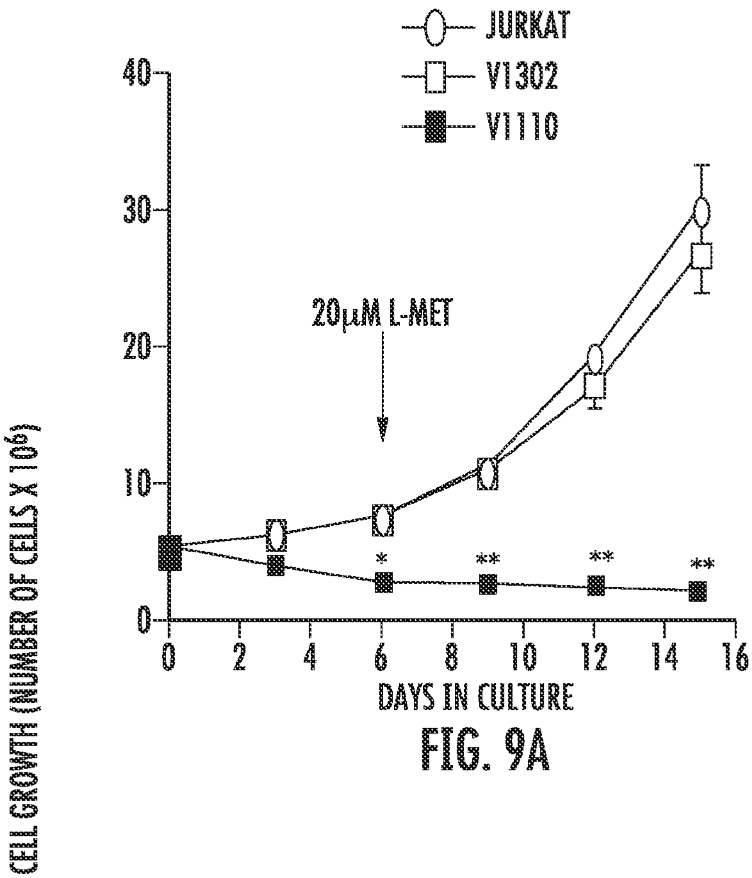
FIGS. 9A and 9B are line graphs depicting the results of attempts to rescue Jurkat cells±MAT II β expression by incrementally increasing L-Met levels in culture. Untransduced (open circles), V1110- (solid squares) and V1302-transduced (open squares) Jurkat cells ($5\times10^6$) were cultured at 10 μM L-Met for 6 days, then L-Met was raised to either 20 μM (FIG. 9A) or 50 μM (FIG. 9B). Viable cells were counted over 15 days, with addition of fresh media every 3 days. V1110 cells ceased to grow when L-Met was raised to 20 μM, and exhibited diminished growth even at 50 μM. *p≦0.05, p≦0.01, *p≦0.001.
Figure 9B:
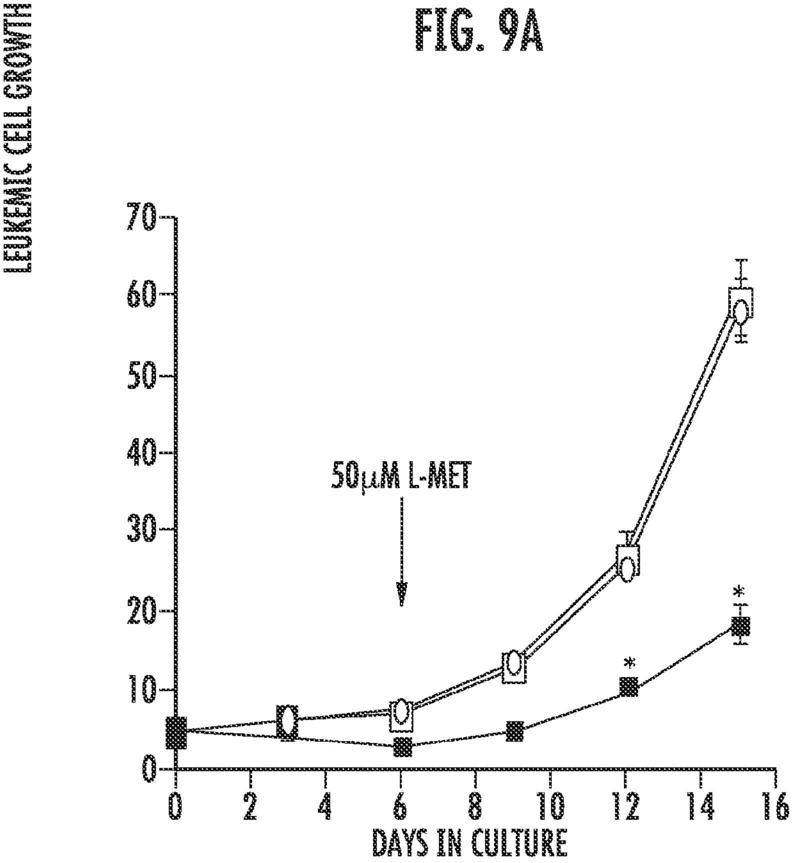

Following up on selective pressure imposed on the viability of MAT II β deficient Jurkat cells in physiologic L-Met conditions, we next tested whether V1110 cells can be rescued by incremental elevation of L-Met in culture. All cells grew at lower rates at the low end, 5-10 μM, of physiologic L-Met levels compared to ≧20 μM. Therefore, V1110 and control Jurkat cells were grown at 10 μM L-Met for 6 days in culture, followed by an increase in L-Met levels to either 20 or 50 μM to determine if these cells can be rescued (FIGS. 9A and 9B). The growth of control untransduced and control V1302 Jurkat cells increased by almost 80% and 90% when L-Met levels were raised to 20 or 50 μM, respectively. By contrast, under the same conditions, V1110 cells could not be rescued with 20 μM L-Met (p<0.01), and exhibited diminished growth even at 50 μM L-Met (p<0.05), FIGS. 9A and 9B). These data suggest that the initial insult to the V1110 cells, caused by low SAMe levels due to the absence of MAT II β, is irreversible at the high end of physiologic L-Met levels (20 μM) and minimally reversible at 50 μM L-Met. Failure to rescue V1110 cells is consistent with the above observed increased apoptosis of these cells, even at 50 μM L-Met (FIGS. 8E and 8F).

Example 14

Figure 10A:
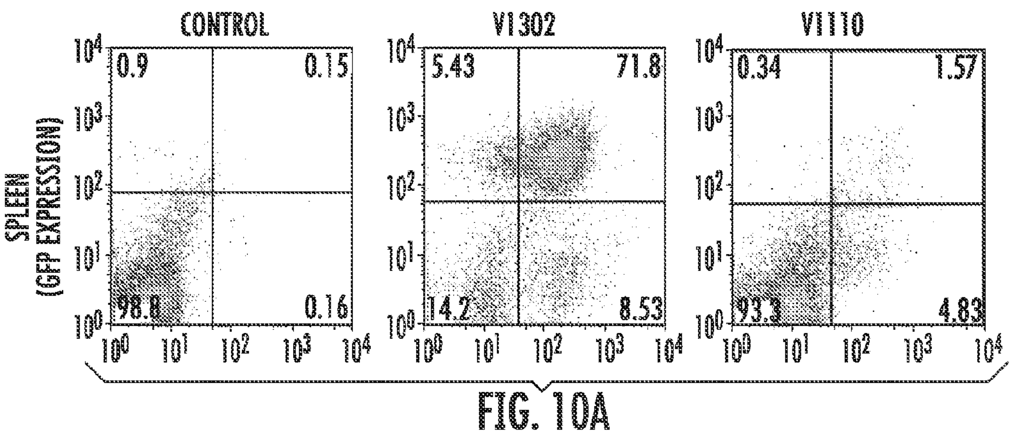
FIGS. 10A-10F show the effects of MAT II β ablation on leukemic cell growth in viva Hyper immune deficient NOD/Scid IL-2R$\gamma^{null}$ mice were irradiated with 3.5GY 24 hours prior to intraperitoneal (i.p.) transplant with $15\times10^6$ of the indicated cells. Controls included irradiated, but not injected mice and V1302 transplanted mice. Tumor engraftment and growth were monitored by measuring % human $CD3^+/GFP^+$ cells in mice spleens and bone marrow at 4 and 5 weeks post-transplant with either control V1302 or V1110 cells.
Figure 10B:
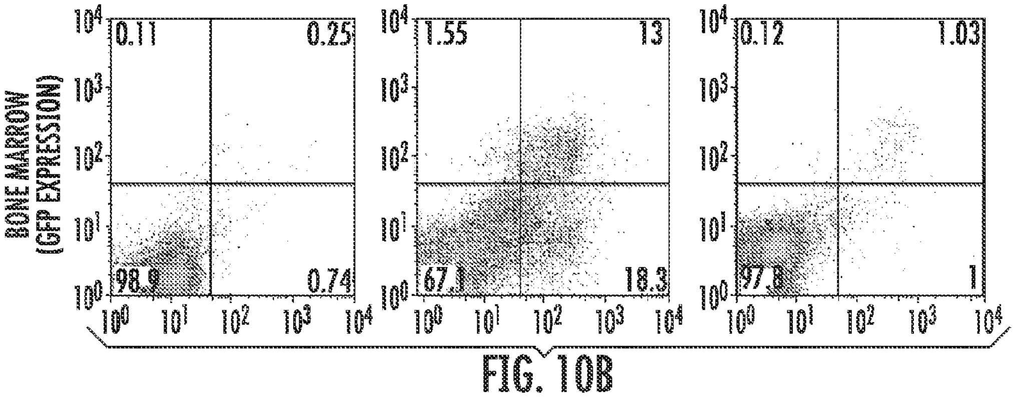
Figure 10C:
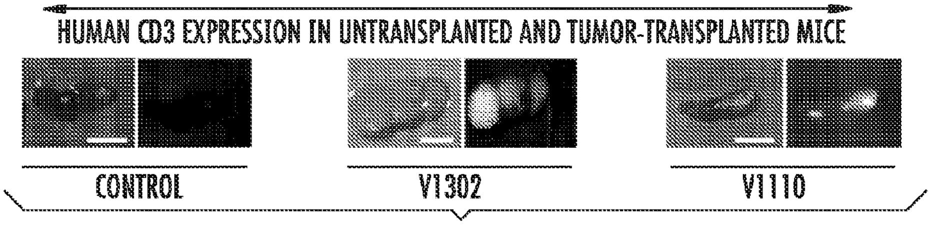

MAT II β Ablation Diminishes Leukemic Cell Growth in an NOD/Scid IL-2R$\gamma^{null}$ Mouse Leukemia Model To rule out possible in vitro culture artifacts, the ability of Jurkat cells that do not express MAT II β to survive and multiply in vivo in severely immunodeficient NOD/Scid IL-2R$\gamma^{null}$ mice was investigated (Shultz et al., (2005) J Immunol 174, 6477-6489). These mice allow heightened engraftment with xenogeneic cells because, besides lacking T, B, and NK cells, they are also deficient in complement and macrophage function (Shultz et al., (2005) J Immunol 174, 6477-6489). After mildly irradiating these mice, they were transplanted intraperitoneally with $15\times10^6$ V1110 or control V1302 cells (n=15 mice per group). Irradiated but non-injected mice served as additional controls. Tumor engraftment and growth were monitored weekly for 5 weeks post-transplant by determining the percentage of human CD3 and GFP expression in bone marrow (BM) and spleen derived cells, and by measuring serum levels of the surrogate tumor marker, β2-microglobulin (β2μ) (Zhang et al., (2004) Cancer Res 64(16), 5825-5829). GFP expression in whole spleens of sacrificed mice was also imaged for a semi-quantitative measure of tumor burden (FIG. 10C).

Figures 10D, 10E, 10F:
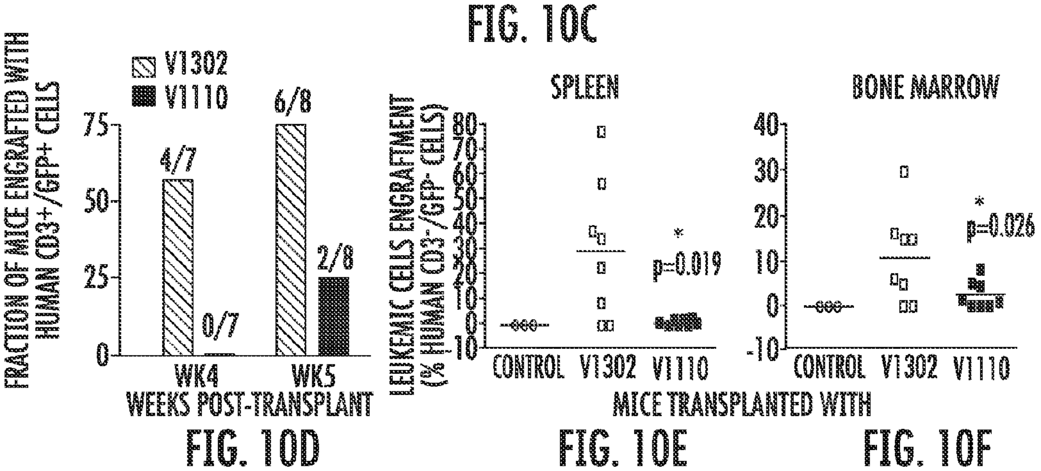
Figure 11:
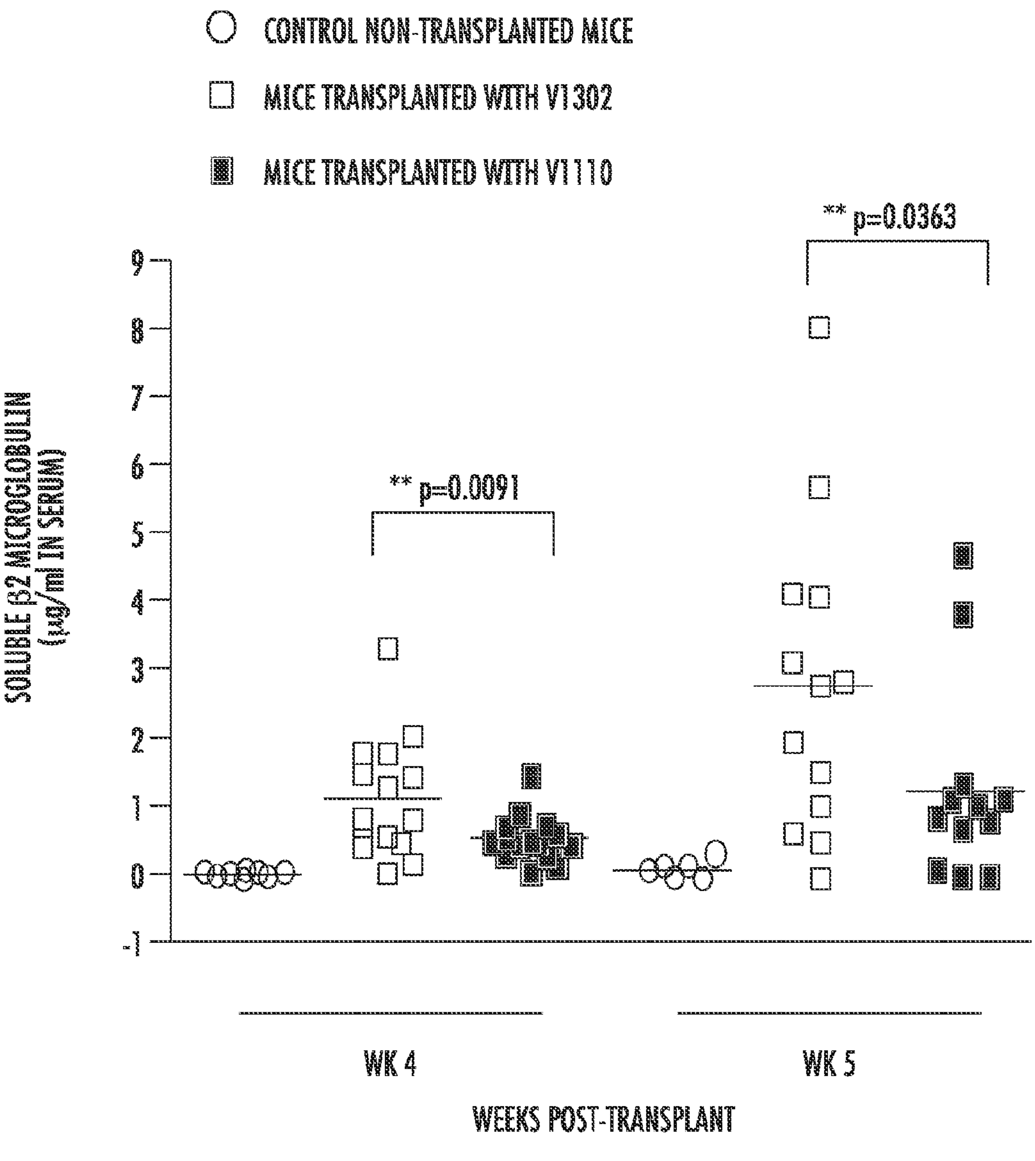
FIG. 11 is a plot depicting the effects of MAT II β ablation on engraftment of leukemic cells in vivo. Serum levels of the tumor marker, soluble β2 microglobulin (β2μ) were used as a surrogate tumor marker in control untransduce mice (open circles) and mice injected with either V1302 (open squares) or V1110-transduced (solid squares) cells. Mice were bled every week starting 12 days post-injections. Serum was used in an ELISA assay using a β2μ kit (R&D Systems, Inc., Minneapolis, Minn., United States of America) according to the manufacturer's instructions. Data shown are for week 4 and 5 post-injection. Statistical differences were calculated using Mann-Whitney test. (*p≦0.01-0.05, p≦0.001-0.01, *p≦0.001).
Figure 12A:
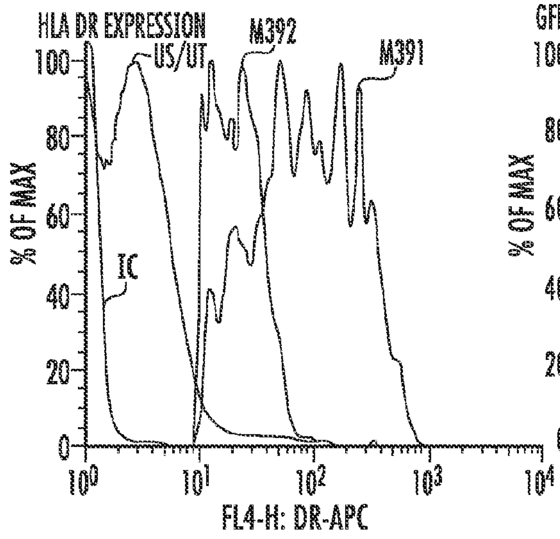
FIGS. 12A and 12B are flow cytometry histograms depicting the ability to propagate primary patient cells in vivo and to transduce them with retrovirus encoding shRNA. Leukemic cells from a B-ALL patient were propagated in NOD/Scid-IL-2R$\gamma^{null}$ mice. Primary B-ALL cells were purchased from ALLcells LLC and $10^7$ cells were injected intraperitoneally in NOD/Scid-IL-2R$\gamma^{null}$ mice. Mice were sacrificed 7 weeks post-transplant and the bone marrow cells were recovered and analyzed for the presence of human B-ALL cells by assessing surface DR expression using DR-APC from BD Biosciences to conform the engraftment of human B-ALL in these mice (FIG. 12A). Lentivirus vector expressing GFP (green fluorescent protein) was injected into transplanted and tansduction was repeated the next day to increase transduction levels (FIG. 12B). The data indicate that the B-ALL were transduced with the virus in vivo. These data demonstrate the ability to propagate primary patient cells in vivo and to transduce them with virus. Nanoparticles carrying MAT II β RNAi will be used to silence MAT II β specifically in leukemic cells in viva (M391=Mouse 391 (B-ALL), 3X-V1110 treated; M392=Mouse 392 (B-ALL), 3X-V1110 treated; US/UT=Unstained or Untreated BM cells; IC=Isotypic Control).
Figure 12B:
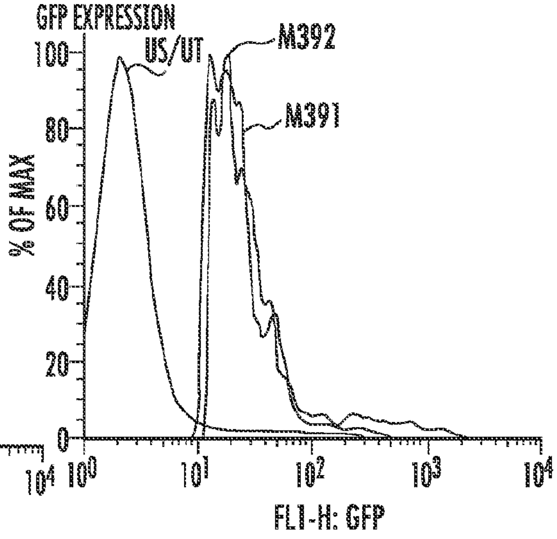

During the first 3 weeks none of the transplanted mice showed significant engraftment, but after 4 weeks 57% of mice transplanted with control V1302 cells began to show variable levels of engraftment in spleen (3-44% human $CD3^+$/$GFP^+$ cells; mean 16±7.6%) and in BM (3-12% human $CD3^+$/$GFP^+$ cells; mean 4±1.6%). Engraftment was much less evident in spleens of mice transplanted 4 weeks earlier with V1110 cells (0.96±0.32% $CD3^+$/$GFP^+$ cells; p=0.004). This trend continued through 5 weeks post-transplant, with significantly higher human $CD3^+$/$GFP^+$ cells in spleen and BM of mice injected with V1302 versus V1110 cells (Table 2 and FIG. 10A-10D). At 5 weeks, 25% of V1110 cells transplanted mice started to show low levels of $CD3^+/GFP^+$ engraftment in spleen (1.1±0.4%) and BM (2.4±1%). In stark contrast, 75% of mice transplanted with V1302 cells showed heightened engraftment in spleen (30±10%; p=0.02) and BM (11±4%; p=0.04), FIG. 10D. Additionally, levels of the surrogate tumor marker β2μ were 2-fold higher in mice transplanted with control V1302 leukemic cells than those transplanted with V1110 cells (FIG. 11).

Discussion of Examples 1-14

Examples 1-13 demonstrate that silencing the expression of the regulatory β subunit of MAT II exerts a significant growth disadvantage upon human Jurkat leukemic T cells under physiologic L-Met levels in vitro and in vivo. In the liver, L-Met levels are 80-100 μM, but in other tissues they range from 10-25 μM. Thus, the high Km hepatic isozyme, MAT III, can be fully functional in that organ without MAT II β. By contrast, MAT II, the only SAMe synthesizing enzyme in extrahepatic tissue, can only function when associated with its MAT II β regulatory subunit, which plays an important role in lowering MAT II $Km_{L\text{-}Met}$ to values close to physiological L-Met levels outside the liver (26,29,43). Without being bound by any one theory, it is believed that without the β subunit MAT II functions at minimal capacity and is not able to provide normal extrahepatic cells with adequate SAMe levels needed for their growth and survival. In resting human T cells MAT II β is expressed at low levels and mitogenic activation of these cells does not induce further expression of this subunit. By contrast, MAT II β is constitutively expressed at a much higher level in established and primary leukemic T cells (De La Rosa et al., (1992) Cancer Res 52, 3361-3366; De La Rosa et al., (1992) J Biol Chem 267(15), 10699-10704). Induction of MAT II β expression has been reported in several types of cancer and has been shown to confer a proliferative advantage to human hepatomas (Martinez-Chantar et al., (2003) Gastroenterology 124(4), 940-948).

The role of MAT II β in leukemic cells is even more crucial because leukemic T cells, both freshly explanted ALL-2 cells and the Jurkat cell line, utilize SAMe at significantly higher rates than normal resting or activated T cells (De La Rosa et al., (1992) Cancer Res 52, 3361-3366; De La Rosa et al., (1992) J Biol Chem 267(15), 10699-10704). The constitutive high expression of MAT II β in leukemic cells allows high levels of SAMe synthesis needed to meet the growth requirements of malignant cells. It would not have been desirable to target the MAT II α2 catalytic subunit to diminish SAMe in leukemic cells because that would be quite detrimental and toxic to normal cells that do not express the hepatic MAT I/III isozyme, i.e. the majority of extrahepatic cells. However, targeting MAT II β expression was more appropriate and practical because this would not block SAMe synthesis completely, but would reduce it to where the rapid growth and proliferation of malignant lymphocytes, and possibly other cancerous cells can no longer be sustained.

The data presented herein demonstrates the successful silencing of the MAT II β regulatory subunit without significantly affecting the expression of MAT II α2 subunit. Under these conditions, the in vitro and in vivo studies disclosed herein provide strong evidence that MAT II β ablation is detrimental to the growth of malignant T cells, and that this is directly due to drastic reductions in SAMe levels needed to support their rapid growth.

There is a large body of evidence that the growth of several types of tumors is dependent on high L-Met, and that L-Met deprivation causes cell cycle arrest in G2 phase (Breillout et al., (1990) J Natl Cancer Inst 82(20), 1628-1632;, Guo et al., (1993) Cancer Res. 53(23), 5676-5679). Several clinical studies demonstrated that diminishing L-Met in cancer patients by maintaining them on Met- or choline-free diet and/or administering methioninase exerts selective growth disadvantage pressure on cancer cells in vitro and in vivo, inducing mitotic and cell cycle arrest, apoptotic death, and widespread necrosis in tumors (Sun et al., (2003) Cancer Res 63, 8377-8383). Induction of Jurkat cells apoptosis and death by silencing MAT II β is in agreement with previous studies showing increased apoptosis and necrosis of tumor cells cultured in the absence of L-Met (Goseki et al., (1995) Jpn J Cancer Res 86(5), 484-489; Kokkinakis et al., (2006) Mol Cancer Res 4(8), 575-589). Significant apoptosis was observed in Jurkat cells lacking MAT II β at physiologic L-Met levels, indicating that direct depletion of SAM can be more effective than L-Met depletion in inducing tumor cell apoptosis in vivo. It is believed that targeting MAT II β expression in combination with restricting dietary L-Met alone or in conjunction with chemotherapeutic agents will prove to be a useful approach in the treatment of certain blood malignancies.

The growth of Jurkat cells with and without MAT II β expression was reduced at 10 μM compared to ≧20 μM L-Met; however, attempts to rescue these cells by incrementally increasing L-Met levels in culture revealed that the growth of cells expressing MAT II β was fully restored at 20 μM, whereas cells lacking MAT II β could not be rescued at this concentration. Even at unphysiologically high 50 μM L-Met significant apoptosis in cells lacking MAT II β was observed. Therefore, it appears possible to adjust L-Met levels in vivo in a way that would rescue normal cells while still inducing death and apoptosis of leukemic cells that do not express this important regulatory subunit.

The possibility that the in vitro observations are due to culture artifacts was ruled out when the ability of Jurkat cells that do and do not express MAT II β to engraft and survive in an in vivo environment of physiologic L-Met levels were compared in the hyper immune deficient NOD/ScidIL-2Rγnull mouse model. There were significant differences in the in vivo tumor growth and engraftment of Jurkat cells that do and do not express MAT II β, even in the absence of host immune rejection. Control transduced Jurkat cells grew well in this mouse model, whereas cells lacking MAT II β expression showed significant diminution in engraftment for up to 5 weeks post-transplant.

In summary, an approach that targets SAMe metabolism provides a good adjunctive therapeutic tool for the treatment of leukemia because of the their excessive requirement for this central metabolic compound. The in vivo data suggest that this approach, by itself, has a more drastic effect on diminishing leukemic cells growth than was originally anticipated. The stark difference in the in vivo survival and engraftment between the V1110- and V1302-transduced cells in mice lacking proper immune defenses was a surprising result that is believed to provide the basis to generate targeted therapeutics and dietary protocols to selectively diminish the growth of malignant lymphocytes with little or no effect on normal cells.

Example 15

Nanoparticle Approaches for Delivering RNAi Constructs to Target Cells In Vivo Phi29 pRNA nanoparticles were used to successfully deliver siRNA in vivo to target cells, including cancer cells.

The phi29 pRNA has a tendency to form dimers (2 pRNA), trimers (3 pRNA), and hexamers (6 pRNA) as a result of the interaction of interlocking loops. Thus, 2-6 pRNA chimeras can be incorporated into the RNA nanocomplex, with multiple positions available to carry RNA and other molecules for targeting, therapy, or detection etc. The 25 nm pRNA dimers serve as building blocks for the hexameric ring11 encircling the cargo, building nanomaterials via bottom-up assembly. To visualize their entry onto cells in vitro and in vivo, the pRNA and its package DNA can be labeled, e.g. Cy3-pRNA and Cy5-DNA12-14. Further details of pRNA construction have been previously described. (Federici, M. M., and Lotspeich, F. J. (1979) Biochem Pharmacol 28(10), 1689-1693; Kappler et al., (1988) J Med Chem 31(2), 384-389; Lavrador et al., (1998) J Enzyme Inhib 13(5), 361-367; Lombardini, J. B., and Sufrin, J. R. (1983) Biochem Pharmacol 32(3), 489-495; Vrudhula et al., (1989) J Med Chem. 32(4), 885-890; Sufrin, J. R., Lombardini, J. B., and Alks, V. (1993) Biochim Biophys Acta 1202(1), 87-91; Kotb, M., and Kredich, N. M. (1985) J Biol Chem 260(7), 3923-3930). These publications demonstrate that 20-40 nm pRNA nanoparticles readily gain entry into cells while escorting a variety of therapeutic RNA inside them. These pRNA nanoparticles have a long half-life and are not immunogenic nor toxic and they can easily incorporate RNAi constructs as well as targeting and tracking conjugates. The pRNA molecule contains intermolecular interaction domains and a 5'/3' helical domain. Hand-in-hand interaction of the right and left interlocking loops can be manipulated to produce desired stable dimers, trimers, or hexamers (6pRNA) [21], with multiple positions available to carry RNA molecules for targeting, therapy, or detection. It has been demonstrated that these therapeutic nanoparticles are able to halt growth of cancer cells or eradicate viruses.

Example 16

MAT II β RNAi-pRNA Construction

Figure 13:
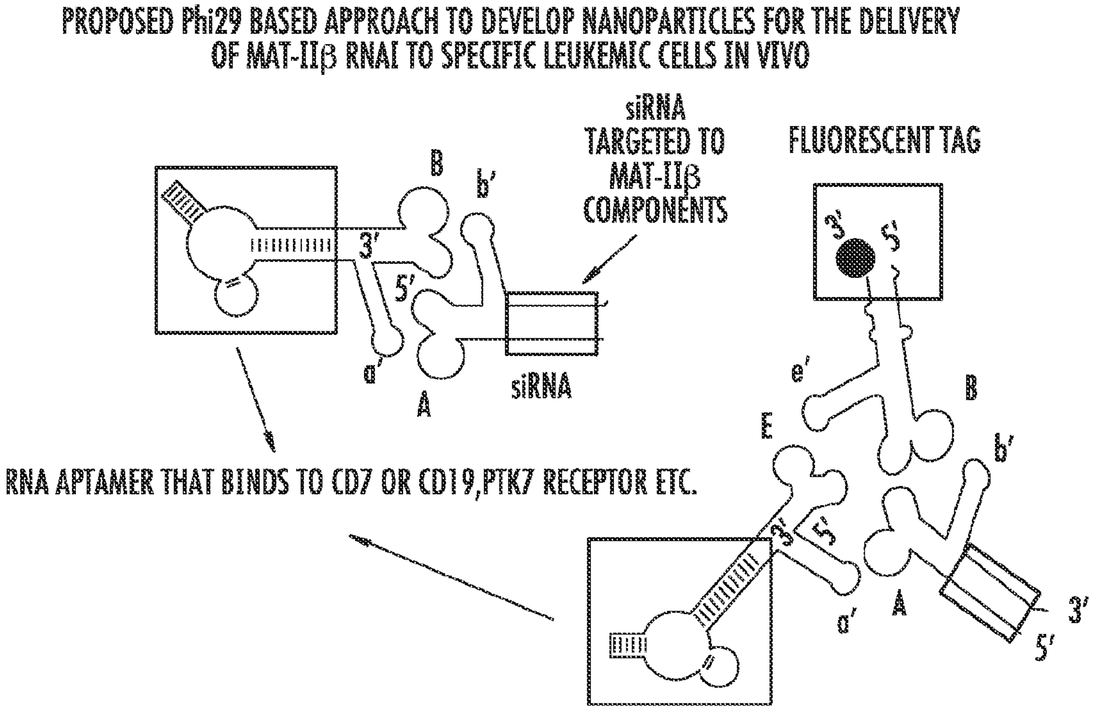
FIG. 13 is a schematic diagram illustrating an approach to develop nanoparticles for the delivery of MAT II β RNAi to specific leukemic cells in vivo.

The multimeric pRNA complexes (hexamer) are constructed to carry multiple components for specific cell recognition, image detection, endosome disruption, and therapeutic treatment. To concisely describe the construction of RNA complexes, upper-case letters are used for the upper loop (or right-hand loop; FIG. 13), and lower-case letters are used to represent the lower loop (or left hand loop). Complementary loops are assigned matched same letters in upper and lower cases, respectively; noncomplementary loops are assigned unmatched different letters.

For example, pRNA (A-b') itself has an unmatched upper right-hand loop A (5'G45G46A47C48) and a lower left-hand loop b' (3'U85G84C83G82), but is able to match and pair with the left-hand loop a' (3'C85C84U83G82) and right-hand loop B (5'A45C46G47C48), respectively, of the other pRNA (B-a') (FIG. 13), which also contains unmatched loops. pRNA/siRNA(GFP) represents a pRNA chimera that harbors an RNAi construct targeting MAT II β pRNA/siRNA(MAT II β) using MAT II β siRNA, RNA aptamer or ribozyme. The second domain of pRNA, at the 5'/3' paired ends, plays a role in the binding of the DNA packaging enzyme gp16 during phi29 DNA packaging. The RNAi construct is connected to the 3'/5' ends of the pRNA while being protected and folded independently from pRNA sequences.

One subunit of the pRNA complex carries a ligand or RNA aptamer that recognizes a specific cell-surface receptor, thereby induces receptor-mediated endocytosis. The second subunit carries a therapeutic siRNA, hammerhead ribozyme, antisense RNA, etc. The 3rd (4th, 5th or 6th, if needed) subunit is altered to carry a polymer to enhance endosome disruption for the therapeutic molecule release, or a reporter molecule to detect and monitor its delivery in vivo. FIG. 13 illustrates the general design strategy, which has the ability to undergo many modifications, including different RNAi constructs and different targeting and tracking ligands, as needed.

In vitro optimization studies include but are not limited to (i) selection of most efficient, specific and least toxic RNAi construct and most effective MAT II β silencing activity, with minimal activation of innate immune system, least off target effects or disruption of endogenous miRNA circuits; (ii) optimizing the ability of the RNAi construct to penetrate the cell membrane; (iii) protecting the construct from degradation by exonucleases within the cell; (iv) directing intracellular trafficking of the pRNA-RNAi construct to appropriate cell compartment; and (v) ensuring correct folding of RNAi constructs in the cell if fused to a carrier. For the in vivo studies, approaches to protect the constructs when administered systemically can be optimized to ensure that they are safely and specifically delivered in high quantities to their target cells for efficient and effective MAT II β ablation. Detailed information as to how to optimize RNAi constructs h as previously been described (Kotb et al., (1997) Trends Genet 13(2), 51-52).

Single-chain antibodies (scFv) and aptamers directed to surface antigens that are expressed preferentially or overexpressed on the surface of the T or B leukemic cells are tested for the ability to deliver the pRNA nanoparticles. The scFvCD7-9R or scFvCD19-9R are bound to the pRNA via a 9R linker, for delivery of MAT II β RNAi constructs. The functionality of these constructs and retention of target specificity after assembly into the nanoparticles is tested by flow cytometry against both T and B normal and leukemic cells to ensure specificity. Internalization and gene silencing efficiency of the complex is tested in vitro prior to incorporation into the nanoparticles. The efficiency of the various fluorphore conjugates in tracking the entry of constructs into target cells is also tested.

Statistical differences in the ability of RNAi constructs, delivered by the different targeting constructs described above, to (i) silence MAT II β expression, specifically in the primary T or B leukemic cells and (ii) elicit undesirable effects (e.g. toxicity, perturbation of endogenous miRNA, off target effects, etc.), can be analyzed using two-tailed paired t-tests with a confidence interval of 95%, with $P \leqq 0.01$ considered significant. Serum and RNase stability of naked and packaged NP-RNAi constructs can be assessed. IFN production, nonspecific activation, off-target effects and perturbation of endogenous miRNA using a limited number of transcriptome and miRNA profiling, can also be assessed followed by QRT-PCR validation. The Wilcoxon signed rank test can be used to assess significant differences within each cell line or patient's leukemic cells after different treatments with control of MAT II β specific constructs.

After optimization of NP-RNAi constructs bioavailability and specificity, the best constructs are used to assess their anti-leukemic potential in the optimized NOD/SCIDIL2rγnull mouse model of established leukemia. Initial in vivo optimization studies can be done using leukemic cell lines (e.g. Jurkat). Once the in vivo targeting system is optimized it can be tested in mice engrafted with primary cells from patients, followed by further optimization. First, the biodistribution, stability and pharmacokinetics of the constructs are assessed in the presence and absence of leukemic cells in vivo. Blood is sampled from the retro-orbital vein at 1, 6, and 12 hours post injection to quantify the concentration of the tagged nanoparticles in plasma versus uptake into the intended leukemic cells by regular fluorometry, flow cytometry and/or immunohistochemcical staining and confocal microscopy, depending on the number of cells recovered and the parameter being tested. Route, dose and time of therapeutic nanoparticle delivery relevant to tumor engraftment can also be optimized. Treatment dose and regiment is optimized for each construct and tumor type as needed. Selective delivery of the pRNA/RNAi(MAT II β) to the intended cells is monitored by tracking the labeled ligand. Ablation of gene expression is determined by recovering tumor cells from the test treated and control treated mice and assessing MAT II β expression at the gene and protein level as detailed. Nonspecific targeting, effects and toxicity of the therapeutic constructs is evaluated in mice engrafted with irrelevant leukemic tumors or with normal PBMCs. Before and at different time points after administration of the constructs, plasma is recovered and assayed for soluble biomarkers that are indicative of therapeutic efficacy (e.g. soluble β2μ levels) or markers of systemic toxicity. Body weight and clinical symptoms are monitored daily. Mice are sacrificed on specific optimized dates, the target leukemic cells are isolated by magnetic beads and the expression of MAT II β in cells from control and specifically treated mice is assessed as previously described herein above.

The therapeutic efficacy of the constructs is assessed by determining statistically significant effects on tumor burden and disease progression using the above optimized parameters and statistical tests using the most informative disease biomarkers that predict tumor burden and disease progression as well as a disease scoring index to allow for the identification and application of reliable statistical assessments of disease severity and outcome before and after administration of the therapeutic constructs. The various parameters proposed and optimized, including serum β2μ and other biomarkers that reflect tumor burden and can adequately assess disease progression and severity, are used to compare the therapeutic efficacy of the various RNAi constructs, and the various approaches for escorting them to the intended target cell. A generalized estimating equations (GEE) approach is used to model disease scores collected over time and to compare disease severity of control versus treated groups.

REFERENCES

All references cited herein, including but not limited to patents, patent applications and publications thereof, scientific publications, database entries, and references available on the World Wide Web, are incorporated herein by reference to the extent that they supplement, explain, provide a background for, or teach methodology, techniques, and/or compositions employed herein.

Adelman et al. (1983) DNA 2:183
Ahuja et al., *Cancer Res. (*1998) 23:5489-94
Alam & Cook (1990) *Anal Biochem* 188:245-254
Altschul et al. (1990) *J Mol Biol* 215:403-410
Alvarez et al. (1993) Biochem. J. 293, 481-486
Ausubel et al. (1992) Current Protocols in Molecular Biology, (J. Wylie & Sons, N.Y.)
Ausubel (1995) *Short Protocols in Molecular Biology,* 3rd ed. Wiley, New York, N.Y., United States of America
Baric, I., et al. (2004) Proc Natl Acad Sci USA 101(12), 4234-4239
Bass, *Nature* 411:428-429, 2001
Batzer et al. (1991) *Nucleic Acid Res* 19:5081
Belinsky et al., *Proc. Natl. Acad. Sci. USA (*1998) 20:11891-6
Belinsky S A et al. (2004) Cancer 4, 1-11
Belinsky S A et al. (2005) Clin Cancer Res. 11, 6505-6511
Bernstein et al., *Nature* 409:363-366, 2001
Breillout, F., Antoine, E., and Poupon, M. F. (1990) J Natl Cancer Inst 82(20), 1628-1632
Butron, K. (1956) Biochem. J. 62, 315-319
Cai J, et al. (1966). Hepatology. 24, 1090-7
Canadian Patent Application No. 2,359,180).
Cantoni, G. L. (1953) J Biol Chem 204(1), 403-416
Chiang, et al. (1996) FASEB J. 10: 471-480
Coffield, V. M., Helms, W. S., Jiang, Q., and Su, L. (2004) J Exp Med 200(10), 1315-1324
Coulter, A., Lombardini JB, Sufrin, J., and Talalay, P. (1974) Mol Pharmacol. 10(2), 319-334
Cubitt et al. (1995) *Trends Biochem Sci* 20:448-455
Cunningham, L., and Aplenc, R. (2007) Expert Opin Pharmacother 8(15), 2519-2531
De La Rosa et al. (1995) J. Biol. Chem. 270:21860-21868
De La Rosa et al. (1992) Cancer Res 52, 3361-3366
De La Rosa et al. (1992) J. Biol. Chem. 267, 10699-106704
Elbashir et al. *Nature* 411:494-498, 2001
Elbashir et al., *Genes Dev* 15:188-200, 2001b
Federici, M. M., and Lotspeich, F. J. (1979) Biochem Pharmacol 28(10), 1689-1693
Finkelstein et al. (1975) *Biochem. Biophys. Res. Commun.* 66: 81-7
Finkelstein, J. D. (1990) J Nutr Biochem 1(5), 228-237
Finkelstein, J. D. (2006) J Nutr 136(6 Suppl), 1750S-1754S
Fire et al., *Nature* 391:806-811, 1998
Fire, *Trends Genet* 15:358-363, 1999
Fronhoffs et al., (2002) Mol Cell Probes 16(2), 99-110
Garcia-Trevijano et al., (2000) FASEB J 14(15), 2511-2518
Glover & Hames (1995) *DNA Cloning: A Practical Approach,* 2nd ed. IRL Press at Oxford University Press, New York, N.Y., United States of America
Goseki et al. (1995) Jpn J Cancer Res 86(5), 484-489
Greenberg at al. (1994) *Mol Endocrinol* 8:230-239
Greenberg et al. (2007) Chest 132, 1247-1252
Guo et al., (1993) Cancer Res. 53(23), 5676-5679
Halim et al. (1999) J. Biol. Chem. 274, 29720-29725
Hammond et al., *Nature* 404:293-296, 2000
Henikoff & Henikoff (1992) *Proc Natl Acad Sci USA* 89:10915-10919.
Herman J G, et al. (2003) N Engl J Med. 349, 2042-2054
Hoffman, J. L. (1983) Methods Enzymol 94, 223-228
Horikawa et al. (1990) J. Biol. Chem. 265, 13683-6
Horikawa, S., and Tsukada, K. (1991) Biochem. Int. 25, 81-90
Ito K et al. (2000) and in Surg. Today 30, 706-710
Kappler et al., (1988) J Med Chem 31(2), 384-389
Karlin & Altschul (1993) *Proc Natl Acad Sci USA* 90:5873-5877
Klump et al., *Gastroenterology (*1998) 6:1381-6
Kokkinakis et al., (2006) Mol Cancer Res 4(8), 575-589
Kotb et al., (1997) Trends Genet. 13, 51-2
Kotb et al., (1993) Pharmacol Ther 59(2), 125-143
Kotb et al., (1985) J Biol Chem 260(7), 3923-3930
Kotb et al., (1990) Biochim. Biophys. Acta 1039(2): 253-60
Kotb et al., (1990) Biochim Biophys Acta 1040(2), 137-144
Kurihara et al. (2000) *J Clin Invest* 106:763-771
Langkamp-Henken at al. (1994) Biochim. Biophys. Acta 1201, 397-404
Lavrador, K., Allart, B., Guillerm, D., and Guillerm, G. (1998) J Enzyme Inhib 13(5), 361-367

Lee et al. (2000) *Anticancer Res* 20:417-422
LeGros et al. (1997) J. Biol. Chem. 272, 16040-16047
LeGros et al. (2000) J. Biol. Chem. 275, 2359-2366
Liau et al. (1979) Cancer Res. 39, 162-69
Liu et al. (2007) Hepatol. Res. 375, 366-88
Loehrer et al., (1997) J Pharmacol Exp. Ther 282(2), 845-850
Loenen, W. A. (2006) Biochem Soc Trans 34(Pt 2), 330-333
Lombardini et al., (1983) Biochem Pharmacol 32(3), 489-495
Martinez-Chantar et al., (2003) Gastroenterology 124(4), 940-948
Mato et al., (1994) Adv. Exp. Med. Biol. 368, 113-7
Mato et al., (1997) Pharmacol. Ther. 73: 265-280
Mato et al., (2002) Faseb J 16(1), 15-26
Mitsui et al. (1988) J. Biol. Chem. 263, 11211-16
Mudd et al. (1995) Disorders of transsulfuration, 7th Ed. The Molecular and Metabolic Basis of Inherited Diseases (Scriver, C. R., Beaudet, A. L., Sly, W. S., and Valle, D., Eds.), McGraw-Hill Inc., New York
Mudd, S. H. (1973) The Adenosyltransferases, Third Edition Ed. The Enzymes, Group Transfer (Part A) (Bayer, P. D., Ed.), III
Needleman et al. (1970) J. Mol. Biol. 48:443
Nykanen et al., *Cell* 107:309-321, 2001
Oden, K., and Clarke, S. (1983) Biochemistry 22, 2978-2986
Ohtsuka et al. (1985) *J Biol Chem* 260:2605-2608
Okada et al. (1981) Biochemistry 20, 934-940
Pear et al., (1993) Proc Natl Acad Sci USA 90(18), 8392-8396
Pearson & Lipman (1988) *Proc Natl Acad Sci USA* 85:2444-2448
Pui, C. H., and Jeha, S. (2007) Nat Rev Drug Discov 6(2), 149-165
Rose & Botstein (1983) *Meth Enzymol* 101:167-180
Rossolini et al. (1994) *Mol Cell Probes* 8:91-98)
Sakata et al. (1993) J. Biol. Chem. 268, 13978-86
Sambrook & Russell (2001) *Molecular Cloning: A Laboratory Manual,* 3rd ed. Cold Spring Harbor Laboratory Press, Cold Spring Harbor, N.Y., United States of America
Sambrook et al. (1989) Molecular Cloning: A Laboratory Manual (Cold Spring Harbor Laboratory Press, Cold Spring Harbor, N.Y.)
Shultz et al., (2005) J Immunol 174, 6477-6489
Silhavy et al. (1984) *Experiments with Gene Fusions*. Cold Spring Harbor Laboratory, Cold Spring Harbor, N.Y., United States of America
Smith et al., Adv. Appl. Math. 2:482 (1981)
Sufrin et al., (1993) Biochim Biophys Acta 1202(1), 87-91
Sufrin et al., (1979) Mol Pharmacol 15(3), 661-677
Sullivan, D. M., and Hoffman, J. L. (1983) Biochemistry 22, 1636-41
Suma, Y., Shimizu, K., and Tsukada, K. (1986) J Biochem 100(1), 67-75
Sun et al., (2003) Cancer Res 63, 8377-8383
Tabor, C. W., and Tabor, H. (1984) Adv Enzymol Relat Areas Mol Biol 56, 251-282
Tabor, C. W., and Tabor, H. (1984) Annu Rev Biochem 53, 749-790
Taxman, D. J., Livingstone, L. R., Zhang, J., Conti, B. J., Iocca, H. A., Williams, K. L., Lich et al., (2006) BMC Biotechnol 6, 7
Tijssen (1993) *Laboratory Techniques in Biochemistry and Molecular Biology-Hybridization with Nucleic Acid Probes*. Elsevier, N.Y., United States of America
U.S. Patent Application Publication No. 2006/0009402
U.S. Pat. No. 6,506,559
U.S. Pat. No. 6,696,279
Ubagai et al. (1995) J. Clin. Invest. 96, 1943-47
Vrudhula et al., (1989) J Med Chem. 32(4), 885-890
Weinstein SJ et al. (2001) Cancer Causes and Control 12, 317-324
Wetmur & Davidson (1968) J. Mol. Biol. 31:349-370
Wianny & Zernicka-Goetz, *Nature Cell Biol* 2:70-75, 1999
WO 00/01846
WO 00/44895
WO 00/44914
WO 00/44914
WO 00/63364
WO 01/04313
WO 01/29058
WO 01/36646
WO 01/36646
WO 01/68836
WO 01/75164
WO 01/92513
WO 02/055692
WO 02/055693
WO 02/44321
WO 03/006477
WO 99/07409
WO 99/32619
WO 99/32619
WO 97/47763
Wong et al., (2003) Nat Immunol 4(9), 891-898
Yang et al. (2008) *Gastroenterology* 134, 281-91
Yu et al. (1999) *Cancer Res* 59:4200-4203
Zhang et al., (2004) Cancer Res 64(16), 5825-5829
Zhang et al. (2006) Gene Medicine 8

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method of modulating MAT II activity in a vertebrate subject, the method comprising administering to the vertebrate subject an effective amount of a substance capable of modulating expression of the MAT II β subunit in the vertebrate subject, wherein the substance comprises an RNA interference (RNAi) molecule directed to MAT II β subunit selected from the group consisting of short hairpin RNA (shRNA) and small interfering RNA (siRNA), wherein the shRNA comprises a nucleotide sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, and SEQ ID NO: 11 and wherein the siRNA comprises a nucleotide sequence selected from the group consisting of SEQ ID NO: 12, SEQ ID NO: 13, SEQ ID NO: 14, and SEQ ID NO: 15, whereby modulation of MAT II activity is accomplished.

2. The method of claim 1, wherein modulating the expression of MAT II β subunit comprises modulating expression of the MAT2B gene.

3. The method of claim 1, wherein modulating MAT II activity comprises decreasing SAM synthesis.

4. The method of claim 1, wherein the RNAi molecule comprises a short hairpin RNA (shRNA), whereby the shRNA modulates expression of MAT II β subunit by RNAi.

5. The method of claim 4, wherein the substance further comprises a delivery vehicle selected from the group consisting of a viral vector, an antibody, an aptamer and a nanoparticle, for delivering the shRNA to a target cell.

6. The method of claim 1, wherein the RNAi molecule comprises a small interfering RNA (siRNA), whereby the siRNA modulates expression of MAT II β subunit by RNAi.

7. The method of claim 6, wherein the substance further comprises a delivery vehicle selected from the group consisting of a viral vector, an antibody, an aptamer, and a nanoparticle for delivering the siRNA to a target cell.

8. The method of claim 1, whereby MAT II activity is modulated by interfering with MAT II β subunit interaction with MAT II α2 catalytic subunit.

9. The method of claim 1, wherein the vertebrate is a mammal.

10. A method of treating a subject suffering from a disorder associated with MAT II biological activity in the subject, the method comprising: administering to the subject an effective amount of a substance capable of modulating expression of MAT II β subunit in the subject, whereby modulation of the expression of MAT II β subunit is accomplished; and modulating MAT II biological activity in the subject through the modulation of the expression of MAT II β subunit, or through the modulation of MAT II β subunit interaction with MAT II α2 subunit, wherein the substance comprises an RNAi molecule directed to MAT II β subunit selected from the group consisting of shRNA and siRNA, wherein the shRNA comprises a nucleotide sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, and SEQ ID NO: 11 and wherein the siRNA comprises a nucleotide sequence selected from the group consisting of SEQ ID NO: 12, SEQ ID NO: 13, SEQ ID NO: 14, and SEQ ID NO: 15, whereby treatment of the disorder is accomplished.

11. The method of claim 10, wherein the modulated expression of MAT II β subunit comprises the modulated expression of the MAT2B gene.

12. The method of claim 10, wherein the shRNA or siRNA modulates expression of MAT II β subunit by RNAi.

13. The method of claim 12, wherein the shRNA or siRNA is delivered to a target cell by a delivery vehicle selected from the group consisting of a viral vector, an antibody, an aptamer, and a nanoparticle.

14. The method of claim 10, further comprising the administration of radiation therapy, chemotherapy, gene therapy, immunotherapy, a dietary treatment, or combinations thereof.

15. The method of claim 10, wherein the disorder is cancer.

16. The method of claim 15, wherein the cancer is leukemia.

17. A method of treating a subject suffering from a disorder associated with MAT II biological activity in the patient, the method comprising administering to the subject a therapeutic composition comprising a MAT II β subunit siRNA, shRNA, miRNA, hammerhead ribozyme, or other molecule that interferes with the MAT II R biological activity by reducing its expression or a therapeutic composition comprising a small molecule, peptide, antibody or aptamer capable of interfering with the interaction between the MAT II β subunit and the MAT II α2 subunit, wherein the shRNA comprises a nucleotide sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, and SEQ ID NO: 11 and wherein the siRNA comprises a nucleotide sequence selected from the group consisting of SEQ ID NO: 12, SEQ ID NO: 13, SEQ ID NO: 14, and SEQ ID NO: 15, whereby the disorder is treated.

18. The method of claim 17, wherein the MAT II biological activity comprises MAT II biological activity endogenous to the subject.

19. The method of claim 17, wherein the therapeutic composition further comprises a delivery vehicle selected from the group consisting of a viral vector, an antibody, an aptamer, and a nanoparticle for delivering the therapeutic composition to a target cell.

20. The method of claim 17, wherein modulating MAT II biological activity comprises modulating MAT II specific activity.

21. The method of claim 17, wherein modulating MAT II biological activity comprises modulating MAT II enzyme kinetics.

22. method of claim 17, wherein modulating MAT II biological activity results in decreased production of SAM.

23. The method of claim 17, further comprising the administration of radiation therapy, chemotherapy, gene therapy, immunotherapy, a dietary treatment, or combinations thereof.

24. The method of claim 17, wherein the disorder is cancer.

25. The method of claim 24, wherein the disorder is leukemia.

26. A method for modulating MAT II biological activity in a cell comprising: delivering to the cell an effective amount of a vector comprising a polynucleotide that encodes a MAT II β subunit siRNA, shRNA, miRNA, hammerhead ribozyme, or other molecule that interferes with the MAT II β biological activity by reducing its expression, or a therapeutic composition comprising a small molecule, peptide, antibody or aptamer capable of interfering with the interaction between the MAT II β subunit and the MAT II α2 subunit, wherein MAT II biological activity is modulated; and maintaining the cell under conditions sufficient for expression of said siRNA, shRNA, miRNA, hammerhead ribozyme, or a molecule that interferes with the MAT II β biological activity by modulating its expression or interfering with its interaction with MAT II α2 subunit, wherein the shRNA comprises a nucleotide sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, and SEQ ID NO: 11 and wherein the siRNA comprises a nucleotide sequence selected from the group consisting of SEQ ID NO: 12, SEQ ID NO: 13, SEQ ID NO: 14, and SEQ ID NO: 15.

27. The method of claim 26, further comprising a delivery vehicle selected from the group consisting of a viral vector, an aptamer, an antibody and a nanoparticle, for delivering the siRNA, shRNA, miRNA, or hammerhead ribozyme to the cell.

28. The method of claim 26, wherein the cell is a leukemic cell or other cancer cell where modulating MAT II biological activity has a therapeutic effect.

29. The method of claim 26, wherein the cancer cell is a primary cancer cell or a cell line representing a primary cancer cell.

30. A method for suppressing the growth of a cancer cell, the method comprising: contacting the cancer cell with a vector encoding an RNAi molecule selected from the group consisting of an siRNA, shRNA, miRNA, and hammerhead ribozyme under conditions sufficient to allow entry of the vector into the cell, wherein the RNAi molecule comprises a ribonucleotide sequence corresponding to a coding strand of a MAT II β subunit gene; and decreasing the biological activity of MAT II by siRNA, shRNA miRNA, or hammerhead ribozyme mediated down-regulation of MAT II β subunit gene expression through RNAi, wherein the decreased biological activity of MAT II suppresses the growth of the cancer cell, wherein the shRNA comprises a nucleotide sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, and SEQ ID NO: 11 and wherein the siRNA comprises a nucleotide sequence selected from the group consisting of SEQ ID NO: 12, SEQ ID NO: 13, SEQ ID NO: 14, and SEQ ID NO: 15.

31. The method of claim 30, wherein the siRNA or shRNA down-regulates the expression of MAT II β subunit by inhibiting expression of the MAT2B gene.

32. The method of claim 30, wherein the cell is in a subject.

33. The method of claim 32, wherein the subject is a mammal.

34. The method of claim 30, wherein the vector is a retroviral vector.

35. The method of claim 30, further comprising a delivery vehicle, selected from the group consisting of a viral vector, an antibody, an aptamer, and a nanoparticle for delivering the siRNA, shRNA, miRNA, or hammerhead ribozyme to the cell.

36. The method of claim 30, wherein the cancer cell is a leukemic cell, a leukemic T or B cell, or other cancer cell where modulating MAT II biological activity has a therapeutic effect.

* * * * *

SEQUENCE LISTING

```
<160> NUMBER OF SEQ ID NOS: 30

<210> SEQ ID NO 1
<211> LENGTH: 97
<212> TYPE: DNA
<213> ORGANISM: Artificial Sequence
<220> FEATURE:
<223> OTHER INFORMATION: shRNA directed against MATIIB
```

<400> SEQUENCE: 1
ggaatcttat aagttctgta tgagaccact ctttcccgca gttcatcaca tcattcttca 60
agagagaatg atgtgatgaa ctgctttttc tagagca 97

<210> SEQ ID NO 2
<211> LENGTH: 97
<212> TYPE: DNA
<213> ORGANISM: Artificial Sequence
<220> FEATURE:
<223> OTHER INFORMATION: shRNA directed against MATIIB

<400> SEQUENCE: 2
ggaatcttat aagttctgta tgagaccact ctttcccgca gttcatcgga tcattcttca 60
agagagaatg atccgatgaa ctgctttttc tagagca 97

<210> SEQ ID NO 3
<211> LENGTH: 97
<212> TYPE: DNA
<213> ORGANISM: Artificial Sequence
<220> FEATURE:
<223> OTHER INFORMATION: shRNA directed against MATIIB

<400> SEQUENCE: 3
ggaatcttat aagttctgta tgagaccact ctttcccgac ctattactga cagcccttca 60
agagagggct gtcagtaata ggtctttttc tagagca 97

<210> SEQ ID NO 4
<211> LENGTH: 97
<212> TYPE: DNA
<213> ORGANISM: Artificial Sequence
<220> FEATURE:
<223> OTHER INFORMATION: shRNA directed against MATIIB

<400> SEQUENCE: 4
ggaatcttat aagttctgta tgagaccact ctttcccgac ctattaacga cagcccttca 60
agagagggct gtcgttaata ggtctttttc tagagca 97

<210> SEQ ID NO 5
<211> LENGTH: 97
<212> TYPE: DNA
<213> ORGANISM: Artificial Sequence
<220> FEATURE:
<223> OTHER INFORMATION: shRNA directed against MATIIB

<400> SEQUENCE: 5
ggaatcttat aagttctgta tgagaccact ctttccctca ctggtctggc aatgaattca 60
agagattcat tgccagacca gtgatttttc tagagca 97

<210> SEQ ID NO 6
<211> LENGTH: 95
<212> TYPE: DNA
<213> ORGANISM: Artificial Sequence
<220> FEATURE:
<223> OTHER INFORMATION: shRNA directed against MATIIB

<400> SEQUENCE: 6
ggaatcttat aagttctgta tgagaccact ctttccctta ggatctttca ggtaattcaa 60
gagattacct gaaagatcct aatttttcta gagca 95

<210> SEQ ID NO 7
<211> LENGTH: 97
<212> TYPE: DNA

-continued

<213> ORGANISM: Artificial Sequence
<220> FEATURE:
<223> OTHER INFORMATION: shRNA directed against MATIIB

<400> SEQUENCE: 7
ggaatcttat aagttctgta tgagaccact ctttcccaaa ttatgatcct taaatattca 60
agagatattt aaggatcata attttttttc tagagca 97

<210> SEQ ID NO 8
<211> LENGTH: 94
<212> TYPE: DNA
<213> ORGANISM: Artificial Sequence
<220> FEATURE:
<223> OTHER INFORMATION: shRNA directed against MATIIB

<400> SEQUENCE: 8
ggaatcttat aagttctgta tgagaccact ctttcccgca gttcatcaca tcattcttca 60
agagagaatg atgtgatgaa ctgctttttc taga 94

<210> SEQ ID NO 9
<211> LENGTH: 94
<212> TYPE: DNA
<213> ORGANISM: Artificial Sequence
<220> FEATURE:
<223> OTHER INFORMATION: shRNA directed against MATIIB

<400> SEQUENCE: 9
ggaatcttat aagttctgta tgagaccact ctttcccgca gttcatcgga tcattcttca 60
agagagaatg atccgatgaa ctgctttttc taga 94

<210> SEQ ID NO 10
<211> LENGTH: 94
<212> TYPE: DNA
<213> ORGANISM: Artificial Sequence
<220> FEATURE:
<223> OTHER INFORMATION: shRNA directed against MATIIB

<400> SEQUENCE: 10
ggaatcttat aagttctgta tgagaccact ctttcccgac ctattactga cagcccttca 60
agagagggct gtcagtaata ggtctttttc taga 94

<210> SEQ ID NO 11
<211> LENGTH: 94
<212> TYPE: DNA
<213> ORGANISM: Artificial Sequence
<220> FEATURE:
<223> OTHER INFORMATION: shRNA directed against MATIIB

<400> SEQUENCE: 11
ggaatcttat aagttctgta tgagaccact ctttcccgac ctattaacga cagcccttca 60
agagagggct gtcgttaata ggtctttttc taga 94

<210> SEQ ID NO 12
<211> LENGTH: 19
<212> TYPE: DNA
<213> ORGANISM: Artificial Sequence
<220> FEATURE:
<223> OTHER INFORMATION: siRNA directed against MATIIB

<400> SEQUENCE: 12
cggucuuuca uuaguuuau 19

<210> SEQ ID NO 13

-continued

<211> LENGTH: 19
<212> TYPE: DNA
<213> ORGANISM: Artificial Sequence
<220> FEATURE:
<223> OTHER INFORMATION: siRNA directed against MATIIB

<400> SEQUENCE: 13
uuaggaucuu ucagguaaa 19

<210> SEQ ID NO 14
<211> LENGTH: 19
<212> TYPE: DNA
<213> ORGANISM: Artificial Sequence
<220> FEATURE:
<223> OTHER INFORMATION: siRNA directed against MATIIB

<400> SEQUENCE: 14
ccuuaaauau uugagaguc 19

<210> SEQ ID NO 15
<211> LENGTH: 19
<212> TYPE: DNA
<213> ORGANISM: Artificial Sequence
<220> FEATURE:
<223> OTHER INFORMATION: siRNA directed against MATIIB

<400> SEQUENCE: 15
cucucaacuu aauguggau 19

<210> SEQ ID NO 16
<211> LENGTH: 19
<212> TYPE: DNA
<213> ORGANISM: Homo sapiens

<400> SEQUENCE: 16
ccuuaaauau uugagaguc 19

<210> SEQ ID NO 17
<211> LENGTH: 26
<212> TYPE: DNA
<213> ORGANISM: Artificial Sequence
<220> FEATURE:
<223> OTHER INFORMATION: forward primer

<400> SEQUENCE: 17
cagatctaat aattggcatg cagttg 26

<210> SEQ ID NO 18
<211> LENGTH: 26
<212> TYPE: DNA
<213> ORGANISM: Artificial Sequence
<220> FEATURE:
<223> OTHER INFORMATION: reverse primer

<400> SEQUENCE: 18
caggcctagc atttctcgga cgttgt 26

<210> SEQ ID NO 19
<211> LENGTH: 46
<212> TYPE: DNA
<213> ORGANISM: Artificial Sequence
<220> FEATURE:
<223> OTHER INFORMATION: sense primer

<400> SEQUENCE: 19
gcgtaatacg actcactata gggagaacct cttacctcag ttacaa 46

<210> SEQ ID NO 20
<211> LENGTH: 46
<212> TYPE: DNA
<213> ORGANISM: Artificial Sequence
<220> FEATURE:
<223> OTHER INFORMATION: antisense primer

<400> SEQUENCE: 20
gcgtaatacg actcactata gggcgttgta actgaggtaa gaggtt 46

<210> SEQ ID NO 21
<211> LENGTH: 1867
<212> TYPE: DNA
<213> ORGANISM: Homo sapiens
<220> FEATURE:
<221> NAME/KEY: CDS
<222> LOCATION: (61)..(1062)

<400> SEQUENCE: 21
cgtcgatcct gggttggagg aggtggcggc cgctgaggct gcggcgtgaa gacggcgggc 60 atg gtg ggg cgg gag aaa gaa ctg tct ata cac ttt gtt ccc ggg agc 108
Met Val Gly Arg Glu Lys Glu Leu Ser Ile His Phe Val Pro Gly Ser
1 5 10 15 tgt cgg ctg gtg gag gag gaa gtt aac atc cct aat agg agg gtt ctg 156
Cys Arg Leu Val Glu Glu Glu Val Asn Ile Pro Asn Arg Arg Val Leu
20 25 30 gtt act ggt gcc act ggg ctt ctt ggc aga gct gta cac aaa gaa ttt 204
Val Thr Gly Ala Thr Gly Leu Leu Gly Arg Ala Val His Lys Glu Phe
35 40 45 cag cag aat aat tgg cat gca gtt ggc tgt ggt ttc aga aga gca aga 252
Gln Gln Asn Asn Trp His Ala Val Gly Cys Gly Phe Arg Arg Ala Arg
50 55 60 cca aaa ttt gaa cag gtt aat ctg ttg gat tct aat gca gtt cat cac 300
Pro Lys Phe Glu Gln Val Asn Leu Leu Asp Ser Asn Ala Val His His
65 70 75 80 atc att cat gat ttt cag ccc cat gtt ata gta cat tgt gca gca gag 348
Ile Ile His Asp Phe Gln Pro His Val Ile Val His Cys Ala Ala Glu
85 90 95 aga aga cca gat gtt gta gaa aat cag cca gat gct gcc tct caa ctt 396
Arg Arg Pro Asp Val Val Glu Asn Gln Pro Asp Ala Ala Ser Gln Leu
100 105 110 aat gtg gat gct tct ggg aat tta gca aag gaa gca gct gct gtt gga 444
Asn Val Asp Ala Ser Gly Asn Leu Ala Lys Glu Ala Ala Ala Val Gly
115 120 125 gca ttt ctc atc tac att agc tca gat tat gta ttt gat gga aca aat 492
Ala Phe Leu Ile Tyr Ile Ser Ser Asp Tyr Val Phe Asp Gly Thr Asn
130 135 140 cca cct tac aga gag gaa gac ata cca gct ccc cta aat ttg tat ggc 540
Pro Pro Tyr Arg Glu Glu Asp Ile Pro Ala Pro Leu Asn Leu Tyr Gly
145 150 155 160 aaa aca aaa tta gat gga gaa aag gct gtc ctg gag aac aat cta gga 588
Lys Thr Lys Leu Asp Gly Glu Lys Ala Val Leu Glu Asn Asn Leu Gly
165 170 175 gct gct gtt ttg agg att cct att ctg tat ggg gaa gtt gaa aag ctc 636
Ala Ala Val Leu Arg Ile Pro Ile Leu Tyr Gly Glu Val Glu Lys Leu
180 185 190 gaa gaa agt gct gtg act gtt atg ttt gat aaa gtg cag ttc agc aac 684
Glu Glu Ser Ala Val Thr Val Met Phe Asp Lys Val Gln Phe Ser Asn
195 200 205 aag tca gca aac atg gat cac tgg cag cag agg ttc ccc aca cat gtc 732
Lys Ser Ala Asn Met Asp His Trp Gln Gln Arg Phe Pro Thr His Val
210 215 220

```
aaa gat gtg gcc act gtg tgc cgg cag cta gca gag aag aga atg ctg      780
Lys Asp Val Ala Thr Val Cys Arg Gln Leu Ala Glu Lys Arg Met Leu
225                 230                 235                 240

gat cca tca att aag gga acc ttt cac tgg tct ggc aat gaa cag atg      828
Asp Pro Ser Ile Lys Gly Thr Phe His Trp Ser Gly Asn Glu Gln Met
                245                 250                 255

act aag tat gaa atg gca tgt gca att gca gat gcc ttc aac ctc ccc      876
Thr Lys Tyr Glu Met Ala Cys Ala Ile Ala Asp Ala Phe Asn Leu Pro
            260                 265                 270

agc agt cac tta aga cct att act gac agc cct gtc cta gga gca caa      924
Ser Ser His Leu Arg Pro Ile Thr Asp Ser Pro Val Leu Gly Ala Gln
        275                 280                 285

cgt ccg aga aat gct cag ctt gac tgc tcc aaa ttg gag acc ttg ggc      972
Arg Pro Arg Asn Ala Gln Leu Asp Cys Ser Lys Leu Glu Thr Leu Gly
    290                 295                 300

att ggc caa cga aca cca ttt cga att gga atc aaa gaa tca ctt tgg     1020
Ile Gly Gln Arg Thr Pro Phe Arg Ile Gly Ile Lys Glu Ser Leu Trp
305                 310                 315                 320

cct ttc ctc att gac aag aga tgg aga caa acg gtc ttt cat             1062
Pro Phe Leu Ile Asp Lys Arg Trp Arg Gln Thr Val Phe His
                325                 330

tagtctattt gtgttgggtt cttttttttt taaatgaaaa gtatagtatg tggcactttt   1122

taaagaacaa aggaaatagt tttgtatgag tactttaatt gtgactctta ggatctttca   1182

ggtaaatgat gctcttgcac tagtgaaatt gtctaaagaa actaaagggc agtcatgccc   1242

tgtttgcagt aatttttctt tttatcattt tgtttgtcct ggctaaactt ggagtttgag   1302

tatagtaaat tatgatcctt aaatatttga gagtcaggat gaagcagacc tgctgtagac   1362

ttttcagatg aaattgttca ttctcgtaac ctccatattt tcaggatttt tgaagctgtt   1422

gaccttttca tgttgattat tttaaattgt gtgaaatagt ataaaaatca ttggtgtaca   1482

ttatttgctt tgcctgagct cagatcaaaa tgtttgaaga aaggaacttt atttttgcaa   1542

gttacgtaca gtttttatgc ttgagatatt tcaacatgtt atgtatattg gaacttctac   1602

agcttgatgc ctcctgcttt tatagcagtt tatggggagc acttgaaaga gcgtgtgtac   1662

atgtattttt tttctaggca aacattgaat gcaaacgtgt atttttttaa tataaatata   1722

taactgtcct tttcatccca tgttgccgct aagtgatatt tcatatgtgt ggttatactc   1782

ataataatgg gccttgtaag ccttttcacc attcatgaat aataataaat atgtactgct   1842

ggcatgtaaa aaaaaaaaaa aaaaa                                         1867


<210> SEQ ID NO 22
<211> LENGTH: 334
<212> TYPE: PRT
<213> ORGANISM: Homo sapiens

<400> SEQUENCE: 22

Met Val Gly Arg Glu Lys Glu Leu Ser Ile His Phe Val Pro Gly Ser
1               5                   10                  15

Cys Arg Leu Val Glu Glu Glu Val Asn Ile Pro Asn Arg Arg Val Leu
            20                  25                  30

Val Thr Gly Ala Thr Gly Leu Leu Gly Arg Ala Val His Lys Glu Phe
        35                  40                  45

Gln Gln Asn Asn Trp His Ala Val Gly Cys Gly Phe Arg Arg Ala Arg
    50                  55                  60

Pro Lys Phe Glu Gln Val Asn Leu Leu Asp Ser Asn Ala Val His His
65                  70                  75                  80
```

```
Ile Ile His Asp Phe Gln Pro His Val Ile Val His Cys Ala Ala Glu
                85                  90                  95

Arg Arg Pro Asp Val Val Glu Asn Gln Pro Asp Ala Ala Ser Gln Leu
            100                 105                 110

Asn Val Asp Ala Ser Gly Asn Leu Ala Lys Glu Ala Ala Ala Val Gly
        115                 120                 125

Ala Phe Leu Ile Tyr Ile Ser Ser Asp Tyr Val Phe Asp Gly Thr Asn
    130                 135                 140

Pro Pro Tyr Arg Glu Glu Asp Ile Pro Ala Pro Leu Asn Leu Tyr Gly
145                 150                 155                 160

Lys Thr Lys Leu Asp Gly Glu Lys Ala Val Leu Glu Asn Asn Leu Gly
                165                 170                 175

Ala Ala Val Leu Arg Ile Pro Ile Leu Tyr Gly Glu Val Glu Lys Leu
            180                 185                 190

Glu Glu Ser Ala Val Thr Val Met Phe Asp Lys Val Gln Phe Ser Asn
        195                 200                 205

Lys Ser Ala Asn Met Asp His Trp Gln Gln Arg Phe Pro Thr His Val
    210                 215                 220

Lys Asp Val Ala Thr Val Cys Arg Gln Leu Ala Glu Lys Arg Met Leu
225                 230                 235                 240

Asp Pro Ser Ile Lys Gly Thr Phe His Trp Ser Gly Asn Glu Gln Met
                245                 250                 255

Thr Lys Tyr Glu Met Ala Cys Ala Ile Ala Asp Ala Phe Asn Leu Pro
            260                 265                 270

Ser Ser His Leu Arg Pro Ile Thr Asp Ser Pro Val Leu Gly Ala Gln
        275                 280                 285

Arg Pro Arg Asn Ala Gln Leu Asp Cys Ser Lys Leu Glu Thr Leu Gly
    290                 295                 300

Ile Gly Gln Arg Thr Pro Phe Arg Ile Gly Ile Lys Glu Ser Leu Trp
305                 310                 315                 320

Pro Phe Leu Ile Asp Lys Arg Trp Arg Gln Thr Val Phe His
                325                 330


<210> SEQ ID NO 23
<211> LENGTH: 1867
<212> TYPE: DNA
<213> ORGANISM: Homo sapiens
<220> FEATURE:
<221> NAME/KEY: CDS
<222> LOCATION: (61)..(1062)

<400> SEQUENCE: 23

cgtcgatcct gggttggagg aggtggcggc cgctgaggct gcggcgtgaa gacggcgggc      60

atg gtg ggg cgg gag aaa gaa atc tct ata cac ttt gtt ccc ggg agc      108
Met Val Gly Arg Glu Lys Glu Ile Ser Ile His Phe Val Pro Gly Ser
1               5                   10                  15

tgt cgg ctg gtg gag gag gaa gtt aac atc cct aat agg agg gtt ctg      156
Cys Arg Leu Val Glu Glu Glu Val Asn Ile Pro Asn Arg Arg Val Leu
            20                  25                  30

gtt act ggt gcc act ggg ctt ctt ggc aga gct gta cac aaa gaa ttt      204
Val Thr Gly Ala Thr Gly Leu Leu Gly Arg Ala Val His Lys Glu Phe
        35                  40                  45

cag cag aat aat tgg cat gca gtt ggc tgt ggt ttc aga aga gca aga      252
Gln Gln Asn Asn Trp His Ala Val Gly Cys Gly Phe Arg Arg Ala Arg
    50                  55                  60

cca aaa ttt gaa cag gtt aat ctg ttg gat tct aat gca gtt cat cac      300
Pro Lys Phe Glu Gln Val Asn Leu Leu Asp Ser Asn Ala Val His His
65                  70                  75                  80
```

```
atc att cat gat ttt cag ccc cat gtt ata gta cat tgt gca gca gag      348
Ile Ile His Asp Phe Gln Pro His Val Ile Val His Cys Ala Ala Glu
                85                  90                  95

aga aga cca gat gtt gta gaa aat cag cca gat gct gcc tct caa ctt      396
Arg Arg Pro Asp Val Val Glu Asn Gln Pro Asp Ala Ala Ser Gln Leu
            100                 105                 110

aat gtg gat gct tct ggg aat tta gca aag gaa gca gct gct gtt gga      444
Asn Val Asp Ala Ser Gly Asn Leu Ala Lys Glu Ala Ala Ala Val Gly
        115                 120                 125

gca ttt ctc atc tac att agc tca gat tat gta ttt gat gga aca aat      492
Ala Phe Leu Ile Tyr Ile Ser Ser Asp Tyr Val Phe Asp Gly Thr Asn
    130                 135                 140

cca cct tac aga gag gaa gac ata cca gct ccc cta aat ttg tat ggc      540
Pro Pro Tyr Arg Glu Glu Asp Ile Pro Ala Pro Leu Asn Leu Tyr Gly
145                 150                 155                 160

aaa aca aaa tta gat gga gaa aag gct gtc ctg gag aac aat cta gga      588
Lys Thr Lys Leu Asp Gly Glu Lys Ala Val Leu Glu Asn Asn Leu Gly
                165                 170                 175

gct gct gtt ttg agg att cct att ctg tat ggg gaa gtt gaa aag ctc      636
Ala Ala Val Leu Arg Ile Pro Ile Leu Tyr Gly Glu Val Glu Lys Leu
            180                 185                 190

gaa gaa agt gct gtg act gtt atg ttt gat aaa gtg cag ttc agc aac      684
Glu Glu Ser Ala Val Thr Val Met Phe Asp Lys Val Gln Phe Ser Asn
        195                 200                 205

aag tca gca aac atg gat cac tgg cag cag agg ttc ccc aca cat gtc      732
Lys Ser Ala Asn Met Asp His Trp Gln Gln Arg Phe Pro Thr His Val
    210                 215                 220

aaa gat gtg gcc act gtg tgc cgg cag cta gca gag aag aga atg ctg      780
Lys Asp Val Ala Thr Val Cys Arg Gln Leu Ala Glu Lys Arg Met Leu
225                 230                 235                 240

gat cca tca att aag gga acc ttt cac tgg tct ggc aat gaa cag atg      828
Asp Pro Ser Ile Lys Gly Thr Phe His Trp Ser Gly Asn Glu Gln Met
                245                 250                 255

act aag tat gaa atg gca tgt gca att gca gat gcc ttc aac ctc ccc      876
Thr Lys Tyr Glu Met Ala Cys Ala Ile Ala Asp Ala Phe Asn Leu Pro
            260                 265                 270

agc agt cac tta aga cct att act gac agc cct gtc cta gga gca caa      924
Ser Ser His Leu Arg Pro Ile Thr Asp Ser Pro Val Leu Gly Ala Gln
        275                 280                 285

cgt ccg aga aat gct cag ctt gac tgc tcc aaa ttg gag acc ttg ggc      972
Arg Pro Arg Asn Ala Gln Leu Asp Cys Ser Lys Leu Glu Thr Leu Gly
    290                 295                 300

att ggc caa cga aca cca ttt cga att gga atc aaa gaa tca ctt tgg     1020
Ile Gly Gln Arg Thr Pro Phe Arg Ile Gly Ile Lys Glu Ser Leu Trp
305                 310                 315                 320

cct ttc ctc att gac aag aga tgg aga caa acg gtc ttt cat             1062
Pro Phe Leu Ile Asp Lys Arg Trp Arg Gln Thr Val Phe His
                325                 330

tagtctattt gtgttgggtt cttttttttt taaatgaaaa gtatagtatg tggcactttt   1122

taaagaacaa aggaaatagt tttgtatgag tactttaatt gtgactctta ggatctttca   1182

ggtaaatgat gctcttgcac tagtgaaatt gtctaaagaa actaaagggc agtcatgccc   1242

tgtttgcagt aatttttctt tttatcattt tgtttgtcct ggctaaactt ggagtttgag   1302

tatagtaaat tatgatcctt aaatatttga gagtcaggat gaagcagacc tgctgtagac   1362

ttttcagatg aaattgttca ttctcgtaac ctccatattt tcaggatttt tgaagctgtt   1422

gacctttca tgttgattat tttaaattgt gtgaaatagt ataaaaatca ttggtgtaca    1482

ttatttgctt tgcctgagct cagatcaaaa tgtttgaaga aaggaacttt atttttgcaa   1542
```

```
gttacgtaca gtttttatgc ttgagatatt tcaacatgtt atgtatattg gaacttctac   1602

agcttgatgc ctcctgcttt tatagcagtt tatggggagc acttgaaaga gcgtgtgtac   1662

atgtattttt tttctaggca aacattgaat gcaaacgtgt atttttttaa tataaatata   1722

taactgtcct tttcatccca tgttgccgct aagtgatatt tcatatgtgt ggttatactc   1782

ataataatgg gccttgtaag ccttttcacc attcatgaat aataataaat atgtactgct   1842

ggcatgtaaa aaaaaaaaaa aaaaa                                          1867


<210> SEQ ID NO 24
<211> LENGTH: 334
<212> TYPE: PRT
<213> ORGANISM: Homo sapiens

<400> SEQUENCE: 24

Met Val Gly Arg Glu Lys Glu Ile Ser Ile His Phe Val Pro Gly Ser
1               5                   10                  15

Cys Arg Leu Val Glu Glu Glu Val Asn Ile Pro Asn Arg Arg Val Leu
            20                  25                  30

Val Thr Gly Ala Thr Gly Leu Leu Gly Arg Ala Val His Lys Glu Phe
        35                  40                  45

Gln Gln Asn Asn Trp His Ala Val Gly Cys Gly Phe Arg Arg Ala Arg
    50                  55                  60

Pro Lys Phe Glu Gln Val Asn Leu Leu Asp Ser Asn Ala Val His His
65                  70                  75                  80

Ile Ile His Asp Phe Gln Pro His Val Ile Val His Cys Ala Ala Glu
                85                  90                  95

Arg Arg Pro Asp Val Val Glu Asn Gln Pro Asp Ala Ala Ser Gln Leu
            100                 105                 110

Asn Val Asp Ala Ser Gly Asn Leu Ala Lys Glu Ala Ala Ala Val Gly
        115                 120                 125

Ala Phe Leu Ile Tyr Ile Ser Ser Asp Tyr Val Phe Asp Gly Thr Asn
    130                 135                 140

Pro Pro Tyr Arg Glu Glu Asp Ile Pro Ala Pro Leu Asn Leu Tyr Gly
145                 150                 155                 160

Lys Thr Lys Leu Asp Gly Glu Lys Ala Val Leu Glu Asn Asn Leu Gly
                165                 170                 175

Ala Ala Val Leu Arg Ile Pro Ile Leu Tyr Gly Glu Val Glu Lys Leu
            180                 185                 190

Glu Glu Ser Ala Val Thr Val Met Phe Asp Lys Val Gln Phe Ser Asn
        195                 200                 205

Lys Ser Ala Asn Met Asp His Trp Gln Gln Arg Phe Pro Thr His Val
    210                 215                 220

Lys Asp Val Ala Thr Val Cys Arg Gln Leu Ala Glu Lys Arg Met Leu
225                 230                 235                 240

Asp Pro Ser Ile Lys Gly Thr Phe His Trp Ser Gly Asn Glu Gln Met
                245                 250                 255

Thr Lys Tyr Glu Met Ala Cys Ala Ile Ala Asp Ala Phe Asn Leu Pro
            260                 265                 270

Ser Ser His Leu Arg Pro Ile Thr Asp Ser Pro Val Leu Gly Ala Gln
        275                 280                 285

Arg Pro Arg Asn Ala Gln Leu Asp Cys Ser Lys Leu Glu Thr Leu Gly
    290                 295                 300

Ile Gly Gln Arg Thr Pro Phe Arg Ile Gly Ile Lys Glu Ser Leu Trp
305                 310                 315                 320
```

```
Pro Phe Leu Ile Asp Lys Arg Trp Arg Gln Thr Val Phe His
                325                 330


<210> SEQ ID NO 25
<211> LENGTH: 1867
<212> TYPE: DNA
<213> ORGANISM: Homo sapiens
<220> FEATURE:
<221> NAME/KEY: CDS
<222> LOCATION: (61)..(1062)

<400> SEQUENCE: 25

cgtcgatcct gggttggagg aggtggcggc cgctgaggct gcggcgtgaa gacggcgggc      60

atg gtg ggg cgg gag aaa gaa ctg tct ata cac ttt gtt ccc ggg agc      108
Met Val Gly Arg Glu Lys Glu Leu Ser Ile His Phe Val Pro Gly Ser
1               5                   10                  15

tgt cgg ctg gtg gag gag gaa gtt aac atc cct aat agg agg gtt atc      156
Cys Arg Leu Val Glu Glu Glu Val Asn Ile Pro Asn Arg Arg Val Ile
            20                  25                  30

gtt act ggt gcc act ggg ctt ctt ggc aga gct gta cac aaa gaa ttt      204
Val Thr Gly Ala Thr Gly Leu Leu Gly Arg Ala Val His Lys Glu Phe
        35                  40                  45

cag cag aat aat tgg cat gca gtt ggc tgt ggt ttc aga aga gca aga      252
Gln Gln Asn Asn Trp His Ala Val Gly Cys Gly Phe Arg Arg Ala Arg
    50                  55                  60

cca aaa ttt gaa cag gtt aat ctg ttg gat tct aat gca gtt cat cac      300
Pro Lys Phe Glu Gln Val Asn Leu Leu Asp Ser Asn Ala Val His His
65                  70                  75                  80

atc att cat gat ttt cag ccc cat gtt ata gta cat tgt gca gca gag      348
Ile Ile His Asp Phe Gln Pro His Val Ile Val His Cys Ala Ala Glu
                85                  90                  95

aga aga cca gat gtt gta gaa aat cag cca gat gct gcc tct caa ctt      396
Arg Arg Pro Asp Val Val Glu Asn Gln Pro Asp Ala Ala Ser Gln Leu
            100                 105                 110

aat gtg gat gct tct ggg aat tta gca aag gaa gca gct gct gtt gga      444
Asn Val Asp Ala Ser Gly Asn Leu Ala Lys Glu Ala Ala Ala Val Gly
        115                 120                 125

gca ttt ctc atc tac att agc tca gat tat gta ttt gat gga aca aat      492
Ala Phe Leu Ile Tyr Ile Ser Ser Asp Tyr Val Phe Asp Gly Thr Asn
    130                 135                 140

cca cct tac aga gag gaa gac ata cca gct ccc cta aat ttg tat ggc      540
Pro Pro Tyr Arg Glu Glu Asp Ile Pro Ala Pro Leu Asn Leu Tyr Gly
145                 150                 155                 160

aaa aca aaa tta gat gga gaa aag gct gtc ctg gag aac aat cta gga      588
Lys Thr Lys Leu Asp Gly Glu Lys Ala Val Leu Glu Asn Asn Leu Gly
                165                 170                 175

gct gct gtt ttg agg att cct att ctg tat ggg gaa gtt gaa aag ctc      636
Ala Ala Val Leu Arg Ile Pro Ile Leu Tyr Gly Glu Val Glu Lys Leu
            180                 185                 190

gaa gaa agt gct gtg act gtt atg ttt gat aaa gtg cag ttc agc aac      684
Glu Glu Ser Ala Val Thr Val Met Phe Asp Lys Val Gln Phe Ser Asn
        195                 200                 205

aag tca gca aac atg gat cac tgg cag cag agg ttc ccc aca cat gtc      732
Lys Ser Ala Asn Met Asp His Trp Gln Gln Arg Phe Pro Thr His Val
    210                 215                 220

aaa gat gtg gcc act gtg tgc cgg cag cta gca gag aag aga atg ctg      780
Lys Asp Val Ala Thr Val Cys Arg Gln Leu Ala Glu Lys Arg Met Leu
225                 230                 235                 240

gat cca tca att aag gga acc ttt cac tgg tct ggc aat gaa cag atg      828
Asp Pro Ser Ile Lys Gly Thr Phe His Trp Ser Gly Asn Glu Gln Met
                245                 250                 255
```

-continued

```
act aag tat gaa atg gca tgt gca att gca gat gcc ttc aac ctc ccc      876
Thr Lys Tyr Glu Met Ala Cys Ala Ile Ala Asp Ala Phe Asn Leu Pro
            260                 265                 270 agc agt cac tta aga cct att act gac agc cct gtc cta gga gca caa      924
Ser Ser His Leu Arg Pro Ile Thr Asp Ser Pro Val Leu Gly Ala Gln
        275                 280                 285 cgt ccg aga aat gct cag ctt gac tgc tcc aaa ttg gag acc ttg ggc      972
Arg Pro Arg Asn Ala Gln Leu Asp Cys Ser Lys Leu Glu Thr Leu Gly
    290                 295                 300 att ggc caa cga aca cca ttt cga att gga atc aaa gaa tca ctt tgg     1020
Ile Gly Gln Arg Thr Pro Phe Arg Ile Gly Ile Lys Glu Ser Leu Trp
305                 310                 315                 320 cct ttc ctc att gac aag aga tgg aga caa acg gtc ttt cat             1062
Pro Phe Leu Ile Asp Lys Arg Trp Arg Gln Thr Val Phe His
                325                 330 tagtctattt gtgttgggtt cttttttttt taaatgaaaa gtatagtatg tggcactttt   1122
taaagaacaa aggaaatagt tttgtatgag tactttaatt gtgactctta ggatctttca   1182
ggtaaatgat gctcttgcac tagtgaaatt gtctaaagaa actaaagggc agtcatgccc   1242
tgtttgcagt aatttttctt tttatcattt tgtttgtcct ggctaaactt ggagtttgag   1302
tatagtaaat tatgatcctt aaatatttga gagtcaggat gaagcagacc tgctgtagac   1362
ttttcagatg aaattgttca ttctcgtaac ctccatattt tcaggatttt tgaagctgtt   1422
gaccttttca tgttgattat tttaaattgt gtgaaatagt ataaaaatca ttggtgtaca   1482
ttatttgctt tgcctgagct cagatcaaaa tgtttgaaga aaggaacttt atttttgcaa   1542
gttacgtaca gtttttatgc ttgagatatt tcaacatgtt atgtatattg gaacttctac   1602
agcttgatgc ctcctgcttt tatagcagtt tatggggagc acttgaaaga gcgtgtgtac   1662
atgtattttt tttctaggca aacattgaat gcaaacgtgt atttttttaa tataaatata   1722
taactgtcct tttcatccca tgttgccgct aagtgatatt tcatatgtgt ggttatactc   1782
ataataatgg gccttgtaag ccttttcacc attcatgaat aataataaat atgtactgct   1842
ggcatgtaaa aaaaaaaaaa aaaaa                                          1867

<210> SEQ ID NO 26
<211> LENGTH: 334
<212> TYPE: PRT
<213> ORGANISM: Homo sapiens

<400> SEQUENCE: 26

Met Val Gly Arg Glu Lys Glu Leu Ser Ile His Phe Val Pro Gly Ser
1               5                   10                  15

Cys Arg Leu Val Glu Glu Glu Val Asn Ile Pro Asn Arg Arg Val Ile
            20                  25                  30

Val Thr Gly Ala Thr Gly Leu Leu Gly Arg Ala Val His Lys Glu Phe
        35                  40                  45

Gln Gln Asn Asn Trp His Ala Val Gly Cys Gly Phe Arg Arg Ala Arg
    50                  55                  60

Pro Lys Phe Glu Gln Val Asn Leu Leu Asp Ser Asn Ala Val His His
65                  70                  75                  80

Ile Ile His Asp Phe Gln Pro His Val Ile Val His Cys Ala Ala Glu
                85                  90                  95

Arg Arg Pro Asp Val Val Glu Asn Gln Pro Asp Ala Ala Ser Gln Leu
            100                 105                 110

Asn Val Asp Ala Ser Gly Asn Leu Ala Lys Glu Ala Ala Ala Val Gly
        115                 120                 125
```

```
Ala Phe Leu Ile Tyr Ile Ser Ser Asp Tyr Val Phe Asp Gly Thr Asn
    130                 135                 140

Pro Pro Tyr Arg Glu Glu Asp Ile Pro Ala Pro Leu Asn Leu Tyr Gly
145                 150                 155                 160

Lys Thr Lys Leu Asp Gly Glu Lys Ala Val Leu Glu Asn Asn Leu Gly
                165                 170                 175

Ala Ala Val Leu Arg Ile Pro Ile Leu Tyr Gly Glu Val Glu Lys Leu
            180                 185                 190

Glu Glu Ser Ala Val Thr Val Met Phe Asp Lys Val Gln Phe Ser Asn
        195                 200                 205

Lys Ser Ala Asn Met Asp His Trp Gln Gln Arg Phe Pro Thr His Val
    210                 215                 220

Lys Asp Val Ala Thr Val Cys Arg Gln Leu Ala Glu Lys Arg Met Leu
225                 230                 235                 240

Asp Pro Ser Ile Lys Gly Thr Phe His Trp Ser Gly Asn Glu Gln Met
                245                 250                 255

Thr Lys Tyr Glu Met Ala Cys Ala Ile Ala Asp Ala Phe Asn Leu Pro
            260                 265                 270

Ser Ser His Leu Arg Pro Ile Thr Asp Ser Pro Val Leu Gly Ala Gln
        275                 280                 285

Arg Pro Arg Asn Ala Gln Leu Asp Cys Ser Lys Leu Glu Thr Leu Gly
    290                 295                 300

Ile Gly Gln Arg Thr Pro Phe Arg Ile Gly Ile Lys Glu Ser Leu Trp
305                 310                 315                 320

Pro Phe Leu Ile Asp Lys Arg Trp Arg Gln Thr Val Phe His
                325                 330


<210> SEQ ID NO 27
<211> LENGTH: 1867
<212> TYPE: DNA
<213> ORGANISM: Homo sapiens
<220> FEATURE:
<221> NAME/KEY: CDS
<222> LOCATION: (61)..(1062)

<400> SEQUENCE: 27

cgtcgatcct gggttggagg aggtggcggc cgctgaggct gcggcgtgaa gacggcgggc      60

atg gtg ggg cgg gag aaa gaa ctg tct ata cac ttt gtt ccc ggg agc      108
Met Val Gly Arg Glu Lys Glu Leu Ser Ile His Phe Val Pro Gly Ser
1               5                   10                  15

tgt cgg ctg gtg gag gag gaa gtt aac atc cct aat agg agg gtt ctg      156
Cys Arg Leu Val Glu Glu Glu Val Asn Ile Pro Asn Arg Arg Val Leu
            20                  25                  30

gtt act ggt gcc act ggg ctt ctt ggc aga gct gta cac aaa gaa ttt      204
Val Thr Gly Ala Thr Gly Leu Leu Gly Arg Ala Val His Lys Glu Phe
        35                  40                  45

cag cag aat aat tgg cat gca gtt ggc tgt ggt ttc aga aga gca aga      252
Gln Gln Asn Asn Trp His Ala Val Gly Cys Gly Phe Arg Arg Ala Arg
    50                  55                  60

cca aaa ttt gaa cag gtt aat ctg ttg gat tct aat gca gtt cat cac      300
Pro Lys Phe Glu Gln Val Asn Leu Leu Asp Ser Asn Ala Val His His
65                  70                  75                  80

atc att cat gat ttt cag ccc cat gtt ata gta cat tgt gca gca gag      348
Ile Ile His Asp Phe Gln Pro His Val Ile Val His Cys Ala Ala Glu
                85                  90                  95

aga aga cca gat gtt gta gaa aat cag cca gat gct gcc tct caa ctt      396
Arg Arg Pro Asp Val Val Glu Asn Gln Pro Asp Ala Ala Ser Gln Leu
            100                 105                 110
```

-continued

```
aat gtg gat gct tct ggg aat tta gca aag gaa gca gct gct gtt gga      444
Asn Val Asp Ala Ser Gly Asn Leu Ala Lys Glu Ala Ala Ala Val Gly
        115                 120                 125

gca ttt ctc atc tac att agc tca gat tat gta ttt gat gga aca aat      492
Ala Phe Leu Ile Tyr Ile Ser Ser Asp Tyr Val Phe Asp Gly Thr Asn
    130                 135                 140

cca cct tac aga gag gaa gac ata cca gct ccc cta aat ttg tat ggc      540
Pro Pro Tyr Arg Glu Glu Asp Ile Pro Ala Pro Leu Asn Leu Tyr Gly
145                 150                 155                 160

aaa aca aaa tta gat gga gaa aag gct gtc ctg gag aac aat atc gga      588
Lys Thr Lys Leu Asp Gly Glu Lys Ala Val Leu Glu Asn Asn Ile Gly
                165                 170                 175

gct gct gtt ttg agg att cct att ctg tat ggg gaa gtt gaa aag ctc      636
Ala Ala Val Leu Arg Ile Pro Ile Leu Tyr Gly Glu Val Glu Lys Leu
            180                 185                 190

gaa gaa agt gct gtg act gtt atg ttt gat aaa gtg cag ttc agc aac      684
Glu Glu Ser Ala Val Thr Val Met Phe Asp Lys Val Gln Phe Ser Asn
        195                 200                 205

aag tca gca aac atg gat cac tgg cag cag agg ttc ccc aca cat gtc      732
Lys Ser Ala Asn Met Asp His Trp Gln Gln Arg Phe Pro Thr His Val
    210                 215                 220

aaa gat gtg gcc act gtg tgc cgg cag cta gca gag aag aga atg ctg      780
Lys Asp Val Ala Thr Val Cys Arg Gln Leu Ala Glu Lys Arg Met Leu
225                 230                 235                 240

gat cca tca att aag gga acc ttt cac tgg tct ggc aat gaa cag atg      828
Asp Pro Ser Ile Lys Gly Thr Phe His Trp Ser Gly Asn Glu Gln Met
                245                 250                 255

act aag tat gaa atg gca tgt gca att gca gat gcc ttc aac ctc ccc      876
Thr Lys Tyr Glu Met Ala Cys Ala Ile Ala Asp Ala Phe Asn Leu Pro
            260                 265                 270

agc agt cac tta aga cct att act gac agc cct gtc cta gga gca caa      924
Ser Ser His Leu Arg Pro Ile Thr Asp Ser Pro Val Leu Gly Ala Gln
        275                 280                 285

cgt ccg aga aat gct cag ctt gac tgc tcc aaa ttg gag acc ttg ggc      972
Arg Pro Arg Asn Ala Gln Leu Asp Cys Ser Lys Leu Glu Thr Leu Gly
    290                 295                 300

att ggc caa cga aca cca ttt cga att gga atc aaa gaa tca ctt tgg     1020
Ile Gly Gln Arg Thr Pro Phe Arg Ile Gly Ile Lys Glu Ser Leu Trp
305                 310                 315                 320

cct ttc ctc att gac aag aga tgg aga caa acg gtc ttt cat             1062
Pro Phe Leu Ile Asp Lys Arg Trp Arg Gln Thr Val Phe His
                325                 330

tagtctattt gtgttgggtt cttttttttt taaatgaaaa gtatagtatg tggcactttt   1122

taaagaacaa aggaaatagt tttgtatgag tactttaatt gtgactctta ggatctttca   1182

ggtaaatgat gctcttgcac tagtgaaatt gtctaaagaa actaaagggc agtcatgccc   1242

tgtttgcagt aatttttctt tttatcattt tgtttgtcct ggctaaactt ggagtttgag   1302

tatagtaaat tatgatcctt aaatatttga gagtcaggat gaagcagacc tgctgtagac   1362

ttttcagatg aaattgttca ttctcgtaac ctccatattt tcaggatttt tgaagctgtt   1422

gacctttca tgttgattat tttaaattgt gtgaaatagt ataaaaatca ttggtgtaca   1482

ttatttgctt tgcctgagct cagatcaaaa tgtttgaaga aaggaacttt atttttgcaa   1542

gttacgtaca gtttttatgc ttgagatatt tcaacatgtt atgtatattg gaacttctac   1602

agcttgatgc ctcctgcttt tatagcagtt tatggggagc acttgaaaga gcgtgtgtac   1662

atgtattttt tttctaggca aacattgaat gcaaacgtgt atttttttaa tataaatata   1722

taactgtcct tttcatccca tgttgccgct aagtgatatt tcatatgtgt ggttatactc   1782
```

```
ataataatgg gccttgtaag ccttttcacc attcatgaat aataataaat atgtactgct   1842

ggcatgtaaa aaaaaaaaaa aaaaa                                         1867


<210> SEQ ID NO 28
<211> LENGTH: 334
<212> TYPE: PRT
<213> ORGANISM: Homo sapiens

<400> SEQUENCE: 28

Met Val Gly Arg Glu Lys Glu Leu Ser Ile His Phe Val Pro Gly Ser
1               5                   10                  15

Cys Arg Leu Val Glu Glu Glu Val Asn Ile Pro Asn Arg Arg Val Leu
            20                  25                  30

Val Thr Gly Ala Thr Gly Leu Leu Gly Arg Ala Val His Lys Glu Phe
        35                  40                  45

Gln Gln Asn Asn Trp His Ala Val Gly Cys Gly Phe Arg Arg Ala Arg
    50                  55                  60

Pro Lys Phe Glu Gln Val Asn Leu Leu Asp Ser Asn Ala Val His His
65                  70                  75                  80

Ile Ile His Asp Phe Gln Pro His Val Ile Val His Cys Ala Ala Glu
                85                  90                  95

Arg Arg Pro Asp Val Val Glu Asn Gln Pro Asp Ala Ala Ser Gln Leu
            100                 105                 110

Asn Val Asp Ala Ser Gly Asn Leu Ala Lys Glu Ala Ala Ala Val Gly
        115                 120                 125

Ala Phe Leu Ile Tyr Ile Ser Ser Asp Tyr Val Phe Asp Gly Thr Asn
    130                 135                 140

Pro Pro Tyr Arg Glu Glu Asp Ile Pro Ala Pro Leu Asn Leu Tyr Gly
145                 150                 155                 160

Lys Thr Lys Leu Asp Gly Glu Lys Ala Val Leu Glu Asn Asn Ile Gly
                165                 170                 175

Ala Ala Val Leu Arg Ile Pro Ile Leu Tyr Gly Glu Val Glu Lys Leu
            180                 185                 190

Glu Glu Ser Ala Val Thr Val Met Phe Asp Lys Val Gln Phe Ser Asn
        195                 200                 205

Lys Ser Ala Asn Met Asp His Trp Gln Gln Arg Phe Pro Thr His Val
    210                 215                 220

Lys Asp Val Ala Thr Val Cys Arg Gln Leu Ala Glu Lys Arg Met Leu
225                 230                 235                 240

Asp Pro Ser Ile Lys Gly Thr Phe His Trp Ser Gly Asn Glu Gln Met
                245                 250                 255

Thr Lys Tyr Glu Met Ala Cys Ala Ile Ala Asp Ala Phe Asn Leu Pro
            260                 265                 270

Ser Ser His Leu Arg Pro Ile Thr Asp Ser Pro Val Leu Gly Ala Gln
        275                 280                 285

Arg Pro Arg Asn Ala Gln Leu Asp Cys Ser Lys Leu Glu Thr Leu Gly
    290                 295                 300

Ile Gly Gln Arg Thr Pro Phe Arg Ile Gly Ile Lys Glu Ser Leu Trp
305                 310                 315                 320

Pro Phe Leu Ile Asp Lys Arg Trp Arg Gln Thr Val Phe His
                325                 330


<210> SEQ ID NO 29
<211> LENGTH: 1850
<212> TYPE: DNA
```

```
<213> ORGANISM: Homo sapiens
<220> FEATURE:
<221> NAME/KEY: CDS
<222> LOCATION: (61)..(1062)

<400> SEQUENCE: 29

cgtcgatcct gggttggagg aggtggcggc cgctgaggct gcggcgtgaa gacggcgggc      60

atg gtg ggg cgg gag aaa gaa ctg tct ata cac ttt gtt ccc ggg agc       108
Met Val Gly Arg Glu Lys Glu Leu Ser Ile His Phe Val Pro Gly Ser
1               5                   10                  15

tgt cgg ctg gtg gag gag gaa gtt aac atc cct aat agg agg gtt ctg       156
Cys Arg Leu Val Glu Glu Glu Val Asn Ile Pro Asn Arg Arg Val Leu
            20                  25                  30

gtt act ggt gcc act ggg ctt ctt ggc aga gct gta cac aaa gaa ttt       204
Val Thr Gly Ala Thr Gly Leu Leu Gly Arg Ala Val His Lys Glu Phe
        35                  40                  45

cag cag aat aat tgg cat gca gtt ggc tgt ggt ttc aga aga gca aga       252
Gln Gln Asn Asn Trp His Ala Val Gly Cys Gly Phe Arg Arg Ala Arg
    50                  55                  60

cca aaa ttt gaa cag gtt aat ctg ttg gat tct aat gca gtt cat cac       300
Pro Lys Phe Glu Gln Val Asn Leu Leu Asp Ser Asn Ala Val His His
65                  70                  75                  80

atc att cat gat ttt cag ccc cat gtt ata gta cat tgt gca gca gag       348
Ile Ile His Asp Phe Gln Pro His Val Ile Val His Cys Ala Ala Glu
                85                  90                  95

aga aga cca gat gtt gta gaa aat cag cca gat gct gcc tct caa ctt       396
Arg Arg Pro Asp Val Val Glu Asn Gln Pro Asp Ala Ala Ser Gln Leu
            100                 105                 110

aat gtg gat gct tct ggg aat tta gca aag gaa gca gct gct gtt gga       444
Asn Val Asp Ala Ser Gly Asn Leu Ala Lys Glu Ala Ala Ala Val Gly
        115                 120                 125

gca ttt ctc atc tac att agc tca gat tat gta ttt gat gga aca aat       492
Ala Phe Leu Ile Tyr Ile Ser Ser Asp Tyr Val Phe Asp Gly Thr Asn
    130                 135                 140

cca cct tac aga gag gaa gac ata cca gct ccc cta aat ttg tat ggc       540
Pro Pro Tyr Arg Glu Glu Asp Ile Pro Ala Pro Leu Asn Leu Tyr Gly
145                 150                 155                 160

aaa aca aaa tta gat gga gaa aag gct gtc ctg gag aac aat cta gga       588
Lys Thr Lys Leu Asp Gly Glu Lys Ala Val Leu Glu Asn Asn Leu Gly
                165                 170                 175

gct gct gtt ttg agg att cct att ctg tat ggg gaa gtt gaa aag ctc       636
Ala Ala Val Leu Arg Ile Pro Ile Leu Tyr Gly Glu Val Glu Lys Leu
            180                 185                 190

gaa gaa agt gct gtg act gtt atg ttt gat aaa gtg cag ttc agc aac       684
Glu Glu Ser Ala Val Thr Val Met Phe Asp Lys Val Gln Phe Ser Asn
        195                 200                 205

aag tca gca aac atg gat cac tgg cag cag agg ttc ccc aca cat gtc       732
Lys Ser Ala Asn Met Asp His Trp Gln Gln Arg Phe Pro Thr His Val
    210                 215                 220

aaa gat gtg gcc act gtg tgc cgg cag cta gca gag aag aga atg ctg       780
Lys Asp Val Ala Thr Val Cys Arg Gln Leu Ala Glu Lys Arg Met Leu
225                 230                 235                 240

gat cca tca att aag gga acc ttt cac tgg tct ggc aat gaa cag atg       828
Asp Pro Ser Ile Lys Gly Thr Phe His Trp Ser Gly Asn Glu Gln Met
                245                 250                 255

act aag tat gaa atg gca tgt gca att gca gat gcc ttc aac atc ccc       876
Thr Lys Tyr Glu Met Ala Cys Ala Ile Ala Asp Ala Phe Asn Ile Pro
            260                 265                 270

agc agt cac tta aga cct att act gac agc cct gtc cta gga gca caa       924
Ser Ser His Leu Arg Pro Ile Thr Asp Ser Pro Val Leu Gly Ala Gln
        275                 280                 285
```

-continued

```
cgt ccg aga aat gct cag ctt gac tgc tcc aaa ttg gag acc ttg ggc      972
Arg Pro Arg Asn Ala Gln Leu Asp Cys Ser Lys Leu Glu Thr Leu Gly
    290                 295                 300

att ggc caa cga aca cca ttt cga att gga atc aaa gaa tca ctt tgg     1020
Ile Gly Gln Arg Thr Pro Phe Arg Ile Gly Ile Lys Glu Ser Leu Trp
305                 310                 315                 320

cct ttc ctc att gac aag aga tgg aga caa acg gtc ttt cat             1062
Pro Phe Leu Ile Asp Lys Arg Trp Arg Gln Thr Val Phe His
                325                 330

tagtctattt gtgttgggtt cttttttttt taaatgaaaa gtatagtatg tggcactttt   1122

taaagaacaa aggaaatagt tttgtatgag tactttaatt gtgactctta ggatctttca   1182

ggtaaatgat gctcttgcac tagtgaaatt gtctaaagaa actaaagggc agtcatgccc   1242

tgtttgcagt aatttttctt tttatcattt tgtttgtcct ggctaaactt ggagtttgag   1302

tatagtaaat tatgatcctt aaatatttga gagtcaggat gaagcagacc tgctgtagac   1362

ttttcagatg aaattgttca ttctcgtaac ctccatattt tcaggatttt tgaagctgtt   1422

gaccttttca tgttgattat tttaaattgt gtgaaatagt ataaaaatca ttggtgtaca   1482

ttatttgctt tgcctgagct cagatcaaaa tgtttgaaga aaggaacttt atttttgcaa   1542

gttacgtaca gtttttatgc ttgagatatt tcaacatgtt atgtatattg gaacttctac   1602

agcttgatgc ctcctgcttt tatagcagtt tatggggagc acttgaaaga gcgtgtgtac   1662

atgtattttt tttctaggca aacattgaat gcaaacgtgt atttttttaa tataaatata   1722

taactgtcct tttcatccca tgttgccgct aagtgatatt tcatatgtgt ggttatactc   1782

ataataatgg gccttgtaag ccttttcacc attcatgaat aataataaat atgtactgct   1842

ggcatgta                                                            1850


<210> SEQ ID NO 30
<211> LENGTH: 334
<212> TYPE: PRT
<213> ORGANISM: Homo sapiens

<400> SEQUENCE: 30

Met Val Gly Arg Glu Lys Glu Leu Ser Ile His Phe Val Pro Gly Ser
1               5                   10                  15

Cys Arg Leu Val Glu Glu Glu Val Asn Ile Pro Asn Arg Arg Val Leu
            20                  25                  30

Val Thr Gly Ala Thr Gly Leu Leu Gly Arg Ala Val His Lys Glu Phe
        35                  40                  45

Gln Gln Asn Asn Trp His Ala Val Gly Cys Gly Phe Arg Arg Ala Arg
    50                  55                  60

Pro Lys Phe Glu Gln Val Asn Leu Leu Asp Ser Asn Ala Val His His
65                  70                  75                  80

Ile Ile His Asp Phe Gln Pro His Val Ile Val His Cys Ala Ala Glu
                85                  90                  95

Arg Arg Pro Asp Val Val Glu Asn Gln Pro Asp Ala Ala Ser Gln Leu
            100                 105                 110

Asn Val Asp Ala Ser Gly Asn Leu Ala Lys Glu Ala Ala Ala Val Gly
        115                 120                 125

Ala Phe Leu Ile Tyr Ile Ser Ser Asp Tyr Val Phe Asp Gly Thr Asn
    130                 135                 140

Pro Pro Tyr Arg Glu Glu Asp Ile Pro Ala Pro Leu Asn Leu Tyr Gly
145                 150                 155                 160

Lys Thr Lys Leu Asp Gly Glu Lys Ala Val Leu Glu Asn Asn Leu Gly
```

-continued

```
                165                 170                 175

Ala Ala Val Leu Arg Ile Pro Ile Leu Tyr Gly Glu Val Glu Lys Leu
            180                 185                 190

Glu Glu Ser Ala Val Thr Val Met Phe Asp Lys Val Gln Phe Ser Asn
        195                 200                 205

Lys Ser Ala Asn Met Asp His Trp Gln Gln Arg Phe Pro Thr His Val
    210                 215                 220

Lys Asp Val Ala Thr Val Cys Arg Gln Leu Ala Glu Lys Arg Met Leu
225                 230                 235                 240

Asp Pro Ser Ile Lys Gly Thr Phe His Trp Ser Gly Asn Glu Gln Met
                245                 250                 255

Thr Lys Tyr Glu Met Ala Cys Ala Ile Ala Asp Ala Phe Asn Ile Pro
            260                 265                 270

Ser Ser His Leu Arg Pro Ile Thr Asp Ser Pro Val Leu Gly Ala Gln
        275                 280                 285

Arg Pro Arg Asn Ala Gln Leu Asp Cys Ser Lys Leu Glu Thr Leu Gly
    290                 295                 300

Ile Gly Gln Arg Thr Pro Phe Arg Ile Gly Ile Lys Glu Ser Leu Trp
305                 310                 315                 320

Pro Phe Leu Ile Asp Lys Arg Trp Arg Gln Thr Val Phe His
                325                 330
```